(12) United States Patent
Yamamoto et al.

(10) Patent No.: US 9,997,721 B2
(45) Date of Patent: Jun. 12, 2018

(54) PHOTOELECTRIC CONVERSION MATERIAL, PHOTOELECTRIC CONVERSION ELEMENT, OPTICAL SENSOR, AND IMAGING ELEMENT

(71) Applicant: FUJIFILM Corporation, Tokyo (JP)

(72) Inventors: Yosuke Yamamoto, Kanagawa (JP);
Masaaki Tsukase, Kanagawa (JP);
Tomoaki Yoshioka, Kanagawa (JP);
Naoyuki Hanaki, Kanagawa (JP);
Takahiko Ichiki, Kanagawa (JP);
Daigo Sawaki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days. days.

(21) Appl. No.: 15/012,203

(22) Filed: Feb. 1, 2016

(65) Prior Publication Data

US 2016/0149144 A1    May 26, 2016

Related U.S. Application Data

(63) Continuation of application No. PCT/JP2014/069750, filed on Jul. 25, 2014.

(30) Foreign Application Priority Data

Aug. 2, 2013  (JP) .................................. 2013-161754
Feb. 14, 2014  (JP) .................................. 2014-026852

(51) Int. Cl.
| | | |
|---|---|---|
| *H01L 51/00* | (2006.01) | |
| *C07D 257/12* | (2006.01) | |
| *C07D 221/18* | (2006.01) | |
| *C09B 17/00* | (2006.01) | |
| *C09B 19/00* | (2006.01) | |
| *C09B 57/00* | (2006.01) | |
| *C09B 57/08* | (2006.01) | |
| *H01L 51/42* | (2006.01) | |
| *H01L 51/44* | (2006.01) | |

(52) U.S. Cl.
CPC ........ *H01L 51/0072* (2013.01); *C07D 221/18* (2013.01); *C07D 257/12* (2013.01); *C09B 17/00* (2013.01); *C09B 19/00* (2013.01); *C09B 57/00* (2013.01); *C09B 57/001* (2013.01); *C09B 57/008* (2013.01); *C09B 57/08* (2013.01); *H01L 51/0053* (2013.01); *H01L 51/0054* (2013.01); *H01L 51/0046* (2013.01); *H01L 51/0058* (2013.01); *H01L 51/0059* (2013.01); *H01L 51/0094* (2013.01); *H01L 51/42* (2013.01); *H01L 51/442* (2013.01); *Y02E 10/549* (2013.01)

(58) Field of Classification Search
CPC ... H01L 51/0072; H01L 31/04; C07D 221/18; C07D 231/74
USPC ......................................................... 546/200
See application file for complete search history.

(56) References Cited

U.S. PATENT DOCUMENTS

| | | | |
|---|---|---|---|
| 9,035,055 B2 | 5/2015 | Hamano et al. | |
| 9,349,965 B2* | 5/2016 | Yofu .................... | C07D 219/02 |
| 2009/0223566 A1 | 9/2009 | Mitsui et al. | |
| 2011/0056562 A1* | 3/2011 | Hamano ............... | C07C 223/06 |
| | | | 136/263 |
| 2013/0181202 A1 | 7/2013 | Yofu et al. | |

FOREIGN PATENT DOCUMENTS

| | | |
|---|---|---|
| JP | 2001-031961 A | 2/2001 |
| JP | 2011-119745 A | 6/2011 |
| JP | 2011-213706 A | 10/2011 |
| JP | 2012-051854 A | 3/2012 |
| JP | 2012-077064 A | 4/2012 |
| TW | 201127788 A1 | 8/2011 |
| WO | 2012/032990 A1 | 3/2012 |

OTHER PUBLICATIONS

International Search Report of PCT/JP2014/069750 dated Oct. 14, 2014.

Notification of Transmittal of Translation of the International Preliminary Report on Patentability and Translation of Written Opinion of the International Searching Authority; PCT/JP2014/069750 dated Feb. 11, 2016.

An Office Action issued by the Taiwanese Patent Office dated Sep. 6, 2017, which corresponds to Taiwanese Patent Application No. 103126115 and is related to U.S. Appl. No. 15/012,203; with English translation.

* cited by examiner

*Primary Examiner* — Rita J Desai
(74) *Attorney, Agent, or Firm* — Studebaker & Brackett PC

(57) ABSTRACT

An object of the invention is to provide: a photoelectric conversion material which has excellent deposition stability such that when the photoelectric conversion material is used in a photoelectric conversion element, the change in the performance of the element due to variations in the concentration of the photoelectric conversion material is small; a photoelectric conversion element using the photoelectric conversion material; and an optical sensor and an imaging element including the photoelectric conversion element. The photoelectric conversion material of the invention is a compound (A) expressed by the following Formula (1).

Formula (1)

3 Claims, 6 Drawing Sheets

PHOTOELECTRIC CONVERSION MATERIAL, PHOTOELECTRIC CONVERSION ELEMENT, OPTICAL SENSOR, AND IMAGING ELEMENT

CROSS-REFERENCE TO RELATED APPLICATIONS

This application is a continuation of International Application No. PCT/JP2014/069750 filed on Jul. 25, 2014, which claims priority under 35 U.S.C. § 119(a) to Japanese Patent Application No. 2013-161754 filed on Aug. 2, 2013 and Japanese Patent Application No. 2014-026852 filed on Feb. 14, 2014. Each of the above applications is hereby incorporated by reference, in its entirety, into the present application.

BACKGROUND OF THE INVENTION

1. Field of the Invention

The present invention relates to a photoelectric conversion material, a photoelectric conversion element, an optical sensor, and an imaging element.

2. Description of the Related Art

Conventional optical sensors are elements in which photodiodes (PD) are formed in a semiconductor substrate made from silicon (Si) or the like, and as solid-state imaging elements, plane-type solid-state imaging elements in which PDs are two-dimensionally arranged, and signal charges generated by the PDs are read out by circuits are widely used.

In order to realize color solid-state imaging elements, a structure in which a color filter which transmits light of a specific wavelength is disposed on the light incident surface side of a plane-type solid-state imaging element is generally used. Currently, single plate-type solid-state imaging elements in which color filters which transmit blue (B) light, green (G) light, and red (R) light are regularly arranged on two-dimensionally arranged PDs which are widely used in digital cameras and the like are well known.

In recent years, solid-state imaging elements having a structure in which an organic photoelectric conversion film is formed on a substrate for signal readout have been developed.

In solid-state imaging elements or photoelectric conversion elements using such an organic photoelectric conversion film, improvements in responsiveness and photoelectric conversion efficiency are particularly considered to be a task.

For example, JP2011-119745A, JP2011-213706A, and JP2012-77064A disclose a photoelectric conversion material having a specific structure and a photoelectric conversion element having a photoelectric conversion film containing the photoelectric conversion material.

SUMMARY OF THE INVENTION

Recently, a photoelectric conversion material has been required to be continuously deposited over a long period of time in the production of a photoelectric conversion element having a photoelectric conversion film from the viewpoint of an improvement in productivity. Therefore, it is required that even when a photoelectric conversion material in a crucible is exposed to a high-temperature environment for a long period of time, decomposition is suppressed as much as possible. That is, the photoelectric conversion material requires deposition stability (decomposition resistance of the photoelectric conversion material under a high-temperature environment).

In addition, in the manufacturing of a photoelectric conversion element, there may be variations in the amount of a photoelectric conversion material deposited, and such variations may affect the performance of the element and may lead to a reduction in the yield. Recently, from the viewpoint of an improvement in the yield, the change in the performance of the element due to variations in the concentration of the photoelectric conversion material in a photoelectric conversion film is required to be small.

The inventors have conducted studies on the photoelectric conversion material disclosed in JP2011-119745A, JP2011-213706A, and JP2012-77064A, and it turned out that the material is insufficient in deposition stability, and a level required these days is not satisfied.

In addition, the inventors have conducted studies on the photoelectric conversion element disclosed in JP2011-119745A, JP2011-213706A, and JP2012-77064A, and it turned out that the change in the performance of the element due to variations in the concentration of the photoelectric conversion material in the photoelectric conversion film is large, and a level required these days is not satisfied.

In view of the actual circumstances, an object of the invention is to provide: a photoelectric conversion material which has excellent deposition stability such that when the photoelectric conversion material is used in a photoelectric conversion element, the change in the performance of the element due to variations in the concentration of the photoelectric conversion material is small; a photoelectric conversion element using the photoelectric conversion material; and an optical sensor and an imaging element including the photoelectric conversion element.

The inventors have conducted intensive studies on the above-described task, and as a result, have found that a compound (A) expressed by Formula (1) to be described later has excellent deposition stability as a photoelectric conversion material, and when a photoelectric conversion material which is the compound (A) expressed by Formula (1) to be described later is used in a photoelectric conversion film, the performance of an element hardly changes even when there are variations in the concentration of the photoelectric conversion material in the photoelectric conversion film, and completed the invention. That is, the inventors have found that the task can be solved by the following configurations.

(1) A photoelectric conversion material which is a compound (A) expressed by Formula (1) to be described later.

(2) The photoelectric conversion material according to (1), in which $Z_1$ is a ring expressed by Formula (Z1) to be described later.

(3) The photoelectric conversion material according to (1) or (2), in which $Ar_{11}$ is an arylene group which may have a substituent.

(4) The photoelectric conversion material according to any one of (1) to (3), in which at least one of $Ar_{11}$, $Ar_{12}$, and $Ar_{13}$ has the specific substituent.

(5) The photoelectric conversion material according to any one of (1) to (4), in which the compound (A) is a compound (a1) expressed by Formula (2) to be described later.

(6) The photoelectric conversion material according to any one of (1) to (5), in which n is 0.

(7) The photoelectric conversion material according to (5) or (6), in which the compound (A) is a compound (a2) expressed by Formula (3) to be described later.

(8) The photoelectric conversion material according to (7), in which at least one of $R_{33}$ and $R_{38}$ is the specific substituent, and at least one type of atom selected from the group consisting of oxygen atom, sulfur atom, selenium atom, silicon atom, and germanium atom included in the specific substituent is directly bonded to a carbon atom to which $R_{33}$ or $R_{38}$ is bonded.

(9) A photoelectric conversion element including, in this order: a conductive film; a photoelectric conversion film containing the photoelectric conversion material according to any one of (1) to (8); and a transparent conductive film.

(10) The photoelectric conversion element according to (9), in which the photoelectric conversion film further contains an n-type organic semiconductor.

(11) The photoelectric conversion element according to (10), in which the n-type organic semiconductor includes fullerenes selected from the group consisting of fullerenes and derivatives thereof.

(12) The photoelectric conversion element according to (11), in which the content of the fullerenes with respect to the total content of the photoelectric conversion material and the fullerenes (=film thickness of fullerenes in terms of single layer/(film thickness of photoelectric conversion material in terms of single layer+film thickness of fullerenes in terms of single layer)) is 50 vol % or greater.

(13) The photoelectric conversion element according to any one of (9) to (12), in which a charge blocking layer is disposed between the conductive film and the transparent conductive film.

(14) The photoelectric conversion element according to (13), in which the charge blocking layer is an electron blocking layer, and the electron blocking layer contains a compound expressed by Formula (EB-1) to be described later.

(15) The photoelectric conversion element according to any one of (9) to (14), in which the compound expressed by Formula (EB-1) is a compound expressed by Formula (EB-2) to be described later.

(16) The photoelectric conversion element according to any one of (9) to (15), in which light enters the photoelectric conversion film via the transparent conductive film.

(17) The photoelectric conversion element according to any one of (9) to (16), in which the transparent conductive film is formed of a transparent conductive metal oxide.

(18) An optical sensor including the photoelectric conversion element according to (9) to (17).

(19) An imaging element including the photoelectric conversion element according to any one of (9) to (17).

As shown below, according to the invention, it is possible to provide: a photoelectric conversion material which has excellent deposition stability such that when the photoelectric conversion material is used in a photoelectric conversion element, the change in the performance of the element due to variations in the concentration of the photoelectric conversion material is small; a photoelectric conversion element using the photoelectric conversion material; and an optical sensor and an imaging element including the photoelectric conversion element.

DESCRIPTION OF THE PREFERRED EMBODIMENTS

[Photoelectric Conversion Material]

Figure 1A:
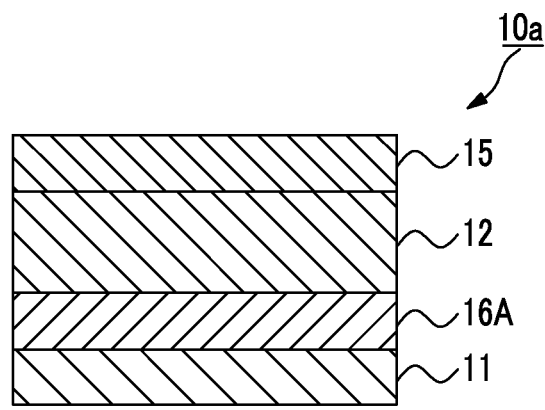
FIGS. 1(a) and 1(b) are schematic cross-sectional views each showing an embodiment of a photoelectric conversion element.

A photoelectric conversion material of the invention is a compound (A) expressed by Formula (1) to be described later. Since the photoelectric conversion material of the invention has a specific structure expressed by Formula (1) to be described later, it is thought to be a material exhibiting excellent deposition stability.

The reason for this is not clear, but is presumed as follows.

The photoelectric conversion material of the invention is a compound having a structure in which triarylamine and a ring indicated by $Z_1$ are connected as will be described later. Since the triarylamine exhibits electron-donating (donor) properties, and the ring indicated by $Z_1$ exhibits electron-accepting (acceptor) properties, satisfactory charge separation occurs in the molecule of the compound due to light absorption.

Here, as will be described later, in the photoelectric conversion material of the invention, the triarylamine or the ring indicated by $Z_1$ has a specific substituent (monovalent substituent including at least one type of atom selected from the group consisting of oxygen atom, sulfur atom, selenium atom, silicon atom, and germanium atom), and the triarylamine forms a ring (more specifically, an arylene group and an aryl group of the triarylamine form a ring). Therefore, it is thought that the intermolecular distance can be increased, the π-π interaction is weakened, and an increase in the deposition temperature can be suppressed. By introducing the specific substituent, many CH-π interactions can be introduced, and as a result, the melting point is thought to be improved. The reason why an increase in the deposition temperature can be suppressed even when the CH-π interactions are introduced is thought to be that the CH-π interactions are induced dipole interactions between points and planes, and upon deposition, these interactions temporarily disappear due to thermal fluctuation. Accordingly, the photoelectric conversion material of the invention is thought to be a material in which an increase in the deposition temperature is suppressed while a high melting point (decomposition temperature) is maintained. As a result, the photoelectric conversion material of the invention is thought to be a material which can be deposited while the decomposition thereof is suppressed. That is, the photoelectric conversion material of the invention is thought to be a material exhibiting excellent deposition stability. As will be shown in comparative examples to be described later, this is also presumed from the fact that the deposition stability becomes insufficient when the triarylamine forms a ring, but the triarylamine or the ring indicated by $Z_1$ has no specific substituent (Comparative Examples 1-3 to 1-5), or when the triarylamine or the ring indicated by $Z_1$ has a specific substituent, but the triarylamine does not form a ring (Comparative Examples 1-1 and 1-2).

The photoelectric conversion material of the invention is the compound (A) expressed by the following Formula (1).

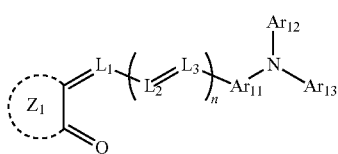

Formula (1)

In Formula (1), $Z_1$ is a ring including at least two carbon atoms, and indicates a five-membered ring, a six-membered ring, or a condensed ring including at least any one of the five-membered ring and the six-membered ring.

As such a ring, those which are generally used as an acidic nucleus in a merocyanine dye are preferred, and specific examples thereof include the following materials.

(a) 1,3-Dicarbonyl Nucleus: for example, 1,3-indanedion nucleus, 1,3-cyclohexanedione, 5,5-dimethyl-1,3-cyclohexanedione, 1,3-dioxane-4,6-dione, and the like.

(b) Pyrazolinone Nucleus: for example, 1-phenyl-2-pyrazoline-5-one, 3-methyl-1-phenyl-2-pyrazoline-5-one, 1-(2-benzothiazoyl)-3-methyl-2-pyrazoline-5-one, and the like.

(c) Isoxazolinone Nucleus: for example, 3-phenyl-2-isoxazoline-5-one, 3-methyl-2-isoxazoline-5-one, and the like.

(d) Oxindole Nucleus: for example, 1-alkyl-2,3-dihydro-2-oxindole, and the like.

(e) 2,4,6-Triketohexahydropyrimidine Nucleus: for example, barbituric acid or 2-thiobarbituric acid, and derivatives thereof, and the like. Examples of the derivatives include 1-alkyl derivatives such as 1-methyl and 1-ethyl, 1,3-dialkyl derivatives such as 1,3-dimethyl, 1,3-diethyl, and 1,3-dibutyl, 1,3-diaryl derivatives such as 1,3-diphenyl, 1,3-di(p-chlorophenyl), and 1,3-di(p-ethoxycarbonylphenyl), 1-alkyl-1-aryl derivatives such as 1-ethyl-3-phenyl, 1,3-diheterocyclic-substituted derivatives such as 1,3-di(2-pyridyl), and the like.

(f) 2-Thio-2,4-Thiazolidinedione Nucleus: for example, rhodanine and derivatives thereof. Examples of the derivatives include 3-alkylrhodanine such as 3-methylrhodanine, 3-ethylrhodanine, and 3-allylrhodanine, 3-arylrhodanine such as 3-phenylrhodanine, 3-heterocyclic-substituted rhodanine such as 3-(2-pyridyl)rhodanine, and the like.

(g) 2-Thio-2,4-Oxazolidinedione(2-Thio-2,4-(3H,5H)-Oxazoledione) Nucleus: for example, 3-ethyl-2-thio-2,4-oxazolidinedione, and the like.

(h) Thianaphthenone Nucleus: for example, 3(2H)-thianaphthenone-1,1-dioxide, and the like.

(i) 2-Thio-2,5-Thiazolidinedione Nucleus: for example, 3-ethyl-2-thio-2,5-thiazolidinedione, and the like.

(j) 2,4-Thiazolidinedione Nucleus: for example, 2,4-thiazolidinedione, 3-ethyl-2,4-thiazolidinedione, 3-phenyl-2,4-thiazolidinedione, and the like.

(k) Thiazoline-4-One Nucleus: for example, 4-thiazolinone, 2-ethyl-4-thiazolinone, and the like.

(l) 2,4-Imidazolidinedione (hydantoin) Nucleus: for example, 2,4-imidazolidinedione, 3-ethyl-2,4-imidazolidinedione, and the like.

(m) 2-Thio-2,4-Imidazolidinedione(2-Thiohydantoin) Nucleus: for example, 2-thio-2,4-imidazolidinedione, 3-ethyl-2-thio-2,4-imidazolidinedione, and the like.

(n) Imidazoline-5-One Nucleus: for example, 2-propylmercapto-2-imidazoline-5-one, and the like.

(o) 3,5-Pyrazolidinedione Nucleus: for example, 1,2-diphenyl-3,5-pyrazolidinedione, 1,2-dimethyl-3,5-pyrazolidinedione, and the like.

(p) Benzothiophene-3-One Nucleus: for example, benzothiophene-3-one, oxobenzothiophene-3-one, dioxobenzothiophene-3-one, and the like.

(q) Indanone Nucleus: for example, 1-indanone, 3-phenyl-1-indanone, 3-methyl-1-indanone, 3,3-diphenyl-1-indanone, 3,3-dimethyl-1-indanone, and the like.

$Z_1$ may have a substituent. Examples of the substituent include a substituent W to be described later, and the like.

$Z_1$ is preferably a group expressed by the following Formula (Z1) in view of more excellent responsiveness and sensitivity.

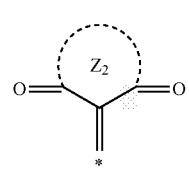

Formula (Z1)

In Formula (Z1), $Z_2$ is a ring including at least three carbon atoms, and indicates a five-membered ring, a six-membered ring, or a condensed ring including at least any one of the five-membered ring and the six-membered ring.

In Formula (Z1), * indicates a bonding position with $L_1$.

In Formula (1), each of $L_1$, $L_2$, and $L_3$ independently indicates a methine group which may have a substituent. Examples of the substituent include a substituent W to be described later, and the like.

n indicates an integer of 0 or greater. n is preferably 0 to 3, and more preferably 0.

In Formula (1), $Ar_{11}$ indicates an arylene group or a heteroarylene group which may have a substituent. Examples of the substituent include a substituent W to be described later, and the like.

$Ar_{11}$ is preferably an arylene group which may have a substituent.

When $Ar_{11}$ is an arylene group, $Ar_{11}$ is preferably an arylene group having 6 to 30 carbon atoms, and is more preferably an arylene group having 6 to 20 carbon atoms. Specific examples of the ring constituting the arylene group include a benzene ring, a naphthalene ring, an anthracene ring, a phenanthrene ring, a fluorene ring, a triphenylene ring, a naphthacene ring, a biphenyl ring (two phenyl groups may be connected in an arbitrary connecting manner), a terphenyl ring (three benzene rings may be connected in an arbitrary connecting manner), and the like.

When $Ar_{11}$ is a heteroarylene group, $Ar_{11}$ is preferably a heteroarylene group composed of a five-, six-, or seven-membered ring, or a condensed ring thereof. Examples of the hetero atom contained in the heteroarylene group include an oxygen atom, a sulfur atom, a nitrogen atom, and the like. Specific examples of the ring constituting the heteroarylene group include a furan ring, a thiophene ring, a pyrrole ring, a pyrroline ring, a pyrrolidine ring, an oxazole ring, an isoxazole ring, a thiazole ring, an isothiazole ring, an imidazole ring, an imidazoline ring, an imidazolidine ring, a pyrazole ring, a pyrazoline ring, a pyrazolidine ring, a triazole ring, a furazane ring, a tetrazole ring, a pyran ring, a thiin ring, a pyridine ring, a piperidine ring, an oxazine ring, a morpholine ring, a thiazine ring, a pyridazine ring, a pyrimidine ring, a pyrazine ring, a piperazine ring, a triazine ring, a benzofuran ring, an isobenzofuran ring, a benzothiophene ring, an indole ring, an indoline ring, an isoindole ring, a benzoxazole ring, a benzothiazole ring, an indazole ring, a benzimidazole ring, a quinoline ring, an isoquinoline ring, a cinnoline ring, a phthalazine ring, a quinazoline ring, a quinoxaline ring, a dibenzofuran ring, a dibenzothiophene ring, a carbazole ring, a xanthene ring, an acridine ring, a phenanthridine ring, a phenanthroline ring, a phenazine ring, a phenoxazine ring, a thianthrene ring, an indolizine ring, a quinolizine ring, a quinuclidine ring, a naphthyridine ring, a purine ring, a pteridine ring, and the like.

$Ar_{11}$ and $L_1$ may be bonded to each other to form a ring. Examples of the ring to be formed include a ring R to be described later, and the like. The ring formed by bonding $Ar_{11}$ and $L_1$ may have a substituent. Examples of the substituent include a substituent W to be described later, and the like.

In Formula (1), each of $Ar_{12}$ and $Ar_{13}$ independently indicates an aryl group or a heteroaryl group which may have a substituent. Examples of the substituent include a substituent W to be described later, and the like.

When $Ar_{12}$ or $Ar_{13}$ is an aryl group, $Ar_{12}$ or $Ar_{13}$ is preferably an aryl group having 6 to 30 carbon atoms, and is more preferably an aryl group having 6 to 20 carbon atoms. Specific examples of the ring constituting the aryl group are the same as those in the case in which $Ar_{11}$ is an arylene group.

When $Ar_{12}$ or $Ar_{13}$ is a heteroaryl group, $Ar_{12}$ or $Ar_{13}$ is preferably a heteroaryl group composed of a five-, six-, or seven-membered ring, or a condensed ring thereof. Specific examples of the hetero atom contained in the heteroaryl group are the same as those in the case in which $Ar_{11}$ is a heteroarylene group. Specific examples of the ring constituting the heteroaryl group are the same as those in the case in which $Ar_{11}$ is a heteroarylene group.

$Ar_{12}$ and $Ar_{13}$ may be bonded to each other to form a ring. Examples of the ring to be formed include a ring R to be described later, and the like.

At least one of $Ar_{11}$ and $Ar_{12}$; and $Ar_{11}$ and $Ar_{13}$ are bonded to each other to form a ring. Examples of the ring to be formed include a ring R to be described later, and the like.

(Specific Substituent)

At least one of $Z_1$, $Ar_{11}$, $Ar_{12}$, and $Ar_{13}$ has a specific substituent.

Here, the specific substituent is a monovalent substituent including at least one type of atom (hereinafter, also referred to as specific atom) selected from the group consisting of oxygen atom, sulfur atom, selenium atom, silicon atom, and germanium atom.

It is preferable that at least one of $Ar_{11}$, $Ar_{12}$, and $Ar_{13}$ has a specific substituent, and it is more preferable that at least one of $Ar_{12}$ and $Ar_{13}$ has a specific substituent.

The specific substituent is preferably a group including a specific atom and a hydrocarbon group.

When the specific substituent is a group including a specific atom and a hydrocarbon group, the hydrocarbon group is not particularly limited, and examples thereof include an aliphatic hydrocarbon group and an aromatic hydrocarbon group. Among these, an aliphatic hydrocarbon group is preferred.

The aliphatic hydrocarbon group may be a linear, branched, or cyclic group. Specific examples of the aliphatic hydrocarbon group include a linear or branched alkyl group (particularly, having 1 to 20 carbon atoms), a linear or branched alkenyl group (particularly, having 2 to 20 carbon atoms), a linear or branched alkynyl group (particularly, having 2 to 20 carbon atoms), and the like. The aliphatic hydrocarbon group is preferably a linear or branched alkyl group.

Examples of the aromatic hydrocarbon group include an aryl group, a naphthyl group, and the like. Examples of the aryl group include aryl groups having 6 to 18 carbon atoms such as a phenyl group, a tolyl group, and a xylyl group, and the like.

The position of the specific atom in the specific substituent is not particularly limited, but for example, the specific atom is preferably disposed at a bonding position as in the cases of groups expressed by Formulae (X1) to (X5) to be described later.

When the specific substituent includes a sulfur atom, the valence of the sulfur atom is not particularly limited, but is preferably two. That is, when the specific substituent includes a sulfur atom, the sulfur atom is preferably included as a sulfide group (—S—).

The specific substituent preferably includes a silicon atom or an oxygen atom, and more preferably includes a silicon atom since the deposition stability is improved.

As preferred aspects of the specific substituent, groups expressed by the following Formulae (X1) to (X5) can be exemplified. Among these, groups expressed by the following Formula (X4) are preferred since the deposition stability is improved.

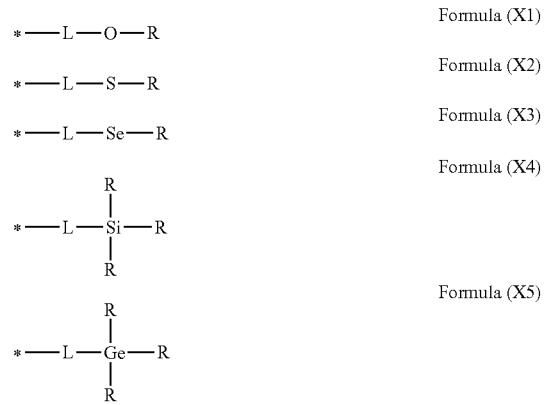

In Formulae (X1) to (X5), R indicates a hydrocarbon group. Specific examples and preferred aspects of R are the same as those of a hydrocarbon group when the above-described specific substituent is a group including a specific atom and a hydrocarbon group. A plurality of Rs may be the same as or different from each other.

In Formulae (X1) to (X5), L indicates a single bond or a divalent organic group. Among these, a single bond is preferred. Examples of the divalent organic group include a divalent aliphatic hydrocarbon group which may have a substituent (for example, alkylene group preferably having 1 to 8 carbon atoms), a divalent aromatic hydrocarbon group which may have a substituent (for example, arylene group preferably having 6 to 12 carbon atoms), —O—, —S—, —SO$_2$—, —NR— (R: substituent (for example, substituent W to be described later)), —SiR$^1$R$^2$— (R$^1$ and R$^2$: substituent (for example, substituent W to be described later)), —CO—, —NH—, —COO—, —CONH—, a group composed of a combination thereof (for example, alkyleneoxy group, alkyleneoxycarbonyl group, and alkylenecarbonyloxy group), and the like. Among these, a divalent aliphatic hydrocarbon group which may have a substituent is preferred. Examples of the substituent include a substituent W to be described later, and the like.

In Formulae (X1) to (X5), * indicates a bonding position.

As a preferred aspect of the compound (A), a compound (a1) expressed by the following Formula (2) can be exemplified.

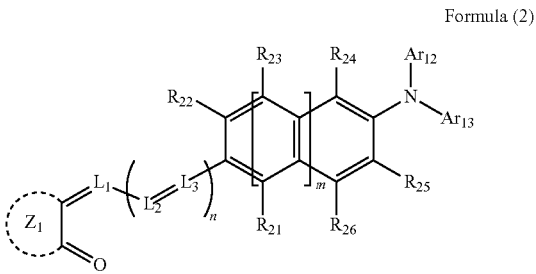

Formula (2)

In Formula (2), a definition, specific examples, and preferred aspects of $Z_1$ are the same as those in Formula (1).

In Formula (2), definitions of $L_1$, $L_2$, and $L_3$ are the same as those in Formula (1).

In Formula (2), a definition and preferred aspects of n are the same as those in Formula (1).

In Formula (2), each of $R_{21}$ to $R_{26}$ independently indicates a hydrogen atom or a substituent. Examples of the substituent include a substituent W to be described later, and the like. $R_{22}$ and $R_{23}$; $R_{23}$ and $R_{24}$; $R_{25}$ and $R_{26}$; and $R_{21}$ and $R_{26}$ may be respectively bonded to each other to form a ring. Examples of the ring to be formed include a ring R to be described later, and the like.

In Formula (2), m indicates 0 or 1. Among these, 1 is preferred.

In the case of m=0, Formula (2) is the following Formula (2-1).

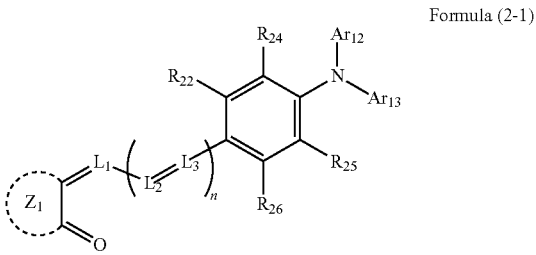

Formula (2-1)

In the case of m=1, Formula (2) is the following Formula (2-2).

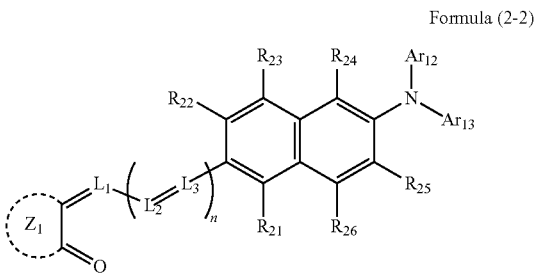

Formula (2-2)

In Formula (2), definitions, specific examples, and preferred aspects of $Ar_{12}$ and $Ar_{13}$ are the same as those in Formula (1).

At least one of $Ar_{12}$ and $Ar_{13}$ is bonded to any of $R_{21}$ to $R_{26}$ via Xa, which is a single bond or a divalent group, to form a ring. When a ring is formed, $R_{21}$ to $R_{26}$ may be direct bonds.

Here, Xa indicates an oxygen atom (—O—), a sulfur atom (—S—), an alkylene group, a silylene group (—$SiR_aR_b$—: each of $R_a$ and $R_b$ independently indicates a hydrogen atom or a substituent (for example, substituent W to be described later)), $NR_a$— ($R_a$ indicates a hydrogen atom or a substituent (for example, substituent W to be described later)), an alkenylene group, a cycloalkylene group, a cycloalkenylene group, an arylene group, or a heteroarylene group. Xa may have a substituent.

Formula (2) satisfies at least one of the following (i) and (ii). Among these, the following (i) is preferably satisfied.

(i) At least one of $Ar_{12}$ and $Ar_{13}$ has the specific substituent.

(ii) At least one of $R_{21}$ to $R_{26}$ is the specific substituent.

As a preferred aspect of the compound (a1), a compound (a2) expressed by the following Formula (3) can be exemplified.

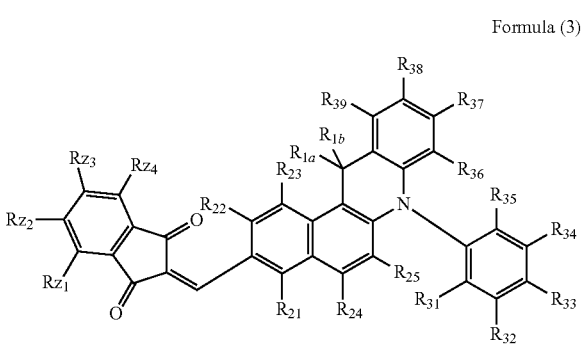

Formula (3)

In Formula (3), each of $Rz_1$ to $Rz_4$ independently indicates a hydrogen atom or a substituent. Examples of the substituent include a substituent W to be described later, and the like. $Rz_1$ and $Rz_2$; $Rz_2$ and $Rz_3$; and $Rz_3$ and $Rz_4$ may be respectively bonded to each other to form a ring. Examples of the ring to be formed include a ring R to be described later, and the like.

In Formula (3), each of $R_{21}$, $R_{22}$, $R_{23}$, $R_{25}$, and $R_{26}$ independently indicates a hydrogen atom or a substituent. Examples of the substituent include a substituent W to be described later, and the like. $R_{22}$ and $R_{23}$; $R_{25}$ and $R_{26}$; and $R_{21}$ and $R_{26}$ may be respectively bonded to each other to form a ring. Examples of the ring to be formed include a ring R to be described later, and the like.

In Formula (3), each of $R_{1a}$ and $R_{1b}$ independently indicates a hydrogen atom or a substituent. Examples of the substituent include a substituent W to be described later, and the like. Among these, an alkyl group (particularly, having 1 to 20 carbon atoms) is preferred, and an alkyl group having 1 to 3 carbon atoms is more preferred. $R_{1a}$ and $R_{1b}$ may be bonded to each other to form a ring. Examples of the ring to be formed include a ring R to be described later, and the like.

In Formula (3), each of $R_{31}$ to $R_{35}$ independently indicates a hydrogen atom or a substituent. Examples of the substituent include a substituent W to be described later, and the like. $R_{31}$ and $R_{32}$; $R_{32}$ and $R_{33}$; $R_{33}$ and $R_{34}$; and $R_{34}$ and $R_{35}$ may be respectively bonded to each other to form a ring. Examples of the ring to be formed include a ring R to be described later, and the like.

In Formula (3), each of $R_{36}$ to $R_{39}$ independently indicates a hydrogen atom or a substituent. Examples of the substituent include a substituent W to be described later, and the like. $R_{36}$ and $R_{37}$; $R_{37}$ and $R_{38}$; and $R_{38}$ and $R_{39}$ may be respectively bonded to each other to form a ring. Examples of the ring to be formed include a ring R to be described later, and the like.

Formula (3) satisfies at least one of the following (i) and (ii). Among these, the following (i) is preferably satisfied.

(i) At least one of $R_{31}$ and $R_{39}$ is the specific substituent.

(ii) At least one of $R_{21}$, $R_{22}$, $R_{23}$, $R_{25}$, and $R_{26}$ is the specific substituent.

In Formula (3), at least one of $R_{33}$ and $R_{38}$ is preferably the specific substituent. Among these, the specific atom included in the specific substituent is more preferably directly bonded to a carbon atom to which $R_{33}$ or $R_{38}$ is bonded.

(Substituent W)

The substituent W in this description will be described.

Examples of the substituent W include a halogen atom, an alkyl group (including cycloalkyl group, bicyclo alkyl group, and tricycloalkyl group), an alkenyl group (including cycloalkenyl group and bicycloalkenyl group), an alkynyl group, an aryl group, a heterocyclic group (may also be referred to as hetero ring group), a cyano group, a hydroxy group, a nitro group, a carboxy group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group (including anilino group), an ammonio group, an acylamino group, an aminocarbonylamino group, an alkoxycarbonylamino group, an aryloxycarbonylamino group, a sulfamoylamino group, an alkyl- or arylsulfonylamino group, a mercapto group, an alkylthio group, an arylthio group, a heterocyclicthio group, a sulfamoyl group, a sulfo group, an alkyl- or arylsulfinyl group, an alkyl- or arylsulfonyl group, an acyl group, an aryloxycarbonyl group, an alkoxycarbonyl group, a carbamoyl group, an aryl- or heterocyclic azo group, an imide group, a phosphino group, a phosphinyl group, a phosphinyloxy group, a phosphinylamino group, a phosphono group, a silyl group, a hydrazino group, a ureido group, a boronic acid group (—B(OH)$_2$), a phosphate group (—OPO(OH)$_2$), a sulfate group (—OSO$_3$H), and other known substituents.

(Ring R)

The ring R in this description will be described.

Examples of the ring R include an aromatic hydrocarbon ring, an aromatic heterocycle, a non-aromatic hydrocarbon ring, a non-aromatic heterocycle, and a polycyclic condensed ring composed of a combination thereof. More specific examples thereof include a benzene ring, a naphthalene ring, an anthracene ring, a phenanthrene ring, a fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a quinolizine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthridine ring, a thianthrene ring, a chromene ring, a xanthene ring, a phenoxathiin ring, a phenothiazine ring, or a phenazine ring, a cyclopentane ring, a cyclohexane ring, a pyrrolidine ring, a piperidine ring, a tetrahydropyran ring, a tetrahydropyran ring, a tetrahydrothiophene ring, a tetrahydrothiopyran ring, and the like.

The ring R may have a substituent. Examples of the substituent include the above-described substituent W, and the like.

The compound (A) can be manufactured by partially changing and carrying out a known method. Hereinafter, specific examples of the compound (A) will be shown, but the invention is not limited thereto. In the following specific examples, "TMS" indicates a trimethylsilyl group, "MeO—" (—OMe) indicates a methoxy group, and "MeS—" (—SMe) indicates a methylthio group (CH$_3$—S—).

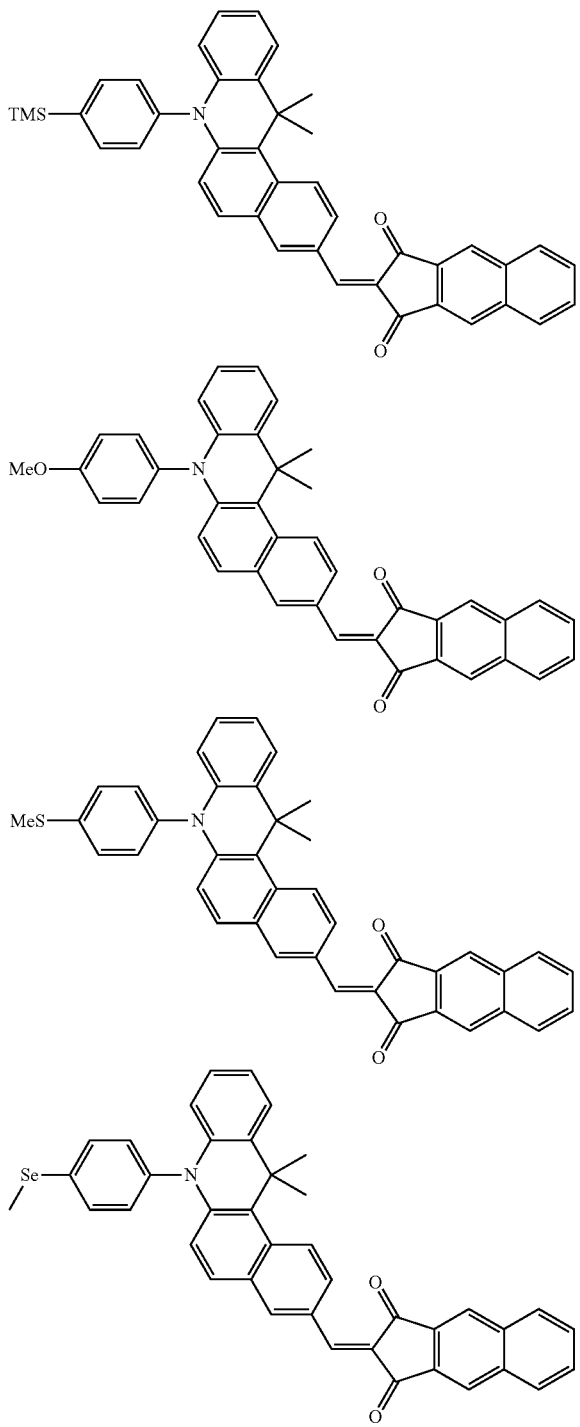

-continued
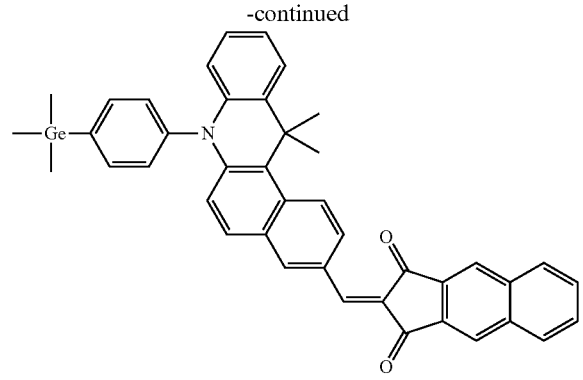
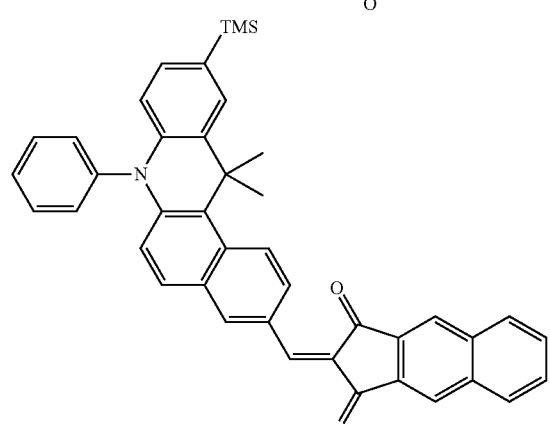
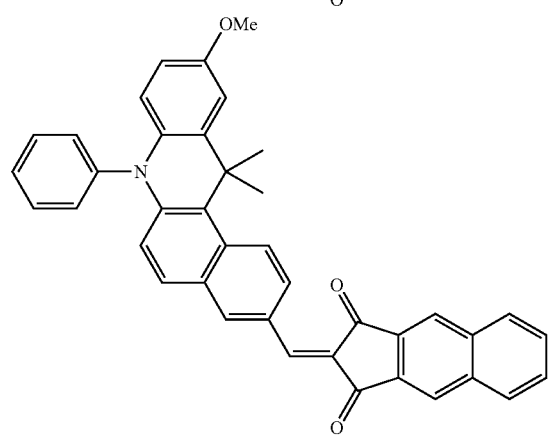
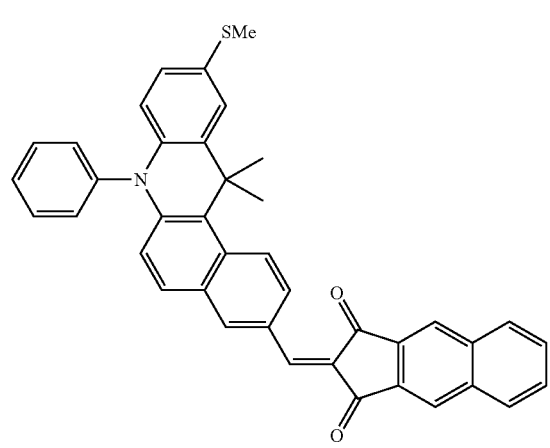
-continued
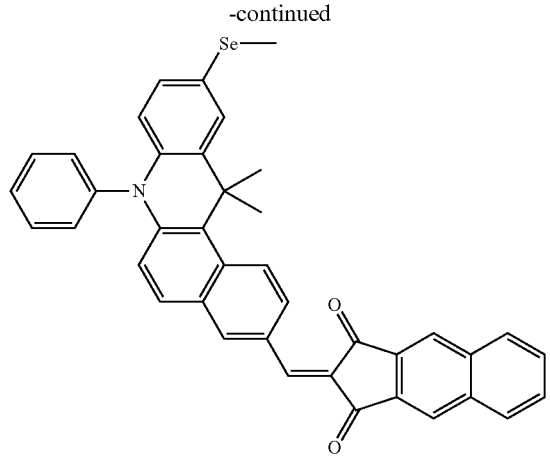
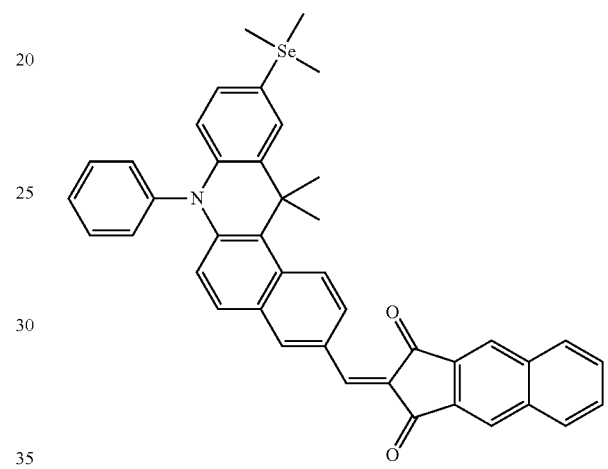
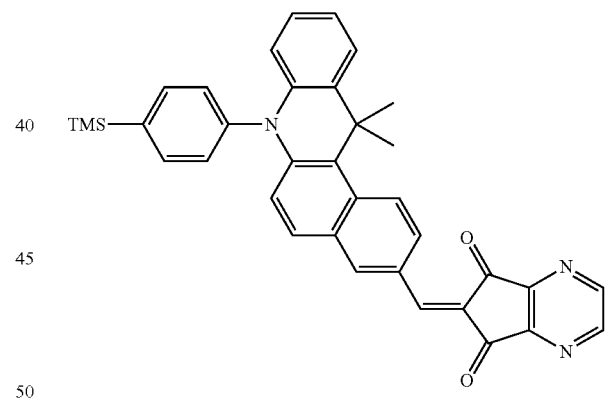
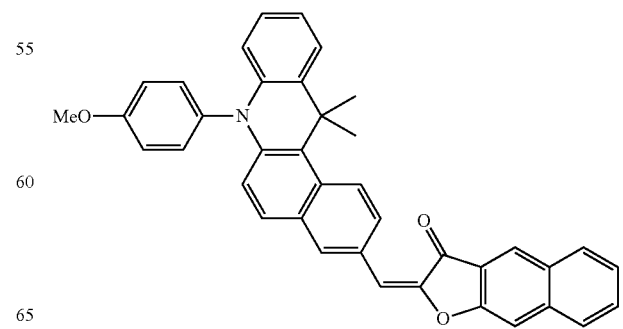

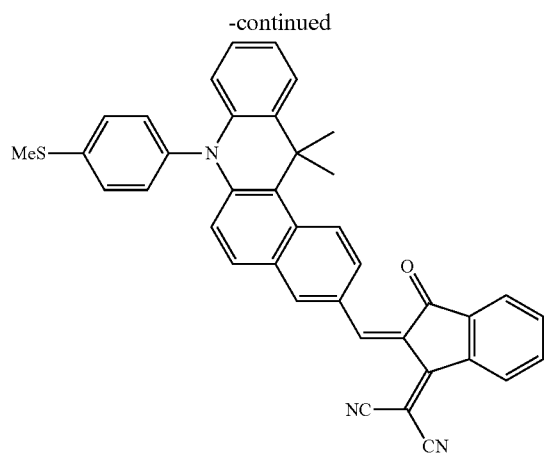
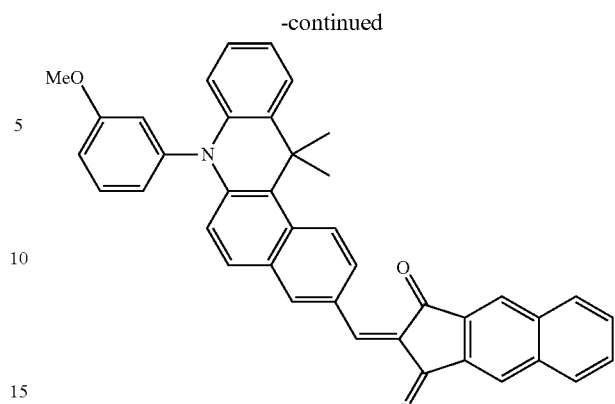
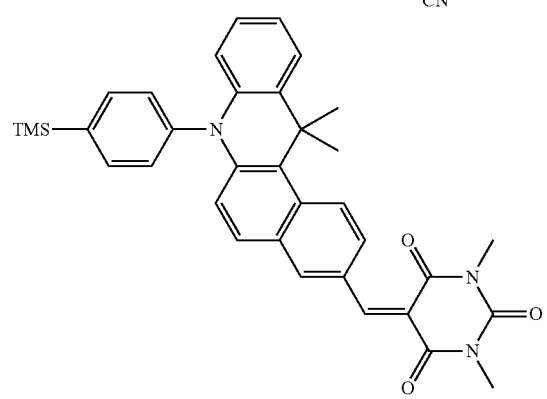
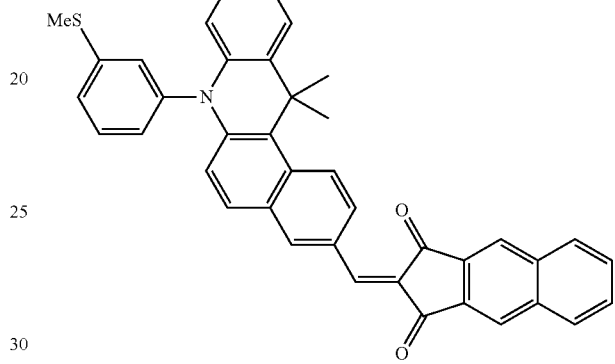
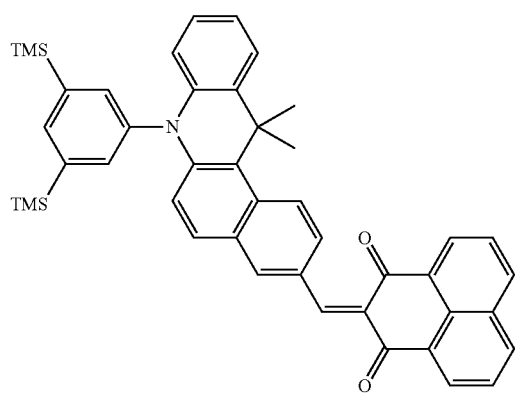
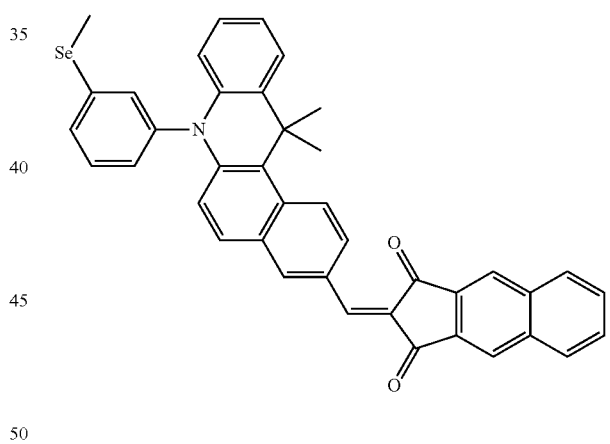
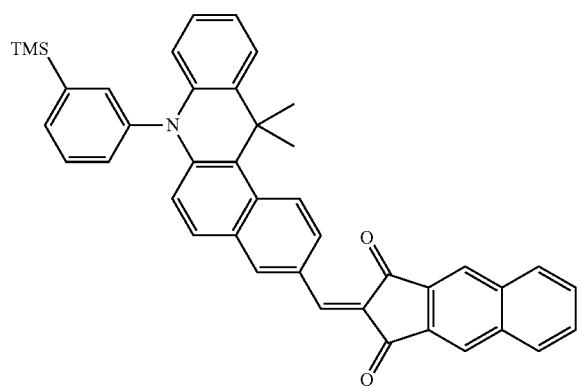
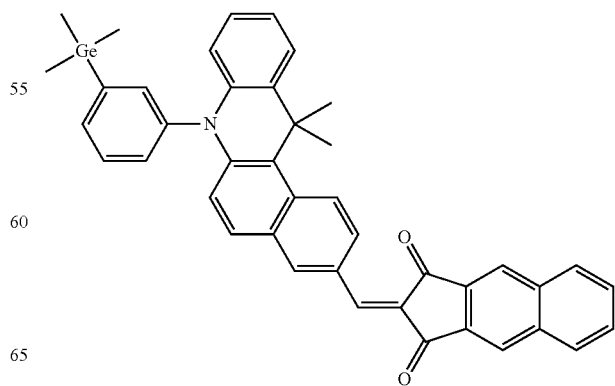

17
-continued
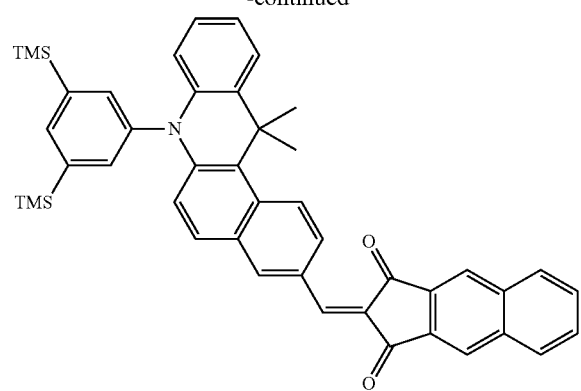
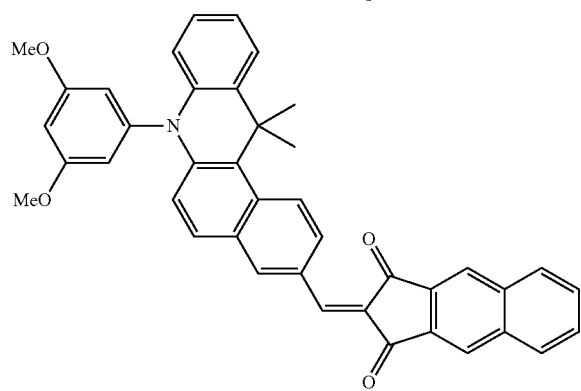
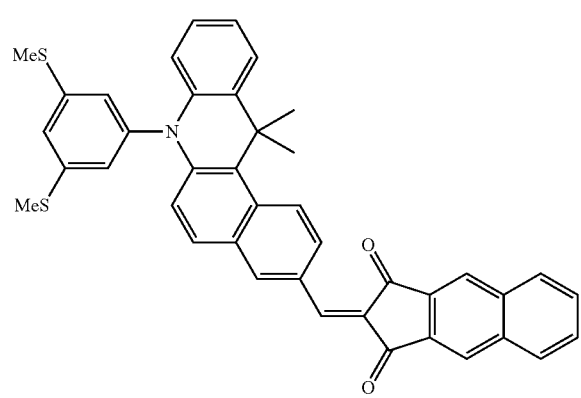
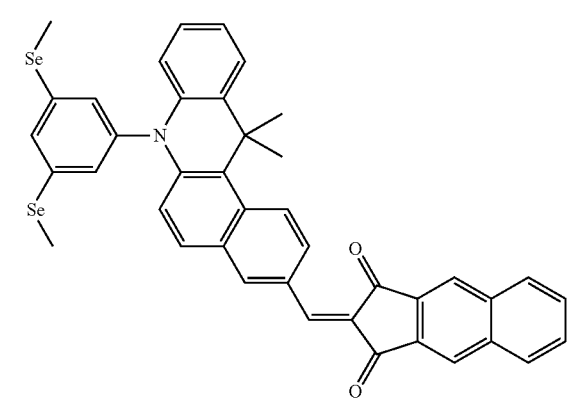
18
-continued
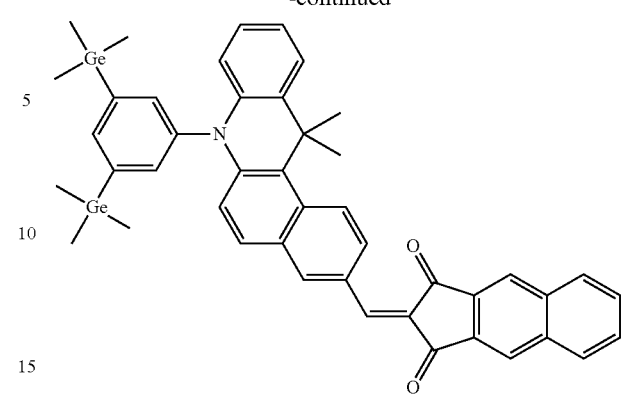
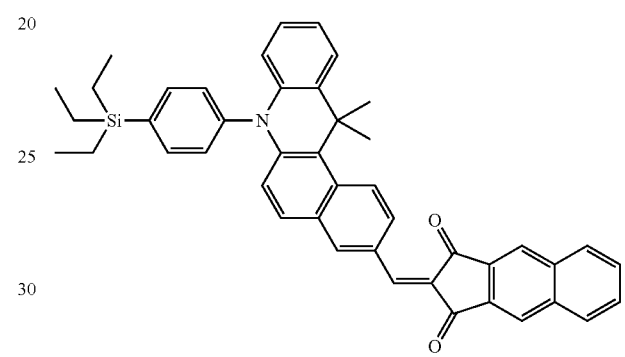
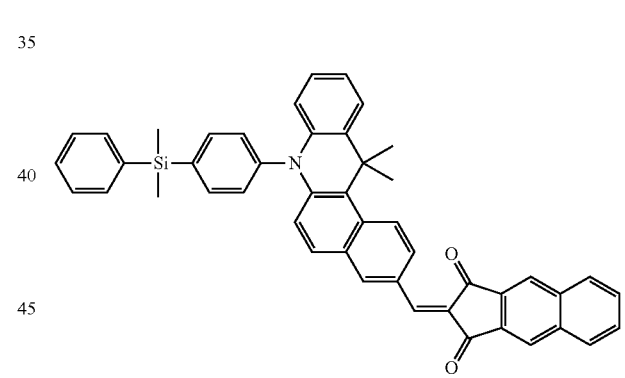
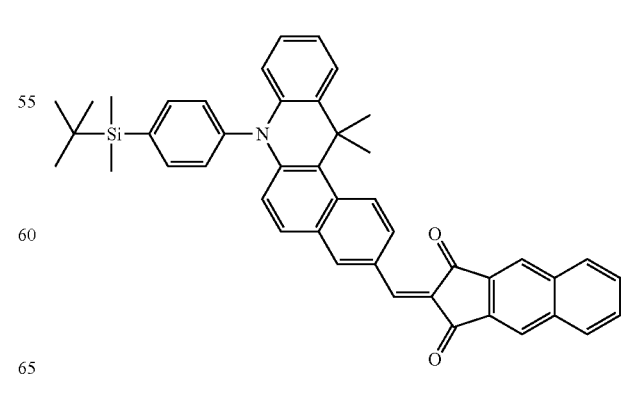

19
-continued
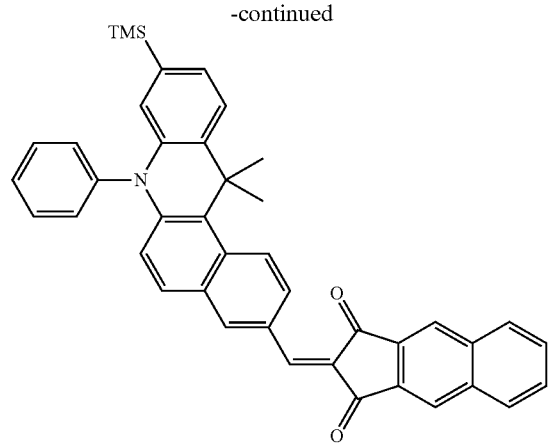
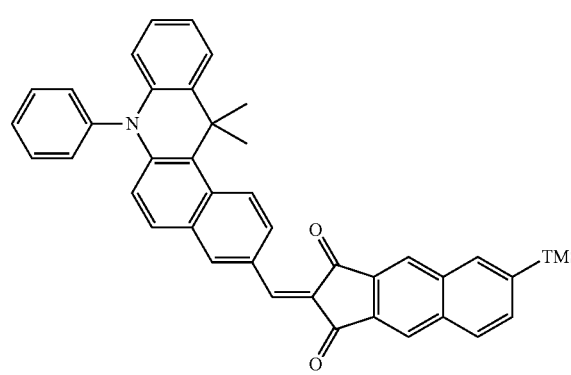
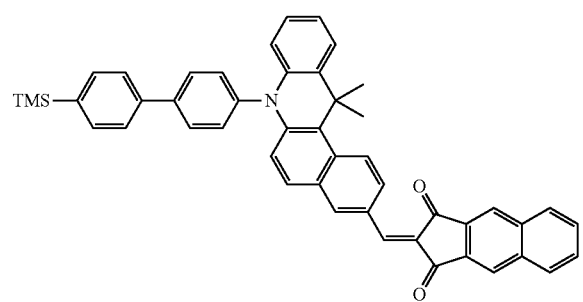
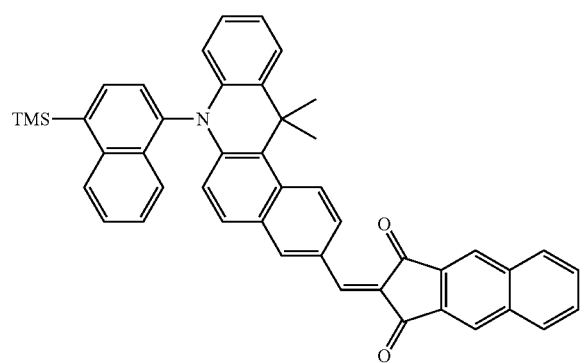
20
-continued
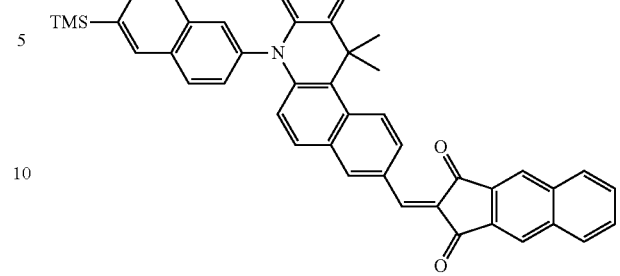
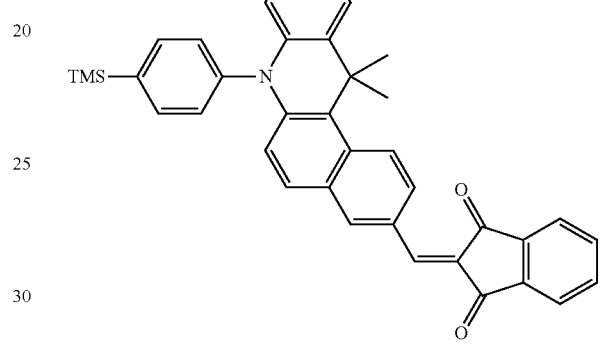
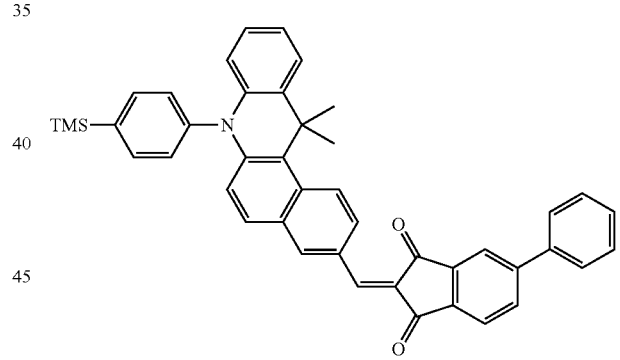
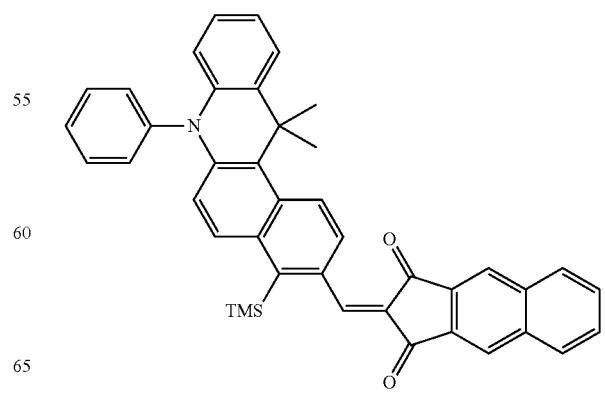

-continued
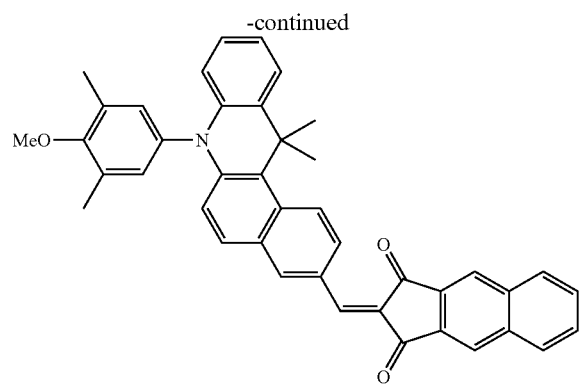
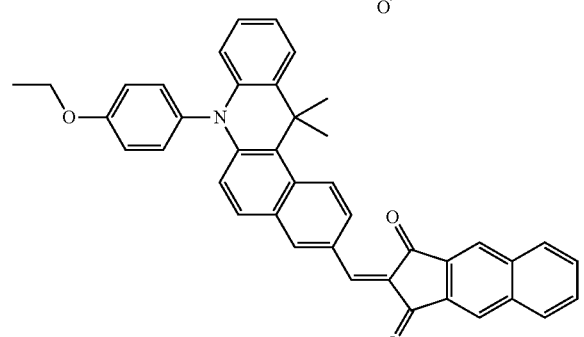
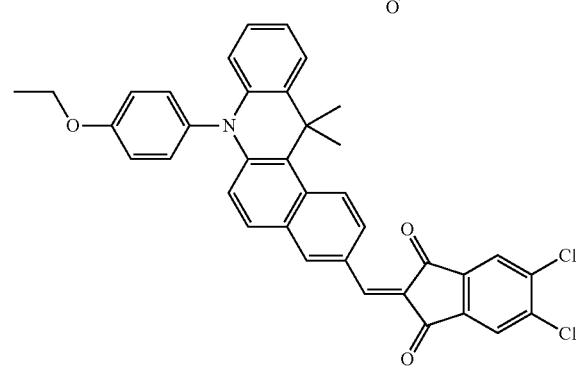
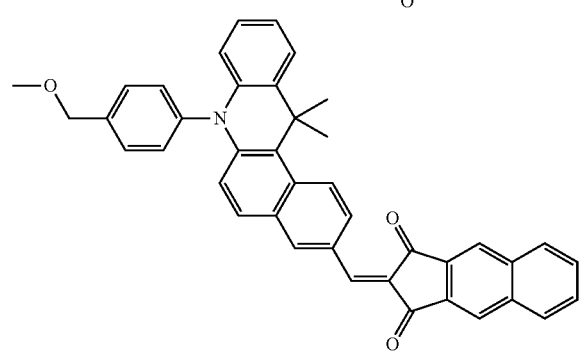
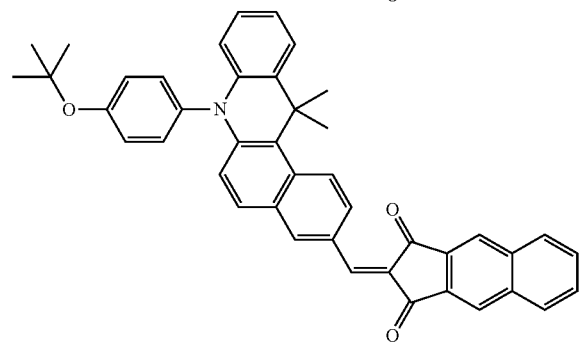
-continued
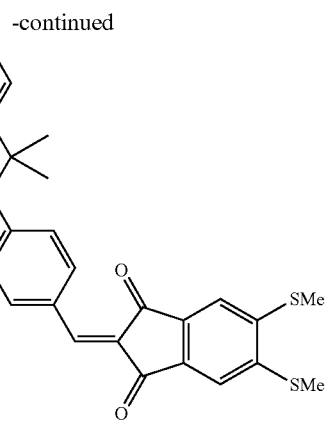
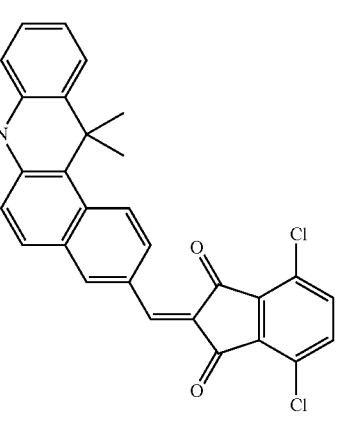

-continued
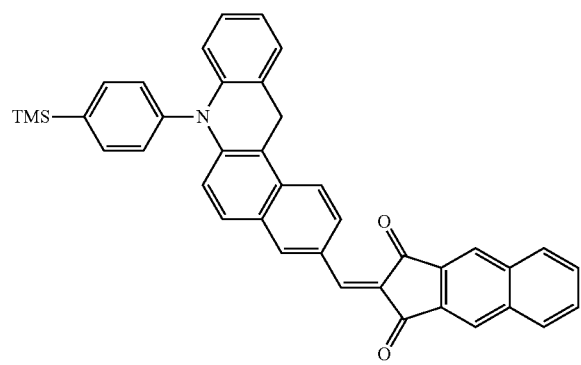
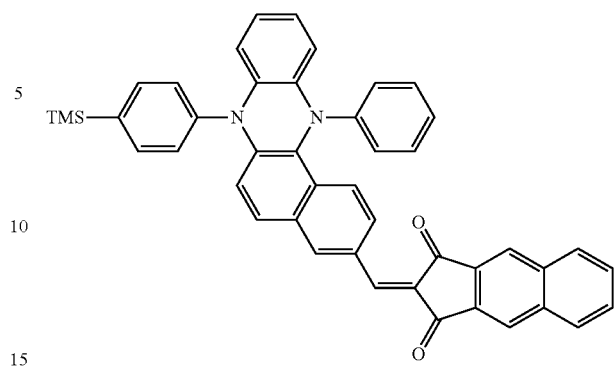
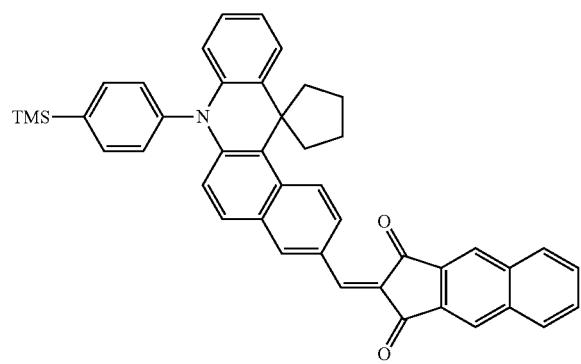
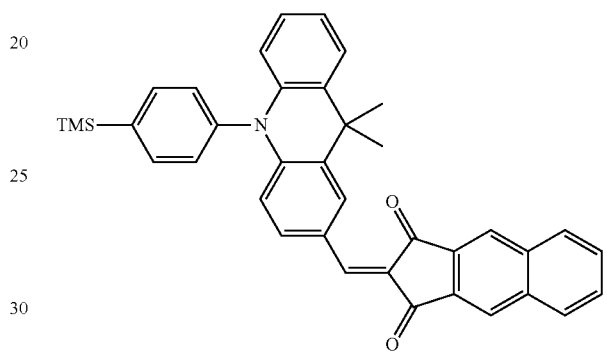
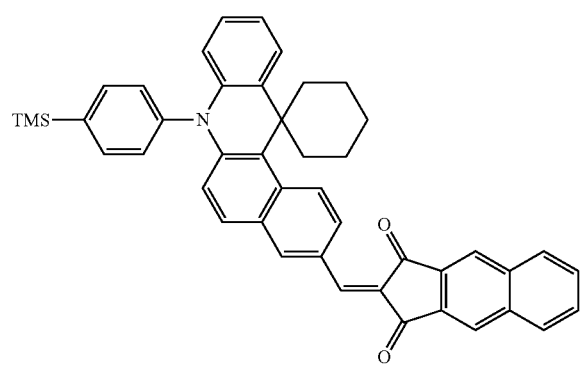
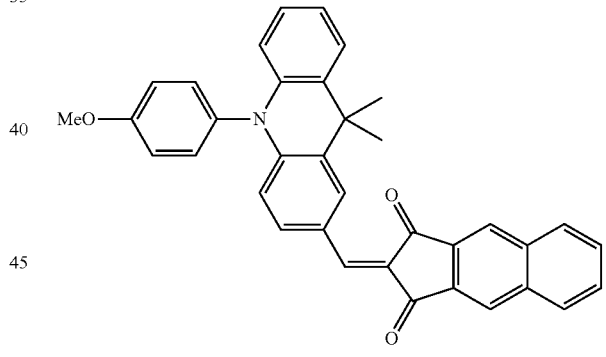
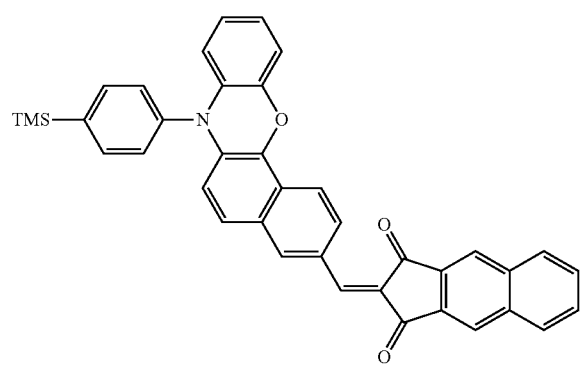
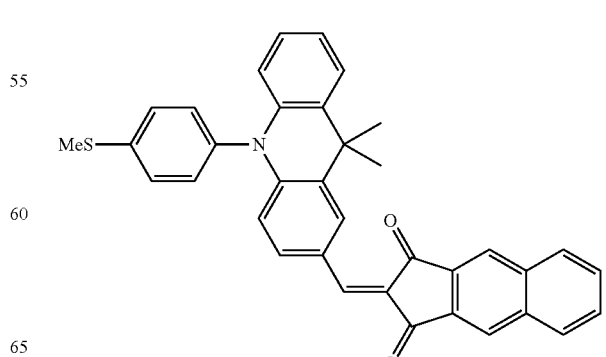

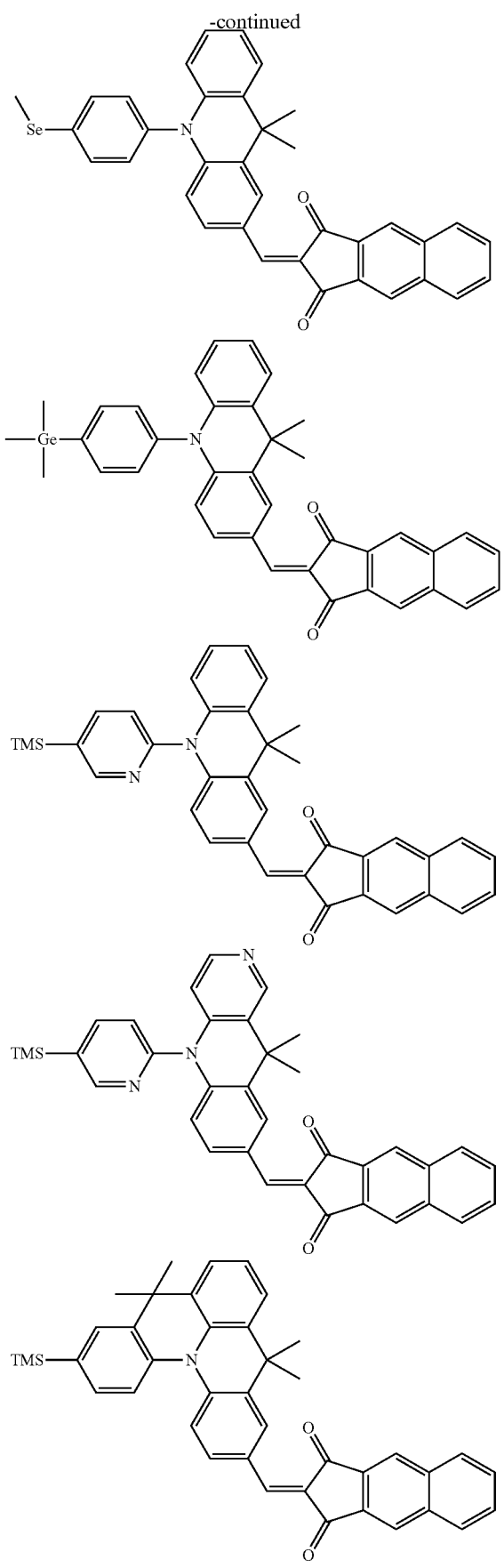
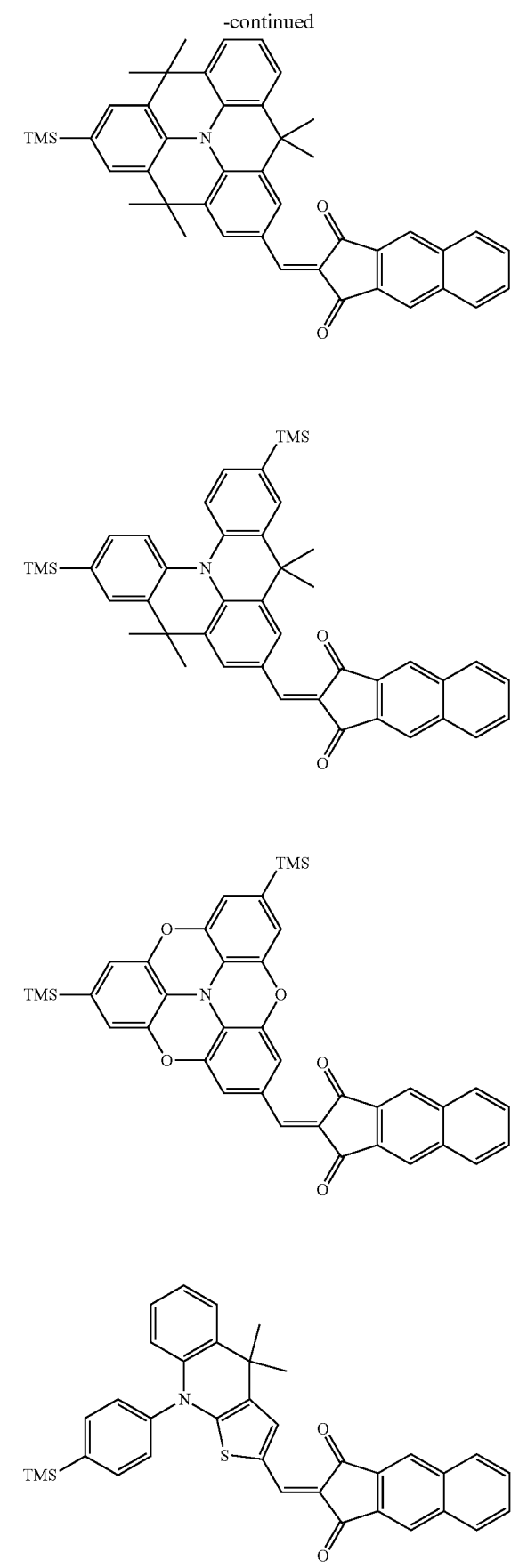

27
-continued
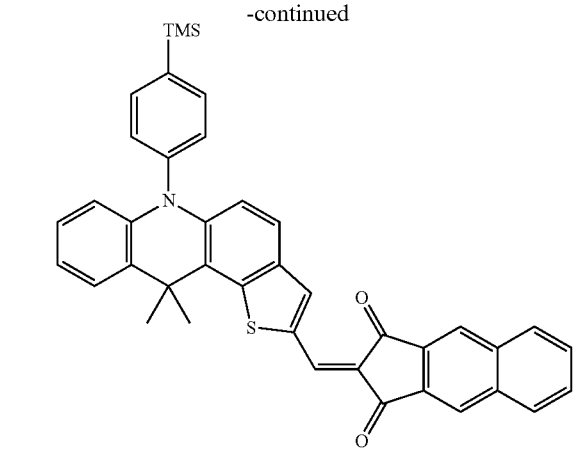
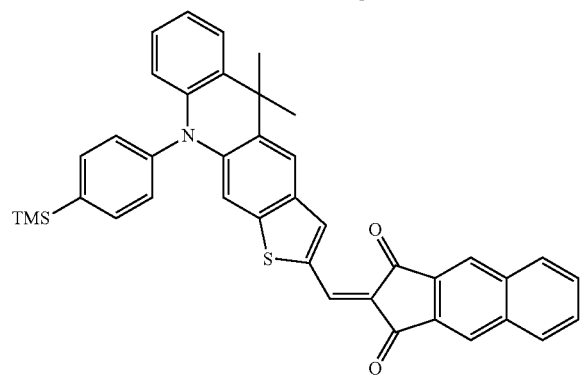
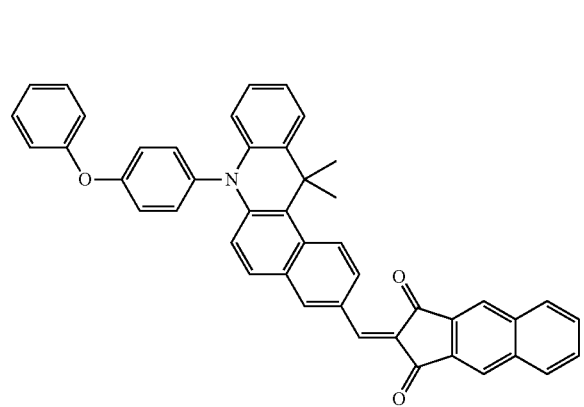
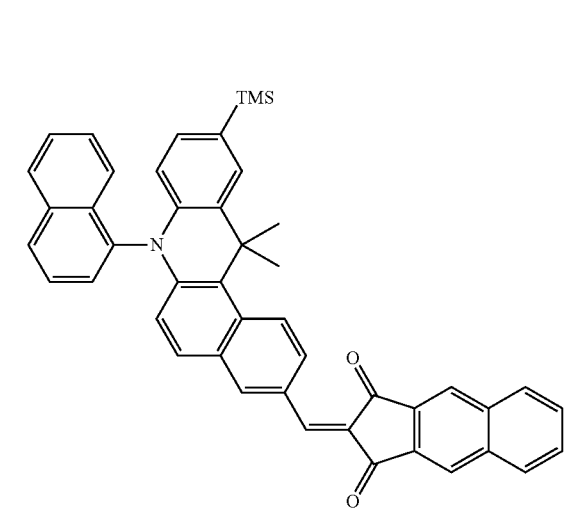
28
-continued
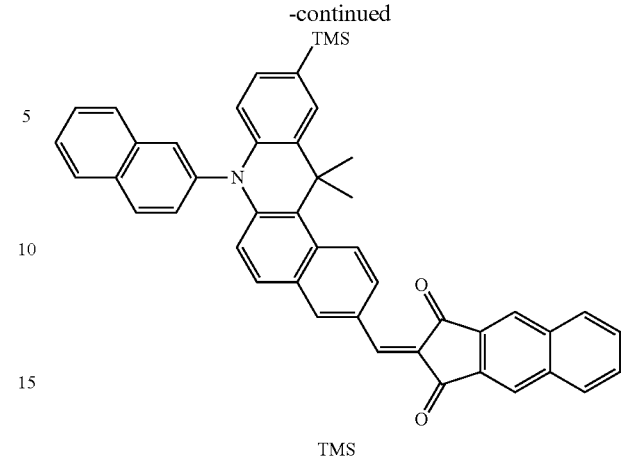
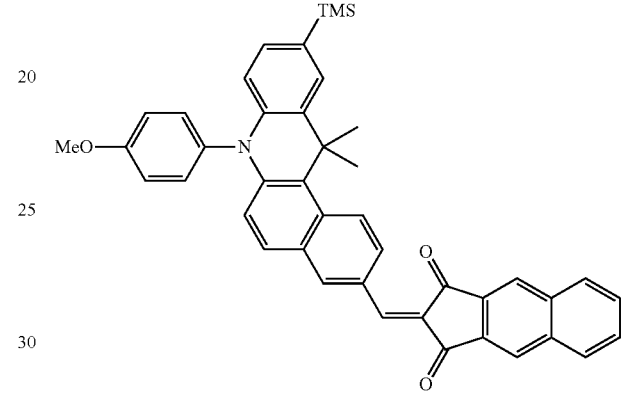
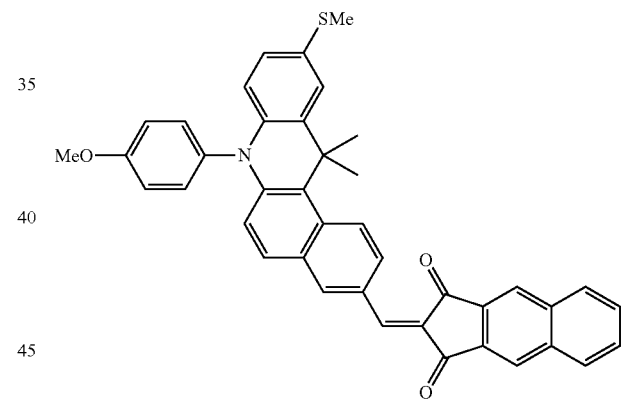
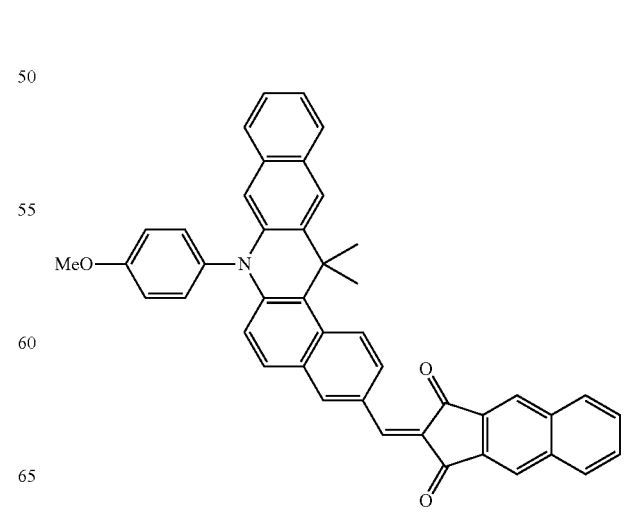

-continued

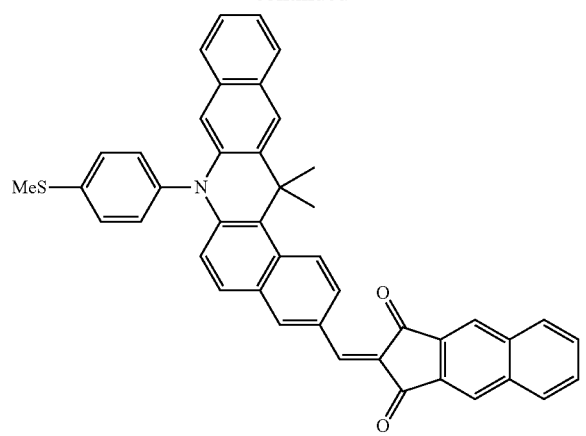
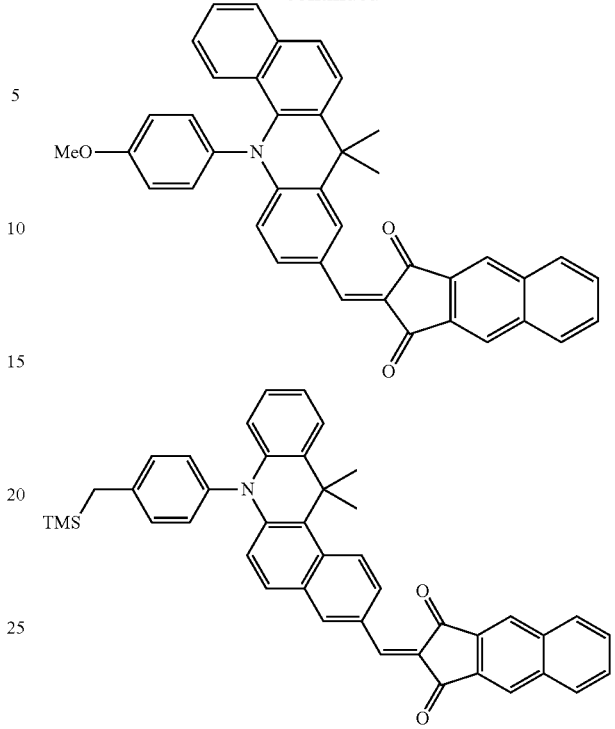
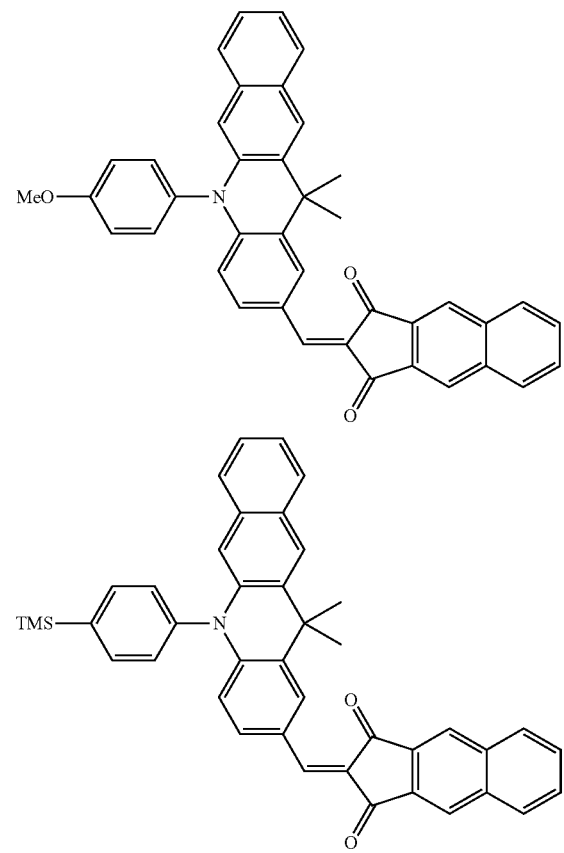

The ionization potential (hereinafter, may be abbreviated to IP) of the compound (A) is preferably 6.0 eV or less, more preferably 5.8 eV or less, and particularly preferably 5.6 eV or less. The ionization potential is preferably within this range since when an electrode and another material exist, transfer of electrons with the material is performed with a small electric resistance. The IP can be obtained using AC-2 manufactured by Riken Keiki Co., Ltd.

The compound (A) preferably has the absorption maximum in a wavelength region of 400 nm to less than 720 nm in the ultraviolet visible absorption spectrum, and the peak wavelength (absorption maximum wavelength) of the absorption spectrum is preferably 450 nm to 700 nm, more preferably 480 nm to 700 nm, and even more preferably 510 nm to 680 nm from the viewpoint of extensive absorption of light in a visible region.

The absorption maximum wavelength of the compound (A) can be measured using, for example, UV-2550 manufactured by Shimadzu Corporation with a chloroform solution of the compound (A). The concentration of the chloroform solution is preferably $5\times10^{-5}$ mol/l to $1\times10^{-7}$ mol/l, more preferably $3\times10^{-5}$ mol/l to $2\times10^{-6}$ mol/l, and particularly preferably $2\times10^{-5}$ mol/l to $5\times10^{-6}$ mol/l.

The compound (A) preferably has the absorption maximum in a wavelength region of 400 nm to less than 720 nm in the ultraviolet visible absorption spectrum, and the molar absorption coefficient of the absorption maximum wavelength is preferably 10,000 $mol^{-1} \cdot l \cdot cm^{-1}$ or greater. A material having a high molar absorption coefficient is preferred to reduce the film thickness of a photoelectric conversion film and to provide an element having high charge collection efficiency and high sensitivity characteristics. The molar absorption coefficient of the compound (A) is preferably 10,000 $mol^{-1} \cdot l \cdot cm^{-1}$ or greater, more preferably 30,000 $mol^{-1} \cdot l \cdot cm^{-1}$ or greater, and particularly preferably 50,000 $mol^{-1} \cdot l \cdot cm^{-1}$ or greater. The molar absorption coefficient of the compound (A) is measured with a chloroform solution.

The larger the difference (melting point-deposition temperature) between the melting point and the deposition temperature, the harder the compound (A) is to decompose upon deposition. The difference (melting point-deposition temperature) between the melting point and the deposition temperature is preferably 40° C. or greater, more preferably 50° C. or greater, and even more preferably 60° C. or greater.

The melting point of the compound (A) is preferably 240° C. or higher, more preferably 280° C. or higher, and even more preferably 300° C. or higher. The melting point is preferably 300° C. or higher since the decomposition before deposition is reduced, stable film formation can be performed, the decomposition product of the compound is relatively hardly generated, and thus the photoelectric conversion performance is hardly reduced.

The deposition temperature of the compound is a temperature at which a crucible is heated in a degree of vacuum of $4 \times 10^{-4}$ Pa or lower and a deposition speed reaches 3.0 angstroms/s ($3.0 \times 10^{-10}$ m/s).

The glass transition temperature (Tg) of the compound (A) is preferably 95° C. or higher, more preferably 110° C. or higher, even more preferably 135° C. or higher, particularly preferably 150° C. or higher, and most preferably 160° C. or higher.

The molecular weight of the compound (A) is preferably 300 to 1,500, more preferably 400 to 1,000, and particularly preferably 500 to 900. The deposition temperature can be reduced by reducing the molecular weight, and thus thermal decomposition of the compound upon deposition can be further prevented. In addition, necessary energy for deposition can be suppressed by reducing the deposition time. The deposition temperature of the compound (A) is preferably 400° C. or lower, more preferably 380° C. or lower, even more preferably 360° C. or lower, and most preferably 340° C. or lower.

It is desirable that the compound (A) is subjected to purification by sublimation before production of a photoelectric conversion element or an imaging element. Impurities and residual solvents contained before sublimation can be eliminated by purification by sublimation. As a result, the performance of the photoelectric conversion element or the imaging element can be stabilized. In addition, the deposition speed is easily kept constant.

The purity of the compound (A) before purification by sublimation is preferably 99% or greater, more preferably 99.5% or greater, and even more preferably 99.9% or greater in terms of high-performance liquid chromatography (HPLC). The content of remnants of a reaction solvent, a purification solvent, and the like used in the process for obtaining the compound (A) is preferably 3% or less, more preferably 1% or less, even more preferably 0.5% or less, and particularly preferably a detection limit or less. For the measurement of the content of the residual solvents (including moisture), $^1$H-NMR measurement, gas chromatography measurement, Karl Fischer measurement, or the like is used. By reducing the residual solvents by increasing the purity, thermal decomposition upon purification by sublimation can be suppressed.

The compound (A) is particularly useful as a photoelectric conversion material of a photoelectric conversion film which is used in an imaging element, an optical sensor, or a photoelectric cell. As other uses, it can also be used as a coloring material, a liquid crystal material, an organic semiconductor material, an organic light-emitting element material, a charge transporting material, a pharmaceutical material, a fluorescent diagnostic agent material, and the like.

[Photoelectric Conversion Element]

A photoelectric conversion element of the invention is provided with a conductive film, a photoelectric conversion film containing the above-described photoelectric conversion material (compound (A)), and a transparent conductive film in this order. Since the photoelectric conversion element of the invention contains the above-described photoelectric conversion material (compound (A)) of the invention, the performance of the element is thought to hardly change even when there are variations in the concentration of the photoelectric conversion material in the photoelectric conversion film.

The reason for this is not clear, but is presumed as follows.

As described above, in the photoelectric conversion material (compound (A)) of the invention, the triarylamine or the ring indicated by $Z_1$ has a specific substituent, and the triarylamine forms a ring. Therefore, it is thought that when the photoelectric conversion material is used in the photoelectric conversion film of the photoelectric conversion element, mutual aggregation of the molecules can be suppressed, but necessary overlapping (packing) between the molecules for transport of charges (holes or electrons) can be maintained. The reason why the overlapping between the molecules can be maintained is thought to be that the C—Si bond distance or the C—Ge bond distance is longer than the C—C bond distance, or to be a difference in the steric hindrance due to a difference in the direct bond between an oxygen atom, a sulfur atom, or a selenium atom and a carbon atom. As a result, it is thought that even when there are variations (some changes) in the concentration of the photoelectric conversion material in the photoelectric conversion film, the aggregation and the packing between the molecules hardly change, and the performance of the element such as responsiveness and photoelectric conversion efficiency hardly changes (is maintained at a high level). This is also presumed from the fact that as shown in comparative examples to be described later, when the triarylamine forms a ring, but the triarylamine or the ring indicated by $Z_1$ has no specific substituent (Comparative Examples 2-3 to 2-5), or when the triarylamine or the ring indicated by $Z_1$ has a specific substituent, but the triarylamine does not form a ring (Comparative Examples 2-1 and 2-2), the change in the performance of the element due to variations in the concentration of the photoelectric conversion material is large, or the level of the performance of the element becomes insufficient even when the change in the performance of the element is small.

FIG. 1 shows schematic cross-sectional views each showing an embodiment of the photoelectric conversion element of the invention.

A photoelectric conversion element 10a shown in FIG. 1(a) has a configuration in which a conductive film (hereinafter, also written as lower electrode) 11 functioning as a lower electrode, an electron blocking layer 16A formed on the lower electrode 11, a photoelectric conversion film 12 formed on the electron blocking layer 16A, and a transparent conductive film (hereinafter, also written as upper electrode) 15 functioning as an upper electrode are laminated in this order.

Figure 1B:
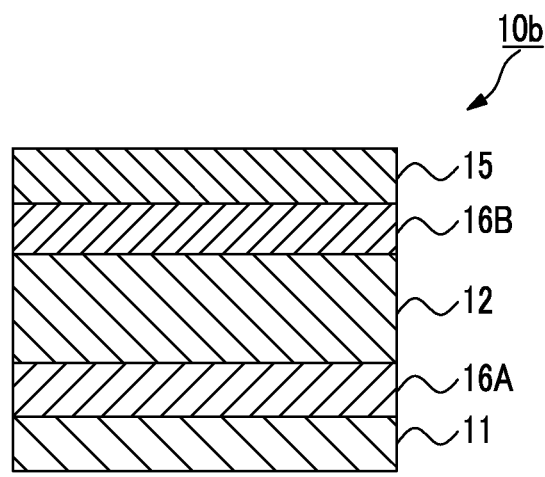

FIG. 1(b) shows another example of the configuration of the photoelectric conversion element. A photoelectric conversion element 10b shown in FIG. 1(b) has a configuration in which an electron blocking layer 16A, a photoelectric conversion film 12, a hole blocking layer 16B, and an upper electrode 15 are laminated in this order on a lower electrode 11. The lamination order of the electron blocking layer 16A, the photoelectric conversion film 12, and the hole blocking layer 16B in FIGS. 1(a) and 1(b) may be reversed according to the uses and characteristics.

In the configuration of the photoelectric conversion element 10a (10b), light preferably enters the photoelectric conversion film 12 via the transparent conductive film 15.

In addition, when the photoelectric conversion element 10a (10b) is used, an electric field can be applied. In this case, the conductive film 11 and the transparent conductive film 15 form a pair of electrodes, and to the pair of electrodes, an electric field of $1 \times 10^{-5}$ to $1 \times 10^7$ V/cm is preferably applied, and an electric field of $1 \times 10^{-4}$ to $1 \times 10^7$ V/cm is more preferably applied. From the viewpoint of performance and power consumption, an electric field of $1 \times 10^{-4}$ to $1 \times 10^6$ V/cm is preferably applied, and an electric field of $1 \times 10^{-3}$ to $5 \times 10^5$ V/cm is more preferably applied.

Regarding a method of applying a voltage, in FIGS. 1(a) and 1(b), it is preferable that the application is performed such that the side of the electron blocking layer 16A becomes a cathode and the side of the photoelectric conversion film 12 becomes an anode. When the photoelectric conversion element 10a (10b) is used as an optical sensor, or incorporated into an imaging element, the application of a voltage can also be performed in the same manner.

Hereinafter, aspects of the respective layers (photoelectric conversion layer, lower electrode, upper electrode, electron blocking layer, hole blocking layer, and the like) constituting the photoelectric conversion element 10a (10b) will be described in detail.

First, the photoelectric conversion film will be described in detail.

<Photoelectric Conversion Film>

The photoelectric conversion film contains the above-described photoelectric conversion material (compound (A)) of the invention.

The compound (A) is as described above.

(Other Materials)

The photoelectric conversion film may further contain a p-type organic semiconductor (compound) or an n-type organic semiconductor (compound).

The p-type organic semiconductor (compound) is a donor-type organic semiconductor (compound), and is an organic compound mainly represented by a hole transporting organic compound and having properties of easily donating electrons. More specifically, the p-type organic semiconductor (compound) is an organic compound having a lower ionization potential when two organic materials are used in contact with each other. Accordingly, the donor-type organic compound may be any organic compound as long as it is an electron-donating organic compound. For example, a triarylamine compound, a benzidine compound, a pyrazoline compound, a styrylamine compound, a hydrazone compound, a triphenylmethane compound, a carbazole compound, and the like can be used.

The n-type organic semiconductor (compound) is an acceptor-type organic semiconductor, and is an organic compound mainly represented by a hole transporting organic compound and having properties of easily accepting electrons. More specifically, the n-type organic semiconductor (compound) is an organic compound having a higher electron affinity when two organic compounds are used in contact with each other. Accordingly, the acceptor-type organic semiconductor may be any organic compound as long as it is an electron-accepting organic compound. Examples thereof include fullerenes selected from the group consisting of fullerenes and derivatives thereof, a condensed aromatic carbocyclic compound (naphthalene derivative, anthracene derivative, phenanthrene derivative, tetracene derivative, pyrene derivative, perylene derivative, and fluoranthene derivative), a heterocyclic compound containing a nitrogen atom, an oxygen atom, and a sulfur atom (for example, pyridine, pyrazine, pyrimidine, pyridazine, triazine, quinoline, quinoxaline, quinazoline, phthalazine, cinnoline, isoquinoline, pteridine, acridine, phenazine, phenanthroline, tetrazole, pyrazole, imidazole, thiazole, oxazole, indazole, benzimidazole, benzotriazole, benzoxazole, benzothiazole, carbazole, purine, triazolopyridazine, triazolopyrimidine, tetrazaindene, oxadiazole, imidazopyridine, pyralidine, pyrrolopyridine, thiadiazolopyridine, dibenzazepine, tribenzazepine, and the like), a polyarylene compound, a fluorene compound, a cyclopentadiene compound, a silyl compound, and a metal complex having a nitrogen-containing heterocyclic compound as a ligand.

As the n-type organic semiconductor (compound), fullerenes selected from the group consisting of fullerenes and derivatives thereof are preferred. The fullerene indicates fullerene $C_{60}$, fullerene $C_{70}$, fullerene $C_{76}$, fullerene $C_{78}$, fullerene $C_{80}$, fullerene $C_{82}$, fullerene $C_{84}$, fullerene $C_{90}$, fullerene $C_{96}$, fullerene $C_{240}$, fullerene $C_{540}$, and a mixed fullerene, and the derivatives thereof (fullerene derivatives) indicate compounds formed by adding a substituent to such fullerenes. As the substituent, an alkyl group, an aryl group, or a heterocyclic group is preferred. As the fullerene derivative, compounds described in JP2007-123707A are preferred.

The photoelectric conversion film preferably has a bulk hetero structure which is formed in a state in which the photoelectric conversion material (compound (A)) of the invention and the fullerenes are mixed. The bulk hetero structure is a film in which the photoelectric conversion material (compound (A)) of the invention and the n-type organic compound are mixed and dispersed in the photoelectric conversion film, and can be formed by either a wet method or a dry method. However, it is preferably formed by a co-deposition method. By including the bulk hetero structure, a disadvantage in that a carrier diffusion length of the photoelectric conversion film is short is compensated, and thus the photoelectric conversion efficiency of the photoelectric conversion film can be improved. The bulk heterojunction structure is described in detail in paragraphs "0013" and "0014" of JP2005-303266A.

From the viewpoint of responsiveness of the photoelectric conversion element, the content of the fullerenes with respect to the total content of the photoelectric conversion material (compound (A)) of the invention and the fullerenes (=film thickness of fullerenes in terms of single layer/(film thickness of photoelectric conversion material (compound (A)) of the invention in terms of single layer+film thickness of fullerenes in terms of single layer)) is preferably 50 vol % or greater, more preferably 55 vol % or greater, and even more preferably 65 vol % or greater. The upper limit is not particularly limited, but is preferably 95 vol % or less, and more preferably 90 vol % or less.

The photoelectric conversion film (the n-type organic compound may be mixed therein) containing the photoelectric conversion material (compound (A)) of the invention is a non-light-emitting film, and has characteristics different from those of an organic electroluminescent element (OLED). The non-light-emitting film is a film having luminescent quantum efficiency of 1% or lower, and the luminescent quantum efficiency is more preferably 0.5% or lower, and even more preferably 0.1% or lower.

(Film Forming Method)

The photoelectric conversion film can be formed using a dry film forming method or a wet film forming method.

Specific examples of the dry film forming method include physical vapor deposition methods such as a vacuum deposition method, a sputtering method, an ion plating method, and a MBE method, a CVD method such as plasma polymerization, and the like. As the wet film forming method, a casting method, a spin coating method, a dipping method, or an LB method can be used. The dry film forming method is preferred, and the vacuum deposition method is more preferred. When the film is formed through the vacuum deposition method, the manufacturing conditions such as the degree of vacuum and the deposition temperature can be set according to a normal method.

The thickness of the photoelectric conversion film is preferably 10 nm to 1,000 nm, more preferably 50 nm to 800 nm, and particularly preferably 100 nm to 500 nm.

<Electrode>

The electrodes (upper electrode (transparent conductive film) and lower electrode (conductive film)) are made from a conductive material. As the conductive material, a metal, an alloy, a metal oxide, an electroconductive compound, or a mixture thereof can be used.

When light enters the photoelectric conversion film via the transparent conductive film, the upper electrode is preferably sufficiently transparent with respect to the light to be detected. Specific examples thereof include conductive metal oxides such as a tin oxide (ATO or FTO) doped with antimony, fluorine, or the like, a tin oxide, a zinc oxide, an indium oxide, an indium tin oxide (ITO), and an indium zinc oxide (IZO), thin metal films such as gold, silver, chromium, and nickel, mixtures or laminated bodies of these metals and conductive metal oxides, inorganic conductive substances such as copper iodide and copper sulfide, organic conductive materials such as polyaniline, polythiophene, and polypyrrole, laminated bodies of these materials and an ITO, and the like. Among these, transparent conductive metal oxides are preferred in view of high conductive properties and transparency.

When a transparent conductive film such as a TCO is used as the upper electrode, a DC short circuit or an increase in the leakage current may occur. One reason for this is thought to be that fine cracks introduced in the photoelectric conversion film are covered with a dense film such as a TCO, and thus conduction between the upper electrode and the lower electrode on the opposite side increases. Therefore, an increase in the leakage current hardly occurs in the case of an electrode such as aluminum whose film quality is relatively inferior. An increase in the leakage current can be greatly suppressed by controlling the film thickness of the upper electrode with respect to the film thickness (that is, depth of crack) of the photoelectric conversion film. It is desirable that the thickness of the upper electrode is ⅕ or less, and preferably 1/10 or less of the thickness of the photoelectric conversion film.

In general, when a conductive film is made thin such that its thickness is less than a certain range, this leads to a sudden increase in the resistance value, but in a solid imaging element in which the photoelectric conversion element according to this embodiment is incorporated, the sheet resistance may be preferably 100Ω/☐ to 10,000Ω/☐, and the degree of freedom of the range of the film thickness which can be reduced is high. In addition, the thinner the upper electrode (transparent conductive film), the smaller the amount of light to be absorbed, and thus light transmittance usually increases. The increase in the light transmittance is extremely preferred since the light absorption in the photoelectric conversion film is increased and the photoelectric conversion capability is thus increased. It is desirable that the film thickness of the upper electrode is preferably 5 nm to 100 nm, and more preferably 5 nm to 20 nm in consideration of the suppression of the leakage current, the increase in the resistance value of the thin film, and the increase in the transmittance associated with the reduction in the thickness of the film.

According to uses, the lower electrode may have transparency, or may use a material which has no transparency on the contrary and reflects light. Specific examples thereof include conductive metal oxides such as a tin oxide (ATO or FTO) doped with antimony, fluorine, or the like, a tin oxide, a zinc oxide, an indium oxide, an indium tin oxide (ITO), and an indium zinc oxide (IZO), metals such as gold, silver, chromium, nickel, titanium, tungsten, and aluminum, conductive compounds such as oxides or nitrides of these metals (for example, titanium nitride (TiN)), mixtures or laminated bodies of these metals and conductive metal oxides, inorganic conductive substances such as copper iodide and copper sulfide, organic conductive materials such as polyaniline, polythiophene, and polypyrrole, laminated bodies of these materials and an ITO or titanium nitride, and the like.

The method of forming the electrode is not particularly limited, and can be appropriately selected in consideration of adaptability with the material of the electrode. Specifically, the electrode can be formed by a wet method such as a printing method or a coating method, a physical method such as a vacuum deposition method, a sputtering method, or an ion plating method, a chemical method such as a CVD method or a plasma CVD method, or the like.

When the material of the electrode is an ITO, the electrode can be formed by a method such as an electron beam method, a sputtering method, a resistance heating deposition method, a chemical reaction method (sol-gel method or the like), or the application of a dispersion of an indium tin oxide. Furthermore, a UV-ozone treatment, a plasma treatment, or the like can be performed on the film produced using an ITO. When the material of the electrode is a TiN, various methods including a reactive sputtering method can be used, and a UV-ozone treatment, a plasma treatment, or the like can be performed.

<Charge Blocking Layer: Electron Blocking Layer and Hole Blocking Layer>

The photoelectric conversion element of the invention may have a charge blocking layer. When the layer is provided, the photoelectric conversion element obtains more excellent characteristics (photoelectric conversion efficiency, response speed, and the like). Examples of the charge blocking layer include an electron blocking layer and a hole blocking layer. Hereinafter, the respective layers will be described in detail.

(Electron Blocking Layer)

An electron-donating organic material can be used in the electron blocking layer. Specifically, aromatic diamine compounds such as N,N'-bis(3-methylphenyl)-(1,1'-biphenyl)-4,4'-diamine (TPD) and 4,4'-bis[N-(naphthyl)-N-phenyl-amino]biphenyl(α-NPD), oxazole, oxadiazole, triazole, imidazole, imidazolone, a stilbene derivative, a pyrazoline derivative, tetrahydroimidazole, polyarylalkane, butadiene, 4,4',4"-tris(N-(3-methylphenyl)N-phenylamino)triphenylamine(m-MTDATA), porphyrin, porphyrin compounds such as tetraphenylporphyrin copper, phthalocyanine, copper phthalocyanine, and titanium phthalocyanine oxide, a triazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a silazane derivative, and the like can be used as a low-molecular material, and polymers such as phenylenevinylene, fluorene, carbazole, indole, pyrene, pyrrole, picoline, thiophene, acetylene, and diacetylene and derivatives thereof can be used as a polymer material. Any compound having sufficient hole transporting properties and electron blocking properties can be used even though the compound is not an electron-donating compound. From the viewpoint of suppression of a dark current, the difference between the electron affinity of the n-type semiconductor used in the photoelectric conversion film and the ionization potential of the material used in the electron blocking layer adjacent to the photoelectric conversion film is preferably 1 eV or greater. When fullerene ($C_{60}$) is used as the n-type semiconductor, the electron affinity of the fullerene ($C_{60}$) is 4.2 eV, and thus the ionization potential of the material used in the adjacent electron blocking layer is preferably 5.2 eV or greater. Specifically, compounds described in paragraphs "0083" to "0089" of JP2008-72090A, paragraphs "0049" to "0063" of JP2011-176259A, paragraphs "0121" to "0156" of JP2011-228614A, and paragraphs "0108" to "0156" of JP2011-228615A are preferred.

The electron blocking layer also preferably contains a compound expressed by the following Formula (EB-1). By using the compound, the response speed of the photoelectric conversion film to be obtained is increased, and the fluctuation in the response speed between manufacturing rods is further suppressed. In addition, it is possible to obtain a photoelectric conversion element in which the performance (response, sensitivity, and dark current) of the element as the photoelectric conversion element and higher heat resistance are balanced.

(EB-1)

In Formula (EB-1), each of $A_{11}$ and $A_{12}$ independently indicates a group expressed by the following General Formula (A-1) or (A-2). j indicates an integer of 0 or greater. k indicates 0 or 1.

When j is 0, $A_{11}$ and $A_{12}$ are directly connected to each other. When both of j and k are 0, a hydrogen atom or a substituent (for example, the above-described substituent W) is bonded to a direct bond of $A_{11}$.

$Ar_{EB}$ indicates an arylene group or a heteroarylene group. When j is an integer of 1 or greater and k is 0, a hydrogen atom or a substituent (for example, the above-described substituent W) is bonded to a direct bond of $Ar_{EB}$ at an end.

General Formula (A-1)

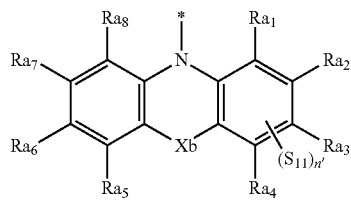

General Formula (A-2)

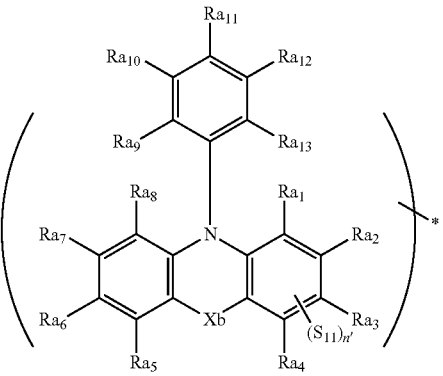

In General Formulae (A-1) and (A-2), each of $Ra_1$ to $Ra_{13}$ independently indicates a hydrogen atom or a substituent. * indicates a bonding position with $Ar_{EB}$. $Ar_{EB}$ which is bonded to General Formula (A-2) is substituted as any one of $Ra_1$ to $Ra_{13}$ in General Formula (A-2). When j is 0 and k is 1 in Formula (EB-1), * in General Formula (A-1) indicates a bonding position with General Formula (A-2), * in General Formula (A-2) indicates a bonding position with General Formula (A-1), and General Formula (A-1) is substituted as any one of $Ra_1$ to $Ra_{13}$ in General Formula (A-2).

Xb indicates a single bond, an oxygen atom, a sulfur atom, an alkylene group, a silylene group, an alkenylene group, a cycloalkylene group, a cycloalkenylene group, an arylene group, a divalent heterocyclic group, or $-NR_a-$. $R_a$ indicates a hydrogen atom or a substituent (for example, the above-described substituent W). Xb may further have a substituent (for example, the above-described substituent W).

$S_{11}$ indicates the following substituent ($S_{11}$), and is substituted as any one of $Ra_1$ to $Ra_{13}$. n' indicates an integer of 0 to 4. A plurality of $S_{11}$s existing when n' is an integer of 2 or greater may be the same as or different from each other.

In General Formula (A-2), $Ra_1$ and $Ra_{13}$; or $Ra_8$ and $Ra_9$ may be bonded to each other via a single bond, an oxygen atom, a sulfur atom, an alkylene group, a silylene group, an alkenylene group, a cycloalkylene group, a cycloalkenylene group, an arylene group, a divalent heterocyclic group, or $-NR_a-$. Here, $R_a$ indicates a hydrogen atom or a substituent. When $Ra_1$ and $Ra_{13}$; or $Ra_8$ and $Ra_9$ are bonded to each other via a single bond, an oxygen atom, a sulfur atom, an alkylene group, a silylene group, an alkenylene group, a cycloalkylene group, a cycloalkenylene group, an arylene group, a divalent heterocyclic group, or $-NR_a-$, $Ra_1$, $Ra_{13}$, $Ra_8$, or $Ra_9$ to be bonded may be a direct bond.

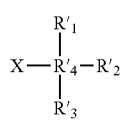

Substituent ($S_{11}$)

Here, each of $R'_1$ to $R'_3$ independently indicates a hydrogen atom or an alkyl group. $R'_4$ indicates a carbon atom or a silicon atom. X indicates a bonding position.

In General Formulae (A-1) and (A-2), each of $Ra_1$ to $Ra_{13}$ independently indicates a hydrogen atom or a substituent.

Each of $Ra_1$ to $Ra_{13}$ is preferably a hydrogen atom, a halogen atom, an alkyl group having 1 to 18 carbon atoms, an alkoxy group having 1 to 18 carbon atoms, an aryl group having 6 to 18 carbon atoms, a heterocyclic group having 4 to 16 carbon atoms, or a silyl group substituted with an aryl group, more preferably a hydrogen atom, an alkyl group having 1 to 12 carbon atoms, an alkoxy group having 1 to 12 carbon atoms, an aryl group having 6 to 14 carbon atoms, an alkyl group having 1 to 13 carbon atoms, or a silyl group substituted with an aryl group. And even more preferably a hydrogen atom, an alkyl group having 1 to 6 carbon atoms, or an aryl group having 6 to 10 carbon atoms. The alkyl group may have a branch. $Ra_1$ to $Ra_{13}$ may further have a substituent (for example, the above-described substituent W). When the substituent is more than one, the plurality of substituents may be bonded to each other to form a ring.

Specific preferred examples of $Ra_1$ to $Ra_{13}$ include a hydrogen atom, a methyl group, an ethyl group, a propyl group, a butyl group, a hexyl group, a cyclohexyl group, a methoxy group, a butoxy group, a phenyl group, a naphthyl group, a trimethylsilyl group, and the like.

In addition, each of $Ra_3$ and $Ra_6$ is a hydrogen atom or an alkyl group having 1 to 6 carbon atoms, and each of $Ra_1$, $Ra_2$, $Ra_4$, $Ra_5$, $Ra_7$, and $Ra_8$ is particularly preferably a hydrogen atom.

In General Formulae (A-1) and (A-2), Xb indicates a single bond, an oxygen atom, a sulfur atom, an alkylene group, a silylene group, an alkenylene group, a cycloalkylene group, a cycloalkenylene group, an arylene group, a divalent heterocyclic group, or —$NR_a$—. $R_a$ indicates a hydrogen atom or a substituent (for example, the above-described substituent W). Xb is preferably a single bond, an alkylene group having 1 to 13 carbon atoms, an alkenylene group having 2 to 12 carbon atoms, an arylene group having 6 to 14 carbon atoms, a heterocyclic group having 4 to 13 carbon atoms, an oxygen atom, a sulfur atom, or a silylene group, more preferably a single bond, an oxygen atom, an alkylene group having 1 to 6 carbon atoms (for example, methylene group, 1,2-ethylene group, or 1,1-dimethylmethylene group), an alkenylene group having 2 carbon atoms (for example, —$CH_2$=$CH_2$—), an arylene group having 6 to 10 carbon atoms (for example, 1,2-phenylene group or 2,3-naphthylene group), or a silylene group, and even more preferably a single bond, an oxygen atom, or an alkylene group having 1 to 6 carbon atoms (for example, methylene group, 1,2-ethylene group, or 1,1-dimethylmethylene group). Xb may further have a substituent (for example, the above-described substituent W).

Specific examples of the group expressed by General Formula (A-1) include groups exemplified by the following N-1 to N-16, but are not limited thereto. As the group expressed by General Formula (A-1), N-1 to N-7 and N-12 to N-16 are preferred, N-1 to N-6, N-12, N-14, and N-16 are more preferred, N-1 to N-3, N-12, and N-16 are even more preferred, N-1, N-2, and N-12 are particularly preferred, and N-1 is most preferred.

N-1

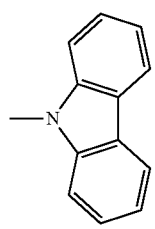

N-2

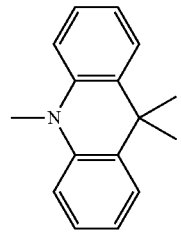

N-3

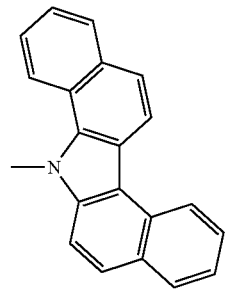

N-4

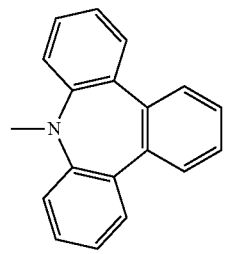

N-5

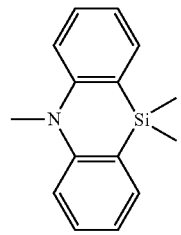

N-6

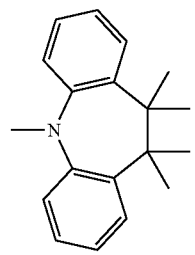

N-7

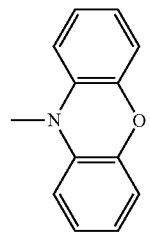

N-8 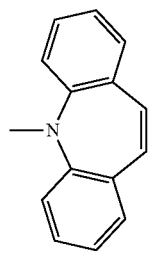
N-9 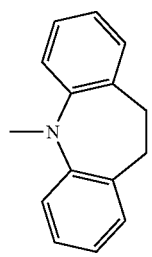
N-10 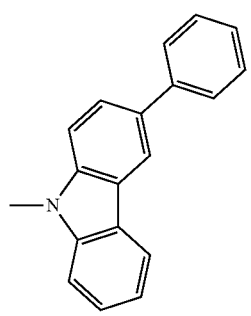
N-11 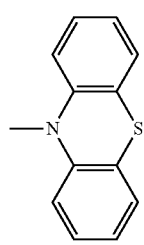
N-12 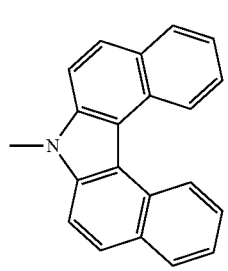
N-13 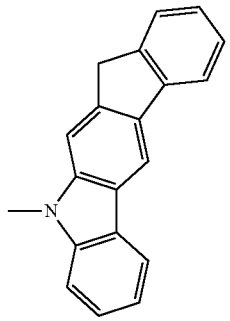
N-14 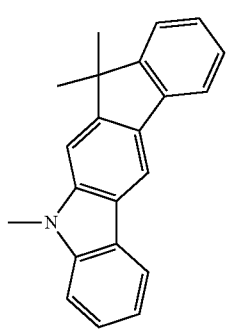
N-15 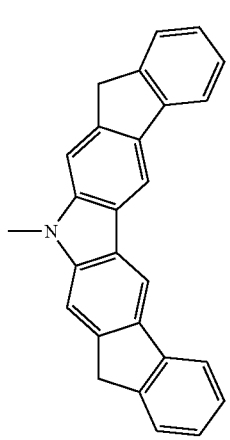
N-16 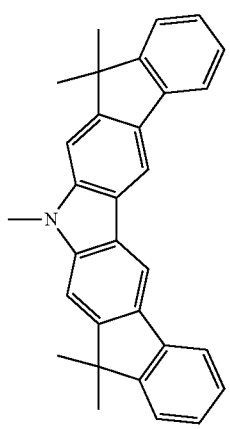
Specific examples of the group expressed by General Formula (A-2) include groups exemplified by the following N-20 to N-25, but are not limited thereto. The group expressed by General Formula (A-2) is preferably N-20, N-21, N-23, or N-25, more preferably N-20, N-23, or N-25, and particularly preferably N-20 or N-23.

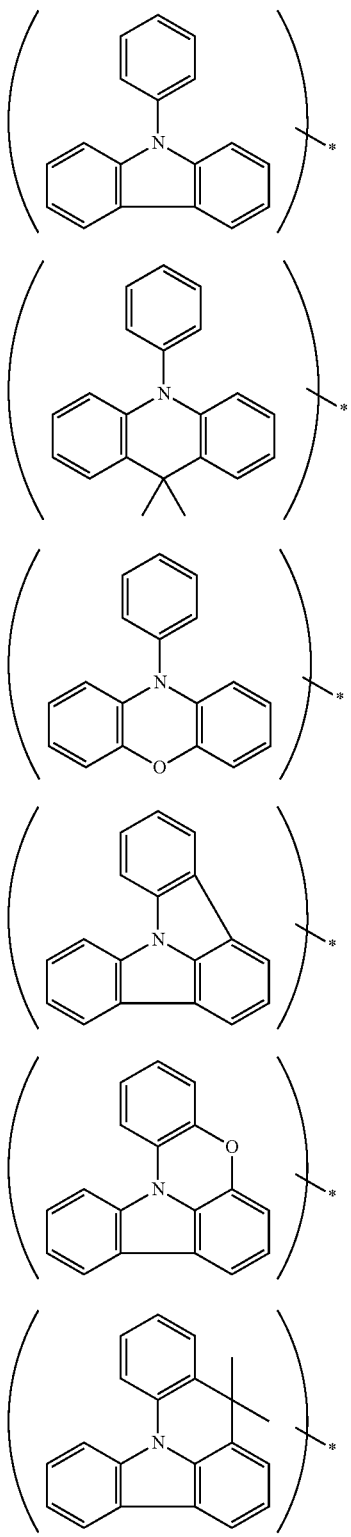

In the substituent ($S_{11}$), $R'_1$ indicates a hydrogen atom or an alkyl group. $R'_1$ is preferably a methyl group, an ethyl group, a propyl group, an iso-propyl group, a butyl group, or a tert-butyl group, more preferably a methyl group, an ethyl group, a propyl group, an iso-propyl group, or a tert-butyl group, even more preferably a methyl group, an ethyl group, an iso-propyl group, or a tert-butyl group, and particularly preferably a methyl group, an ethyl group, or a tert-butyl group.

$R'_2$ indicates a hydrogen atom or an alkyl group. $R'_2$ is preferably a hydrogen atom, a methyl group, an ethyl group, a propyl group, an iso-propyl group, a butyl group, or a tert-butyl group, more preferably a hydrogen atom, a methyl group, an ethyl group, or a propyl group, even more preferably a hydrogen atom or a methyl group, and particularly preferably a methyl group.

$R'_3$ indicates a hydrogen atom or an alkyl group. $R'_3$ is preferably a hydrogen atom or a methyl group, and more preferably a methyl group.

$R'_4$ indicates a carbon atom or a silicon atom, and is preferably a carbon atom.

In addition, $R'_1$ to $R'_3$ may be bonded to each other to form a ring. When a ring is formed, the number of membered rings is not particularly limited, but a five-membered ring or a six-membered ring is preferred, and a six-membered ring is more preferred.

In General Formulae (A-1) and (A-2), $S_{11}$ indicates the substituent ($S_{11}$), and is substituted as any one of $Ra_1$ to $Ra_{13}$. At least one of $Ra_3$ and $Ra_6$ in General Formula (A-1) or (A-2) preferably independently indicates the substituent ($S_{11}$).

As the substituent ($S_{11}$), the following (a) to (x) and (Si-1) to (Si-4) are preferred, (a) to (j) and (Si-1) to (Si-4) are more preferred, (a) to (h) and (Si-1) are even more preferred, (a) to (f) and (Si-1) are particularly preferred, (a) to (d) and (Si-1) are still more preferred, and (a) is most preferred.

(a)

(b)

(c)

(d)

(e)

(f)

(g)

-continued

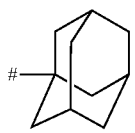 (h)

 (i)

(j)

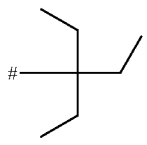 (k)

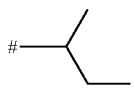 (l)

(m)

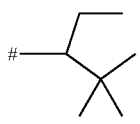 (n)

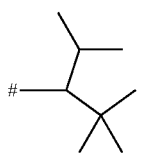 (o)

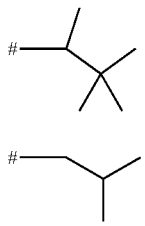 (p)

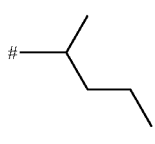 (q)

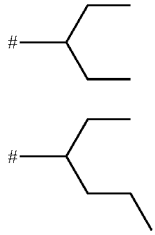 (r)

(s)

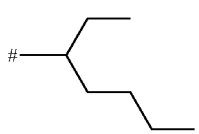 (t)

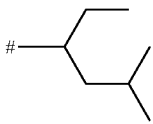 (u)

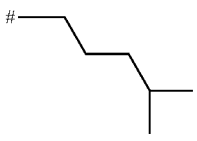 (v)

 (w)

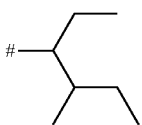 (x)

 (Si-1)

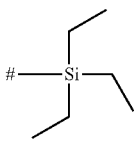 (Si-2)

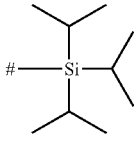 (Si-3)

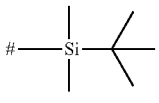 (Si-4)

When $Ar_{EB}$ is an arylene group, $Ar_{EB}$ is preferably an arylene group having 6 to 30 carbon atoms, and more preferably an arylene group having 6 to 20 carbon atoms. Specific examples of the ring constituting the arylene group include a benzene ring, a naphthalene ring, an anthracene ring, a phenanthrene ring, a fluorene ring, a triphenylene ring, a naphthacene ring, a pyrene ring, a biphenyl ring (two phenyl groups may be connected in an arbitrary connecting manner), a terphenyl ring (three benzene rings may be connected in an arbitrary connecting manner), and the like. The ring may be a combination thereof, and is preferably a fluorene ring, a naphthalene ring, an anthracene ring, a phenanthrene ring, or a pyrene ring, more preferably a fluorene ring, an anthracene ring, or a pyrene ring, and even more preferably a fluorene ring or a pyrene ring.

When $Ar_{EB}$ is a heteroarylene group, $Ar_{EB}$ is preferably a heteroarylene group composed of a five-, six-, or seven-membered ring, or a condensed ring thereof. Examples of the hetero atom contained in the heteroarylene group include an oxygen atom, a sulfur atom, a nitrogen atom, and the like. Specific examples of the ring constituting the heteroarylene group include a furan ring, a thiophene ring, a pyrrole ring, a pyrroline ring, a pyrrolidine ring, an oxazole ring, an isoxazole ring, a thiazole ring, an isothiazole ring, an imidazole ring, an imidazoline ring, an imidazolidine ring, a pyrazole ring, a pyrazoline ring, a pyrazolidine ring, a triazole ring, a furazane ring, a tetrazole ring, a pyran ring, a thiin ring, a pyridine ring, a piperidine ring, an oxazine ring, a morpholine ring, a thiazine ring, a pyridazine ring, a pyrimidine ring, a pyrazine ring, a piperazine ring, a triazine ring, a benzofuran ring, an isobenzofuran ring, a benzothiophene ring, an indole ring, an indoline ring, an isoindole ring, a benzoxazole ring, a benzothiazole ring, an indazole ring, a benzimidazole ring, a quinoline ring, an isoquinoline ring, a cinnoline ring, a phthalazine ring, a quinazoline ring, a quinoxaline ring, a dibenzofuran ring, a dibenzothiophene ring, a carbazole ring, a xanthene ring, an acridine ring, a phenanthridine ring, a phenanthroline ring, a phenazine ring, a phenoxazine ring, a thianthrene ring, an indolizine ring, a quinolizine ring, a quinuclidine ring, a naphthyridine ring, a purine ring, a pteridine ring, and the like. Combinations thereof may also be included. Among these, a tricyclic or higher condensed ring is preferred, and a carbazole ring is more preferred.

j indicates an integer of 0 or greater, and is preferably an integer of 0 to 3, more preferably 1 or 2, and even more preferably 1 from the viewpoint of heat resistance and response performance of the photoelectric conversion element.

Formula (EB-1) is preferably a compound expressed by the following Formula (EB-2).

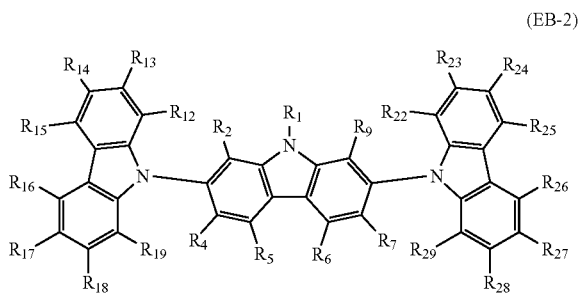

(EB-2)

In Formula (EB-2), $R_1$ indicates an aromatic hydrocarbon group or an aromatic heterocyclic group which may have a substituent. The total number of carbon atoms of the aromatic hydrocarbon structure and the aromatic heterocyclic structure included in $R_1$ is 6 to 30.

Each of $R_2$, $R_4$ to $R_7$, $R_9$, $R_{12}$ to $R_{19}$, and $R_{22}$ to $R_{29}$ independently indicates a hydrogen atom or a substituent.

In Formula (EB-2), $R_1$ indicates an aromatic hydrocarbon group or an aromatic heterocyclic group which may have a substituent.

As described above, the total number of carbon atoms of the aromatic hydrocarbon structure and the aromatic heterocyclic structure included in $R_1$ is 6 to 30. The total number of carbon atoms is more preferably 13 to 20, and even more preferably 15 to 18 from the viewpoint of the performance of the element and heat resistance. Since the total number of carbon atoms is 30 or less, the material expressed by Formula (EB-2) also has excellent deposition properties.

Specific examples of the ring constituting the aromatic hydrocarbon group indicated by $R_1$ include a benzene ring, a naphthalene ring, an anthracene ring, a phenanthrene ring, a fluorene ring, a triphenylene ring, a tetracene ring, a pyrene ring, and the like.

Specific examples of the ring constituting the aromatic heterocyclic group indicated by $R_1$ include a furan ring, a thiophene ring, a pyrrole ring, a pyrroline ring, a pyrrolidine ring, an oxazole ring, an isoxazole ring, a thiazole ring, an isothiazole ring, an imidazole ring, an imidazoline ring, an imidazolidine ring, a pyrazole ring, a pyrazoline ring, a pyrazolidine ring, a triazole ring, a furazane ring, a tetrazole ring, a pyran ring, a thiin ring, a pyridine ring, a piperidine ring, an oxazine ring, a morpholine ring, a thiazine ring, a pyridazine ring, a pyrimidine ring, a pyrazine ring, a piperazine ring, a triazine ring, a benzofuran ring, an isobenzofuran ring, a benzothiophene ring, a thienothiophene ring, an indole ring, an indoline ring, an isoindole ring, a benzoxazole ring, a benzothiazole ring, an indazole ring, a benzimidazole ring, a quinoline ring, an isoquinoline ring, a cinnoline ring, a phthalazine ring, a quinazoline ring, a quinoxaline ring, a dibenzofuran ring, a dibenzothiophene ring, a carbazole ring, a xanthene ring, an acridine ring, a phenanthridine ring, a phenanthroline ring, a phenazine ring, a phenoxazine ring, a thianthrene ring, an indolizine ring, a quinolizine ring, a quinuclidine ring, a naphthyridine ring, a purine ring, a pteridine ring, and the like.

Examples of the substituent include the above-described substituent W. When the aromatic hydrocarbon group or the aromatic heterocyclic group has a plurality of substituents, the plurality of substituents may be bonded to each other to form a ring.

The total number of carbon atoms (hereinafter, also referred to as total carbon number) of the aromatic hydrocarbon structure and the aromatic heterocyclic structure included in $R_1$ is 6 to 30. That is, the total number of carbon atoms constituting the aromatic hydrocarbon structure and the aromatic heterocyclic structure included in $R_1$ is 6 to 30.

When $R_1$ has a substituent, the number of carbon atoms of the aromatic hydrocarbon structure and the aromatic heterocyclic structure included in the substituent is also counted. The number of carbon atoms of structures such as an aliphatic hydrocarbon structure other than the aromatic hydrocarbon structure and the aromatic heterocyclic structure is not counted.

In Formula (1), each of $R_2$, $R_4$ to $R_7$, $R_9$, $R_{12}$ to $R_{19}$, and $R_{22}$ to $R_{29}$ independently indicates a hydrogen atom or a substituent. Examples of the substituent include the above-described substituent W, and the above-described substituent $S_{11}$ is more preferred. Preferred aspects of $S_{11}$ are the same as the above-described ranges.

The molecular weight of the compound expressed by Formula (EB-1) or (EB-2) is not particularly limited, but is preferably 500 to 2,000, more preferably 600 to 1500, and particularly preferably 700 to 1100.

The ionization potential (IP) of the compound expressed by Formula (EB-1) or (EB-2) is preferably less than the IP of a material having a role in the hole transport in the photoelectric conversion film in order to receive holes from the material having a role in the hole transport in the photoelectric conversion film without a hindrance. Particularly, when a material having such absorbing properties as to have sensitivity in a visible region is selected, the IP of a specific compound is preferably 5.8 eV or less for adaption to more materials. When the IP is 5.8 eV or less, an effect of exhibiting high charge collection efficiency is obtained without generation of a hindrance with respect to transport of charges.

The IP of the specific compound can be measured by ultraviolet photoelectron spectroscopy (UPS) or a photoelectron spectrometer in air (for example, AC-2 or the like manufactured by Riken Keiki co., Ltd.).

The IP of the compound expressed by Formula (EB-1) or (EB-2) can be controlled to be within the above range by changing a substituent bonded to the skeleton.
Hereinafter, specific examples of the electron blocking material will be shown, but the electron blocking material used in the invention is not limited thereto.
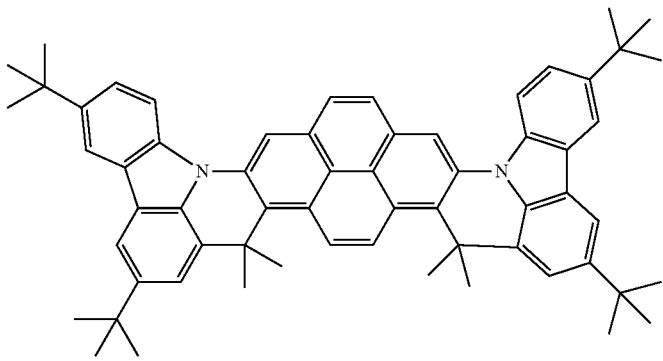
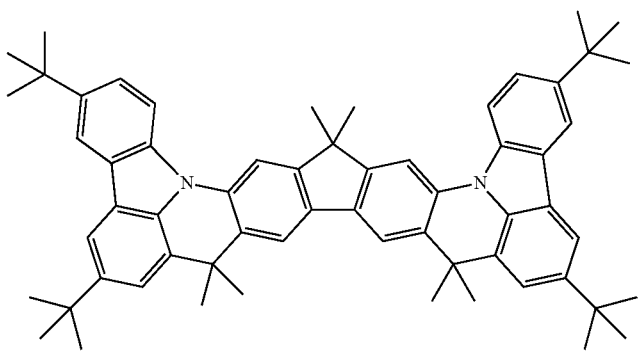
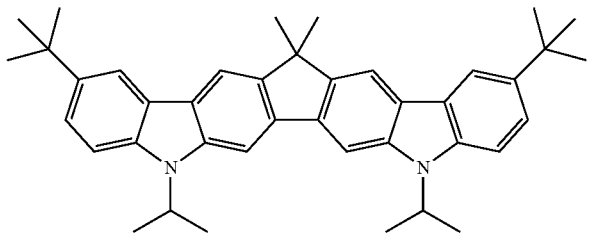
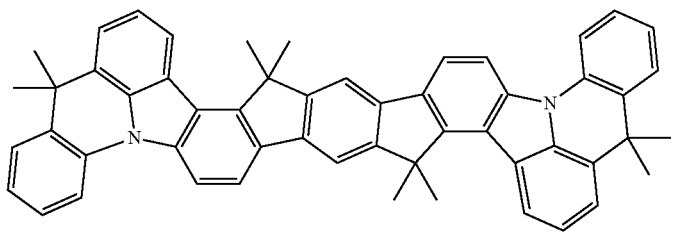
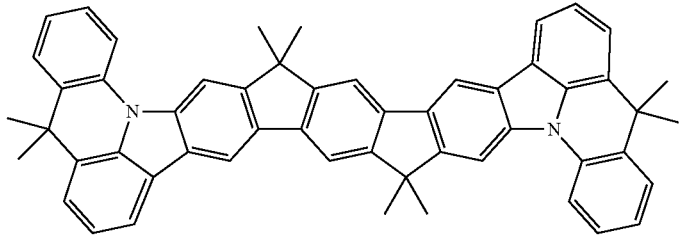

-continued
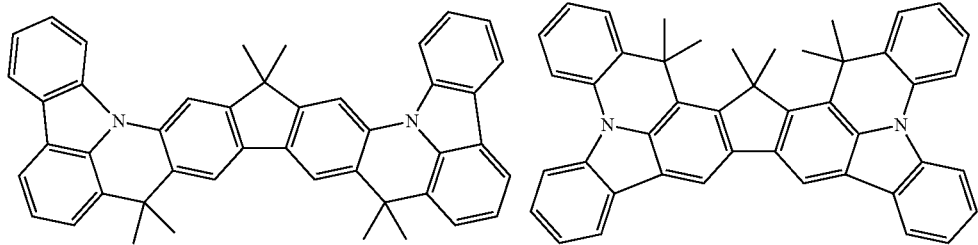
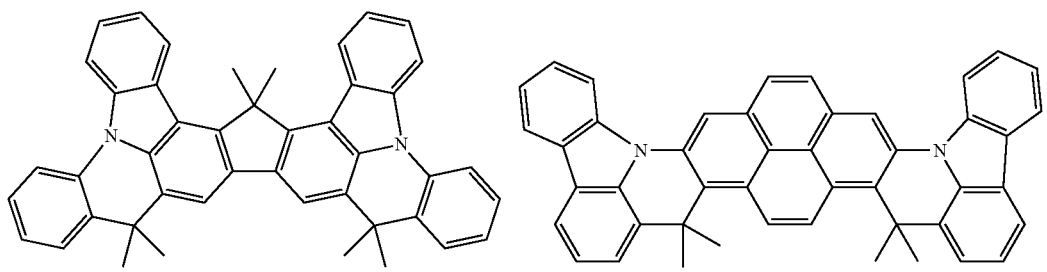
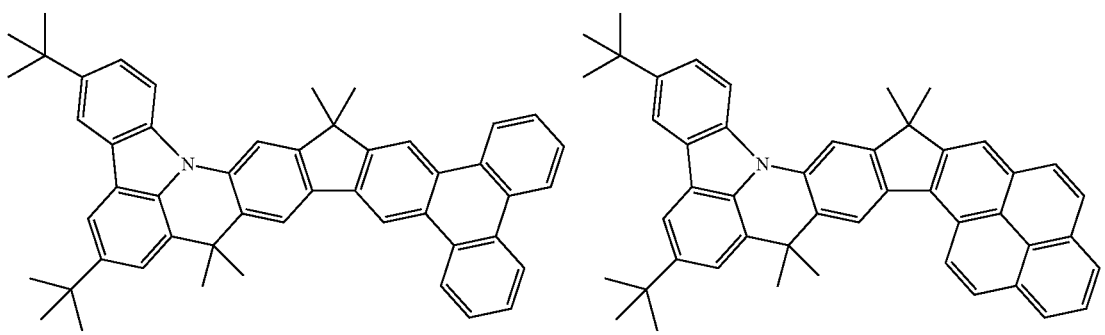
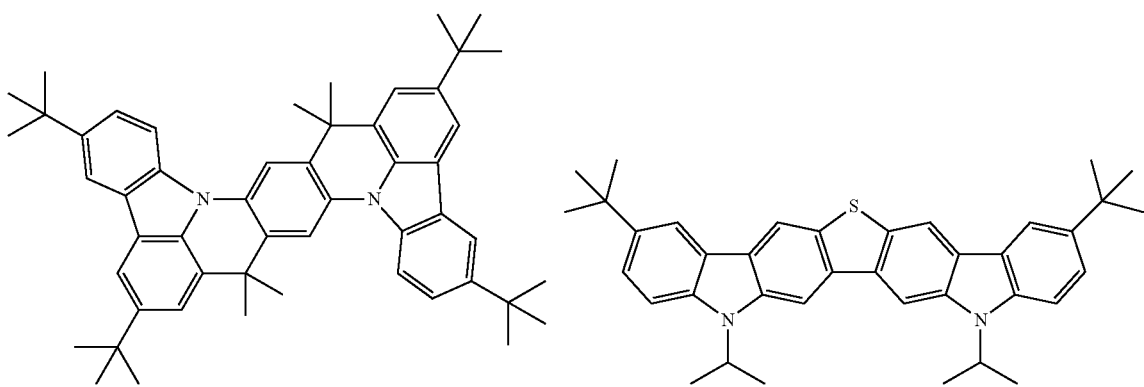
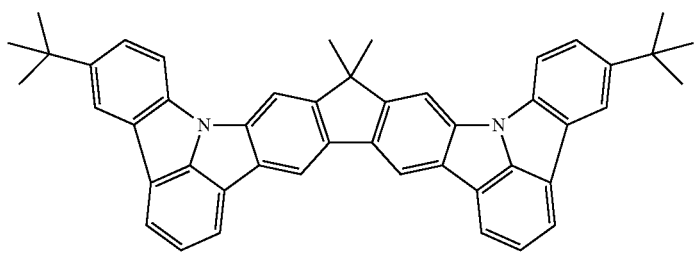

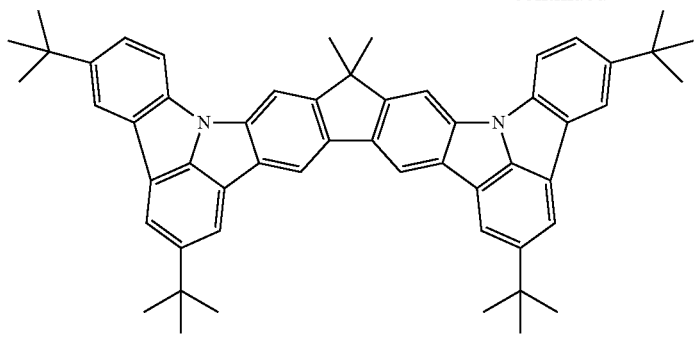
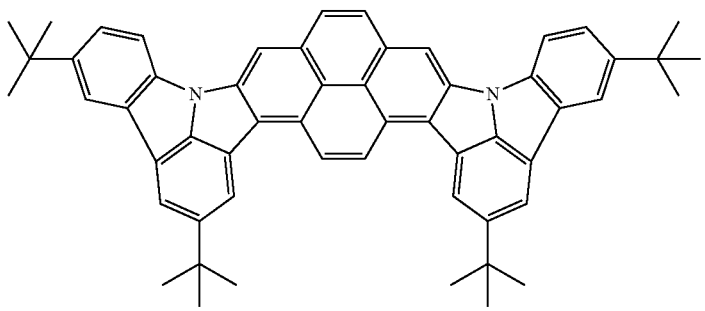
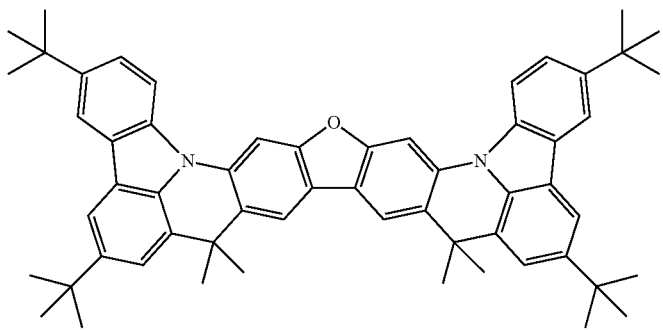
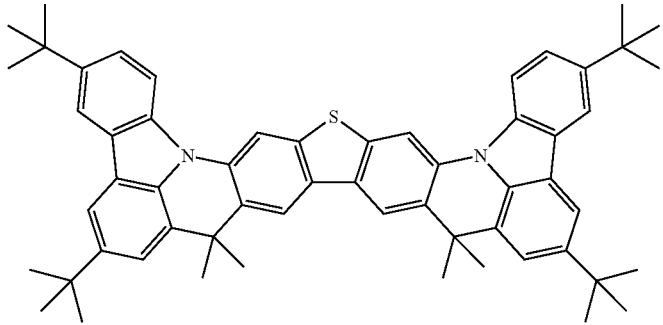
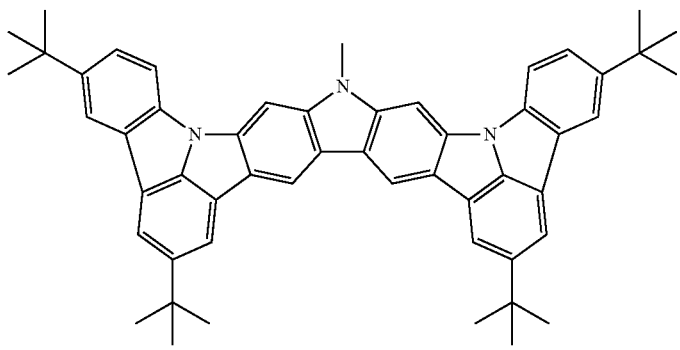

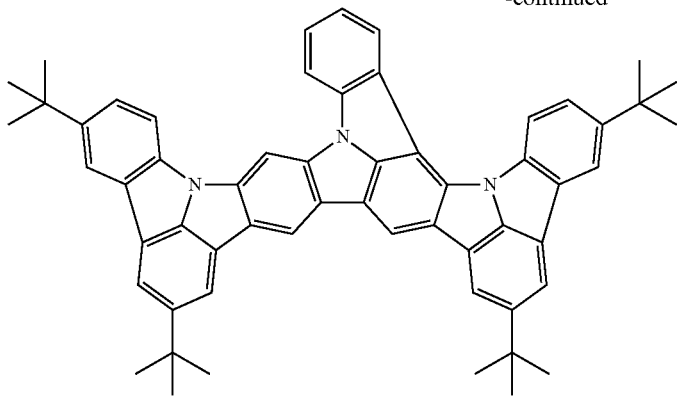
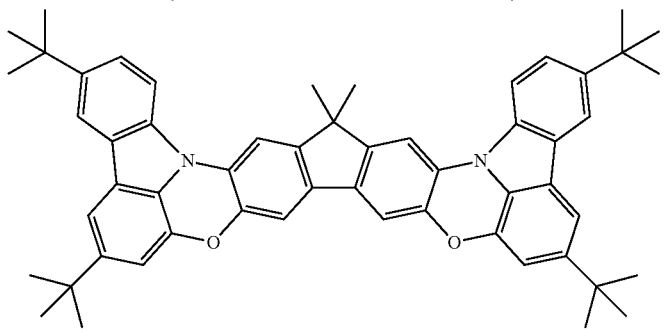
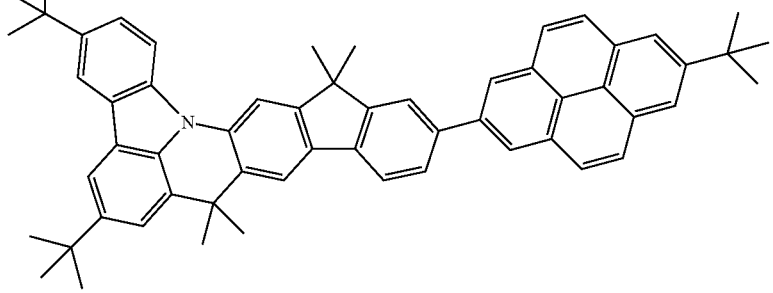
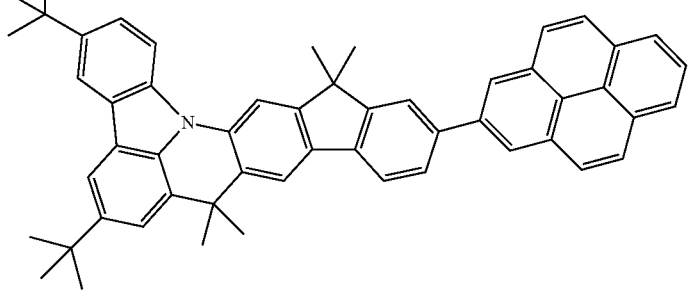
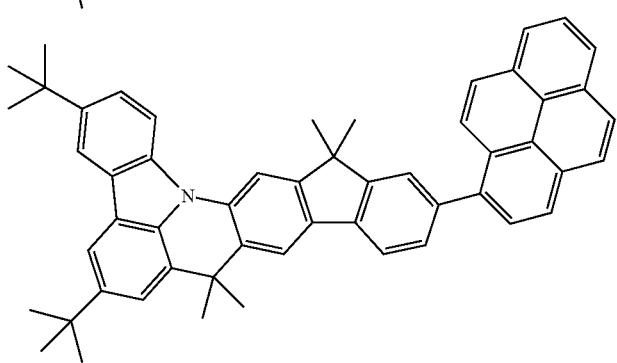

-continued
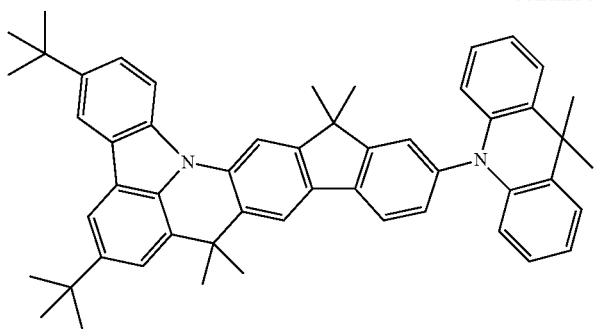
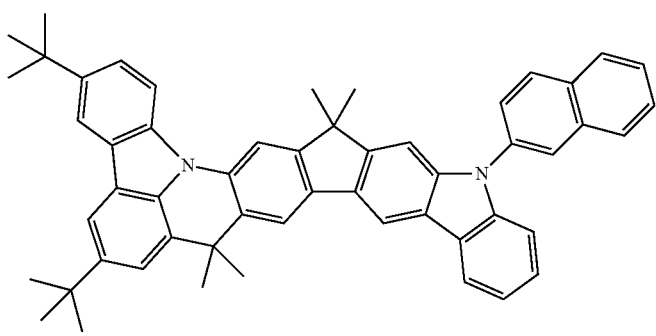
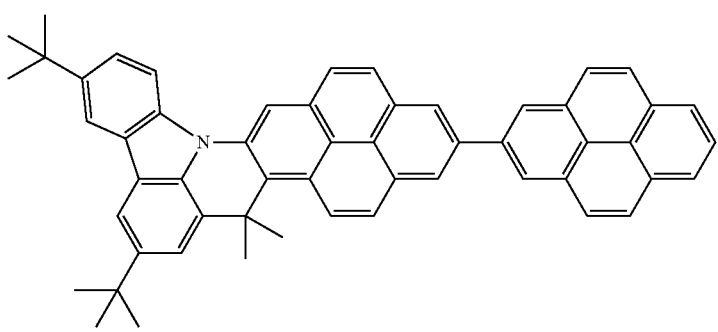
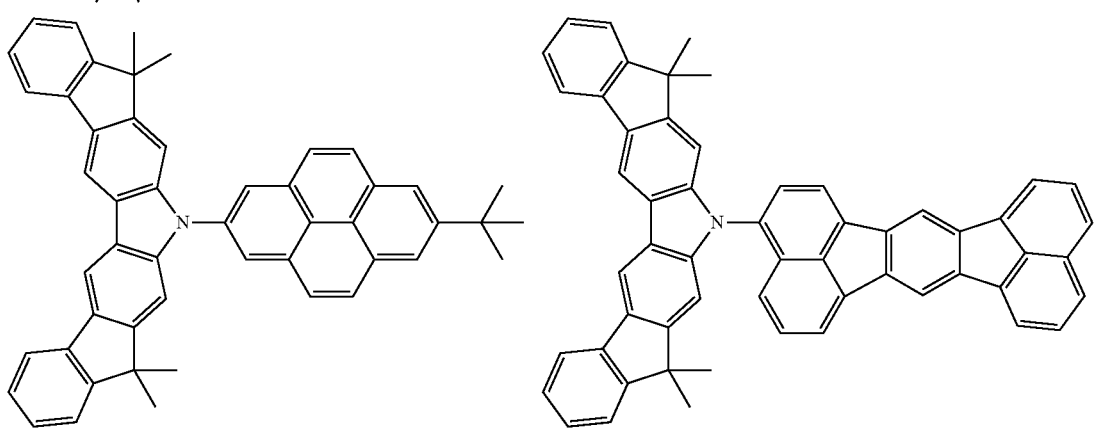

-continued
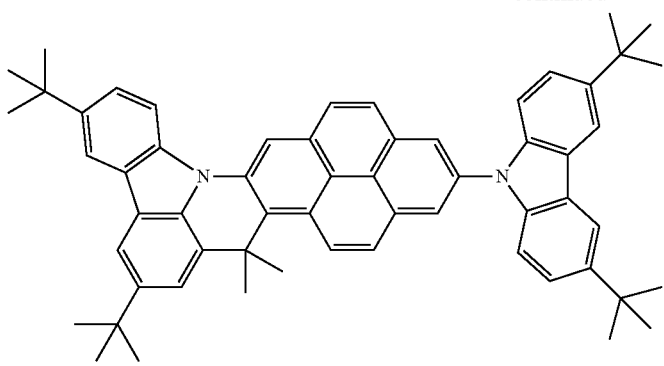
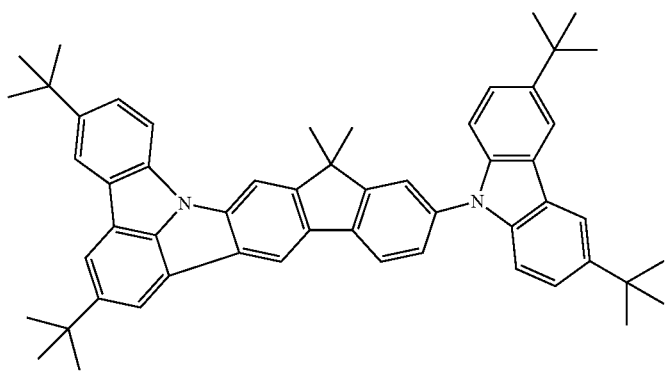
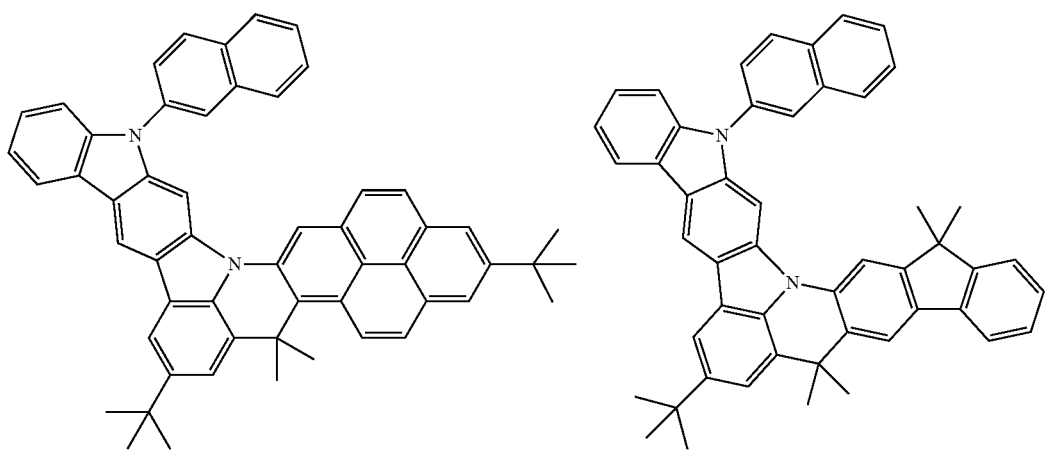
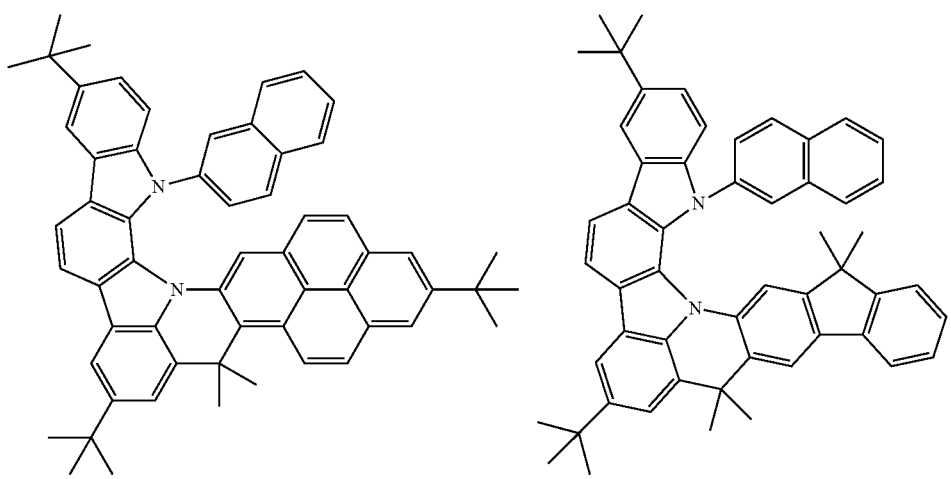

-continued
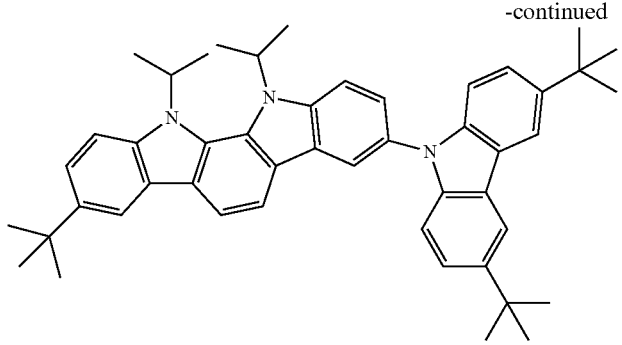
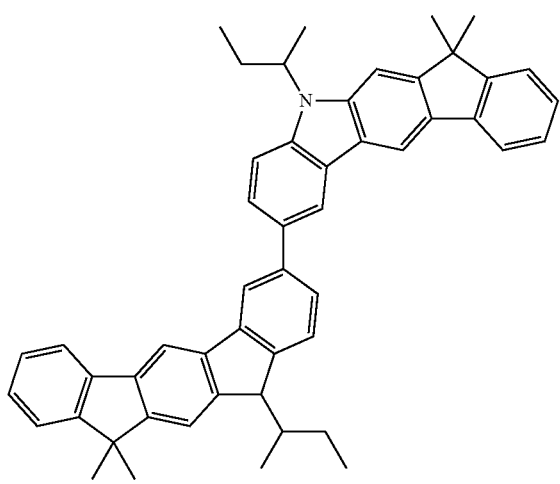
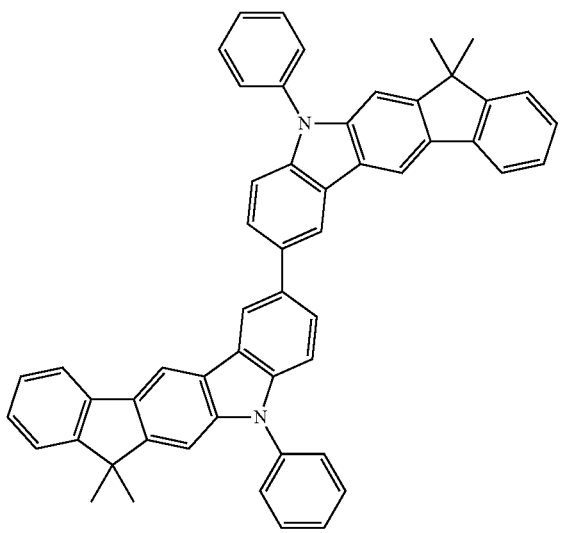
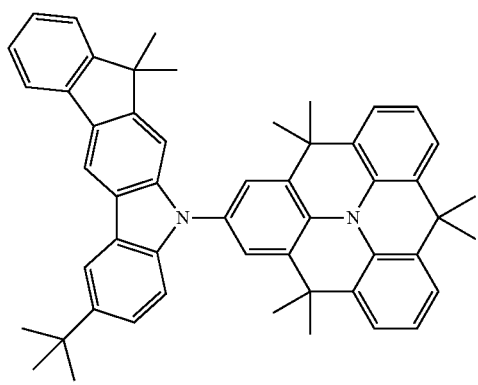
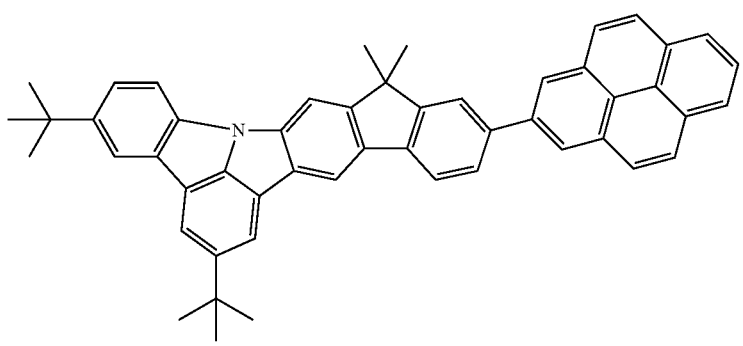

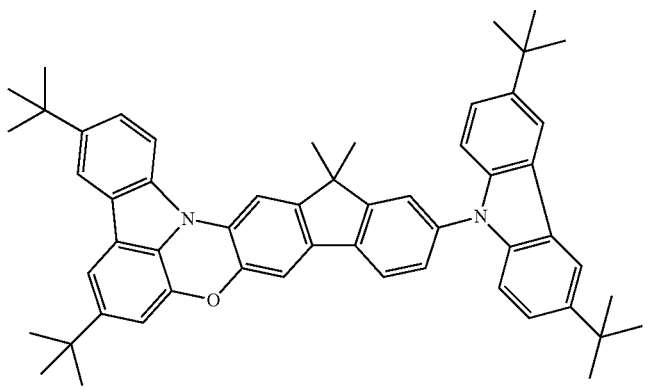
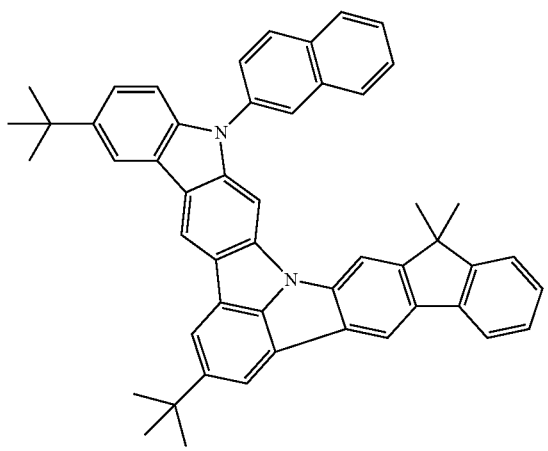
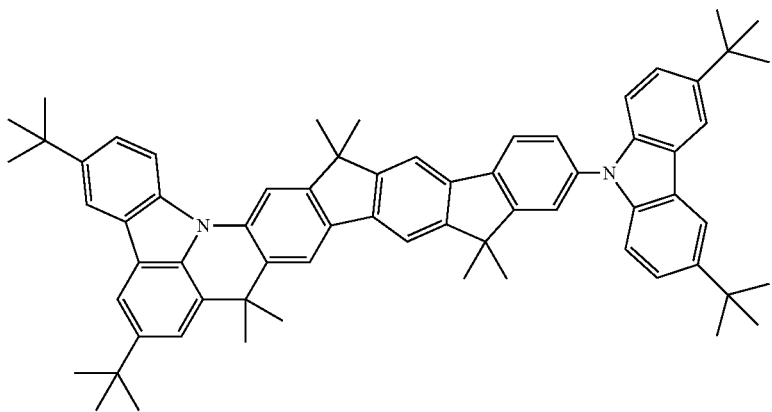
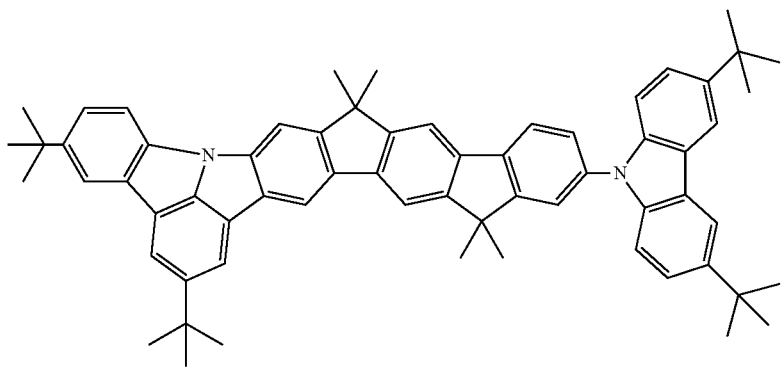

-continued
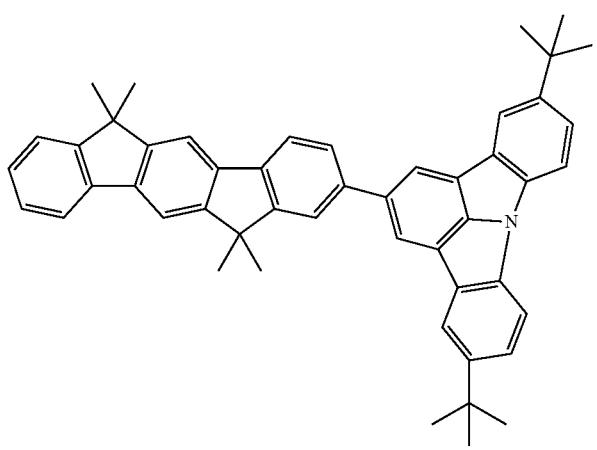
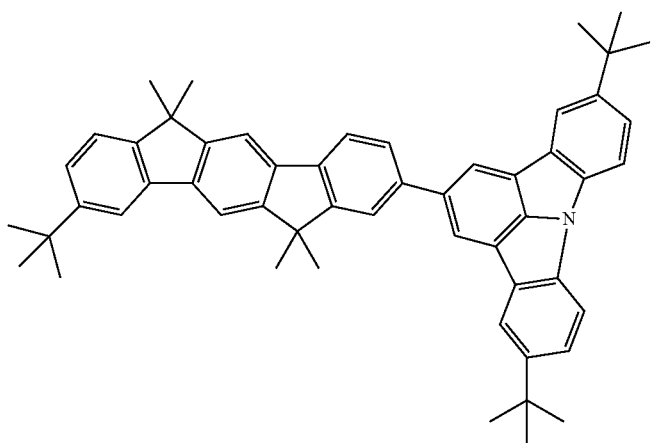
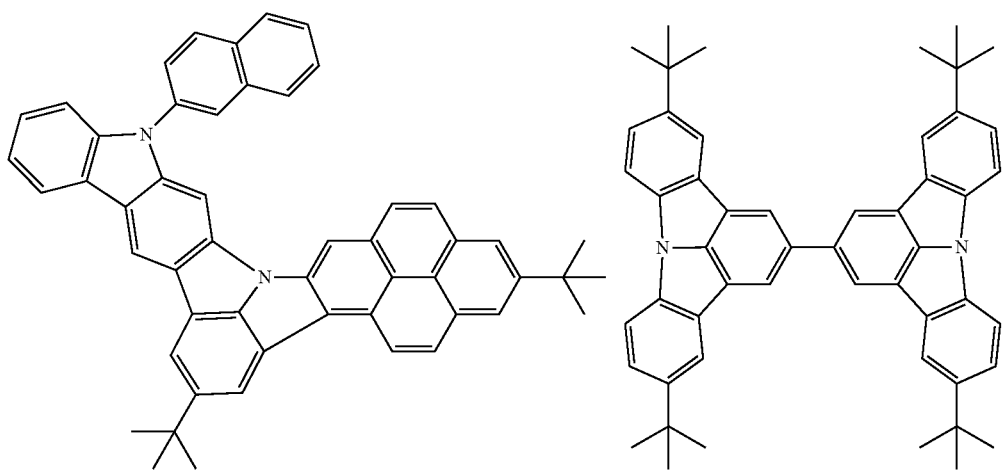

-continued
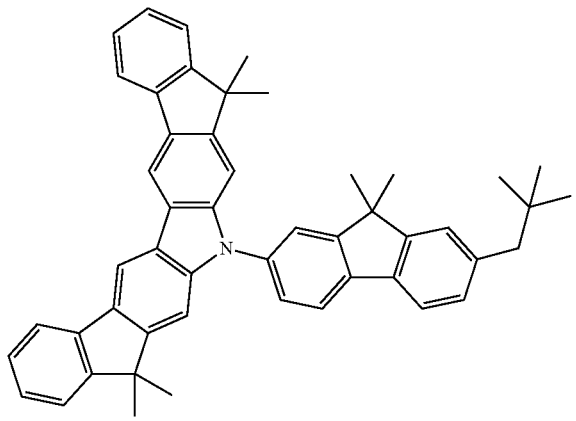
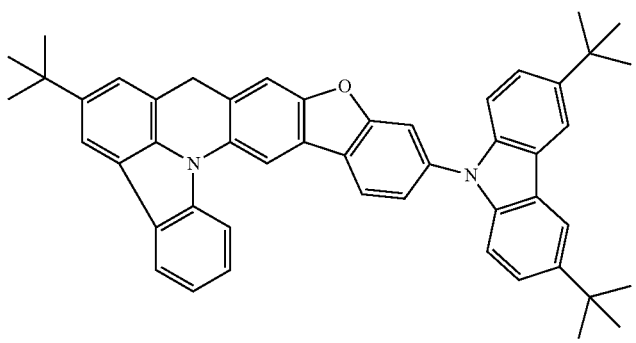
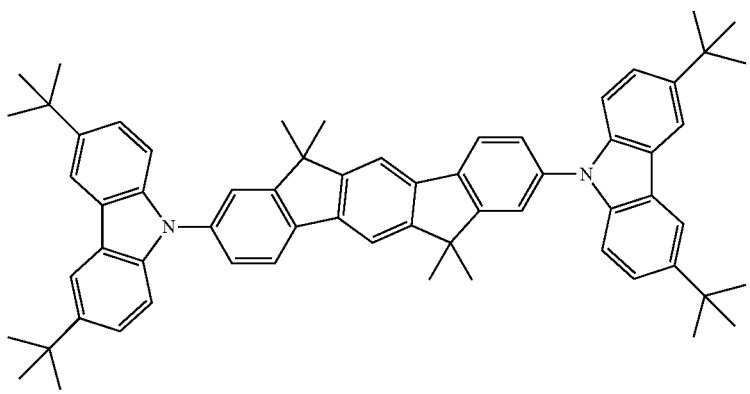
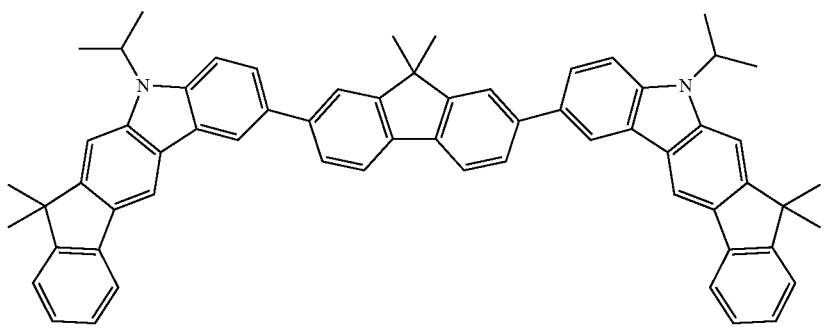

-continued
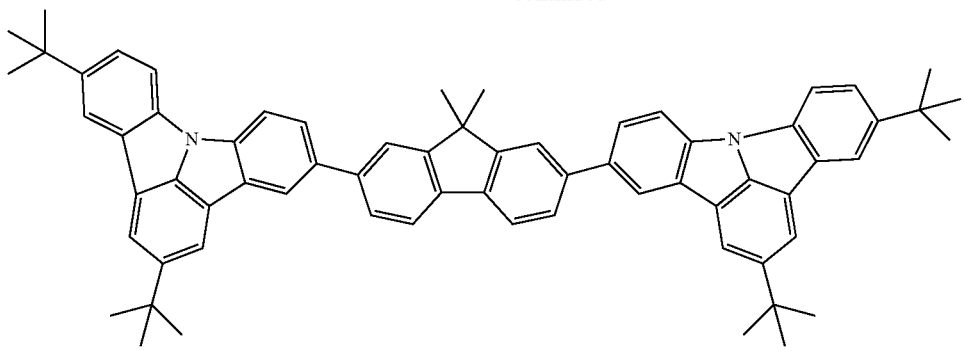

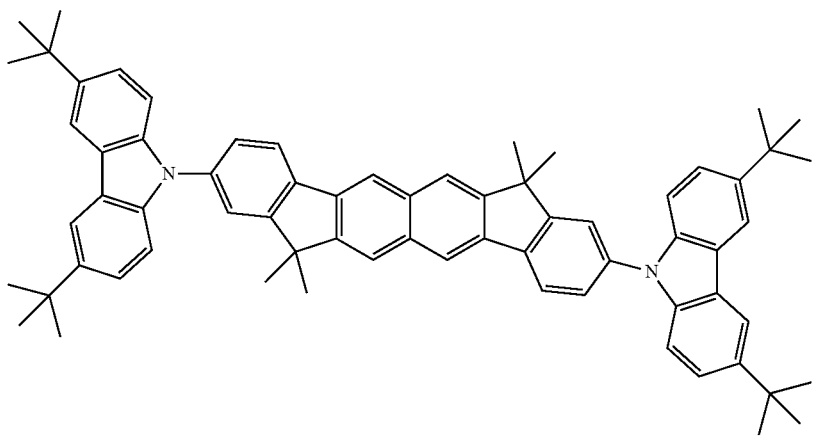
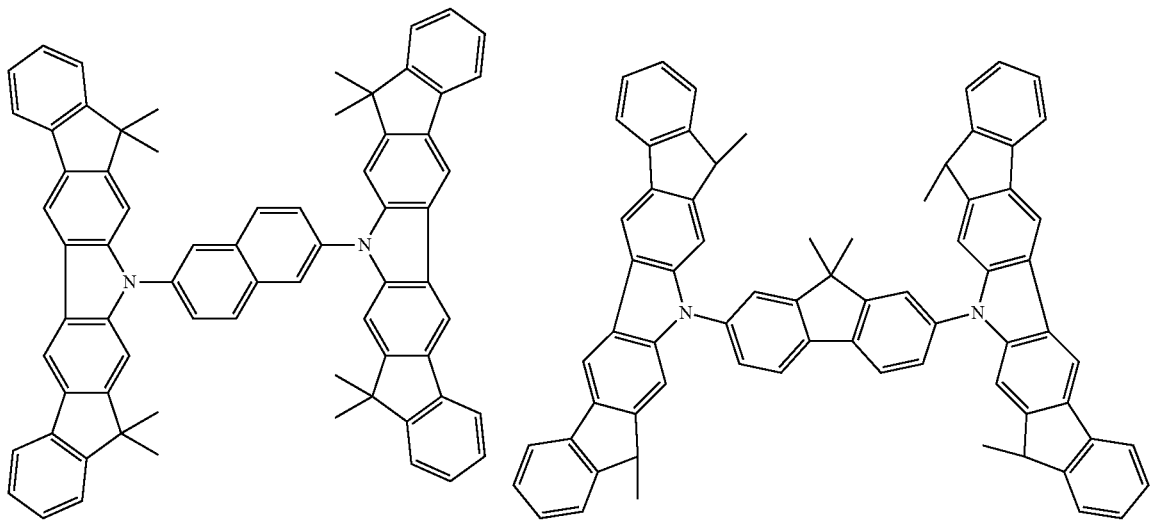
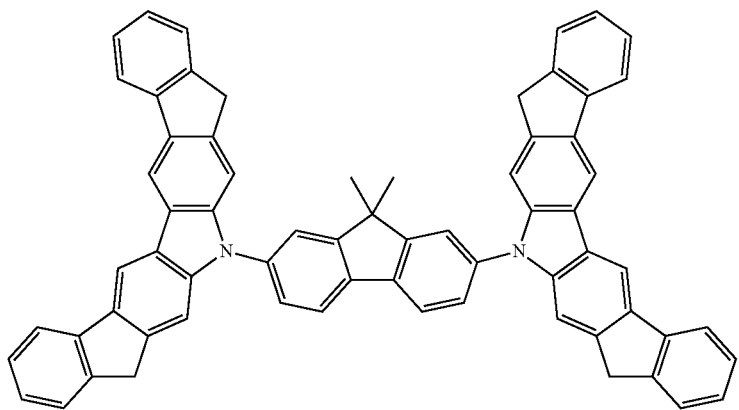

-continued
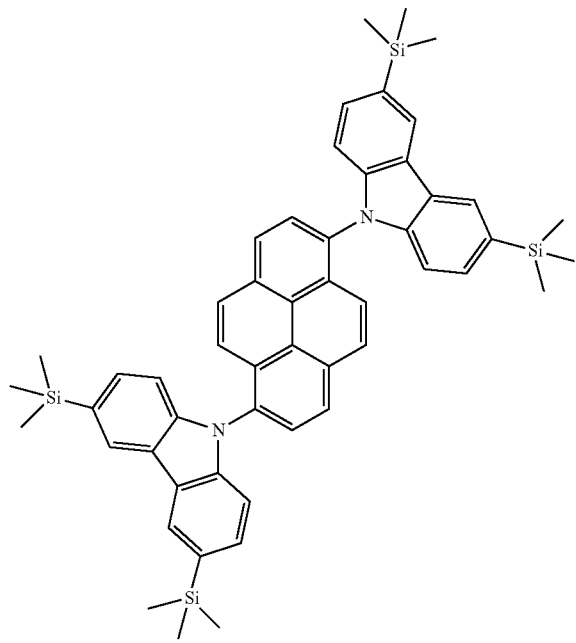
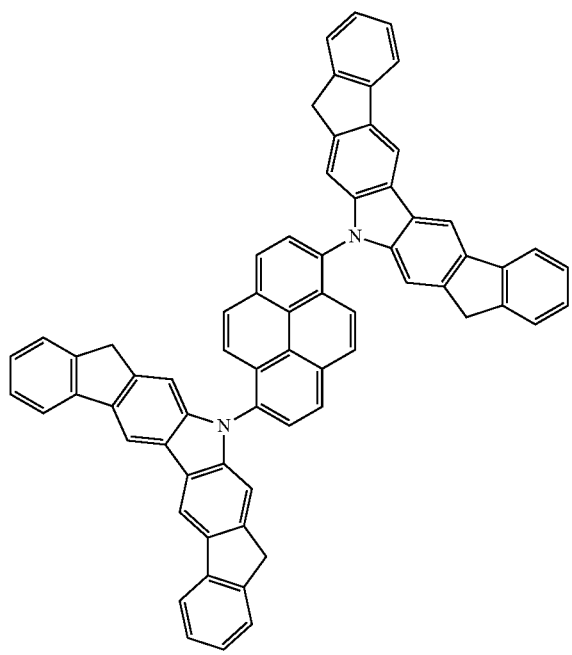

-continued
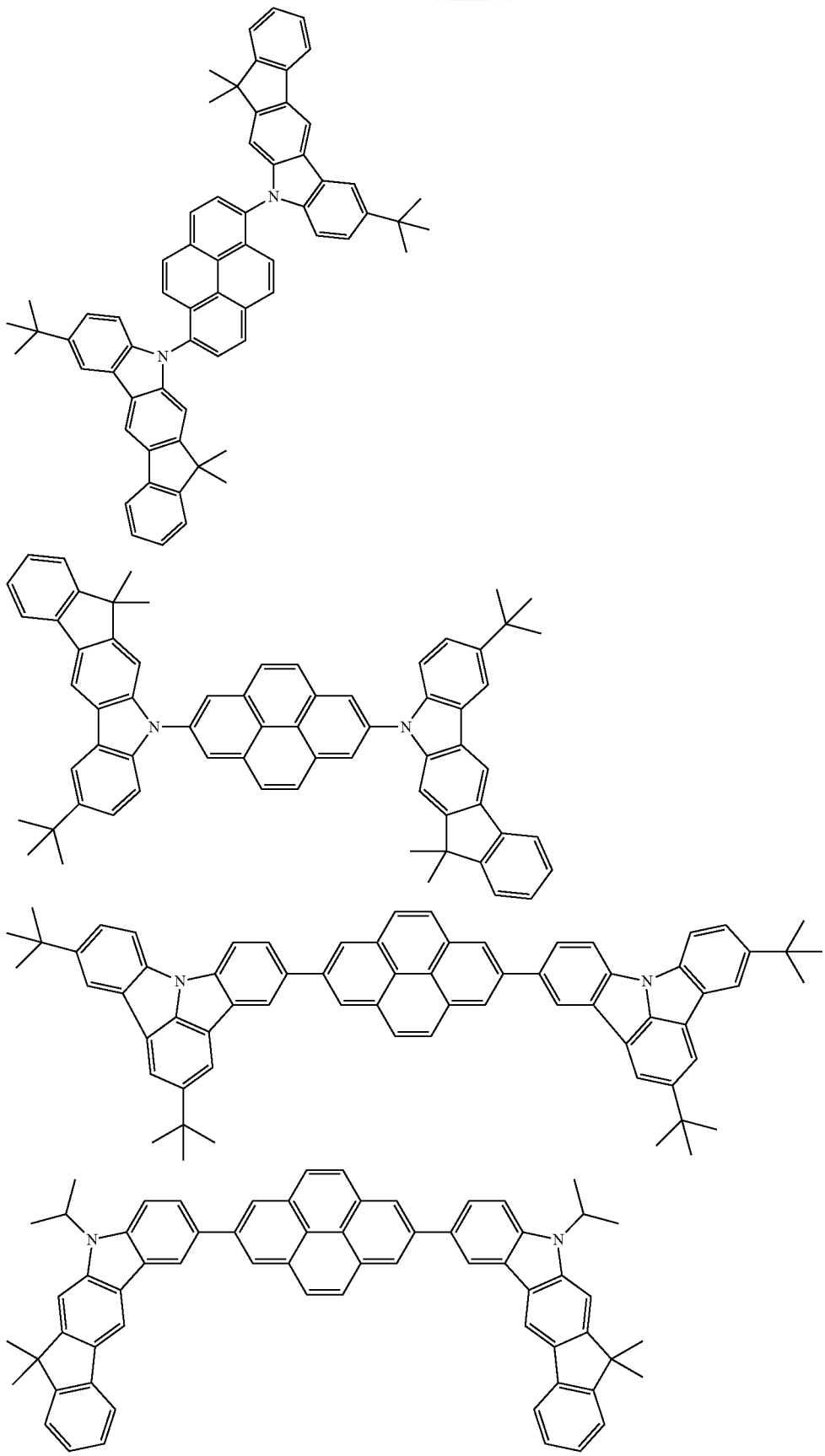

-continued
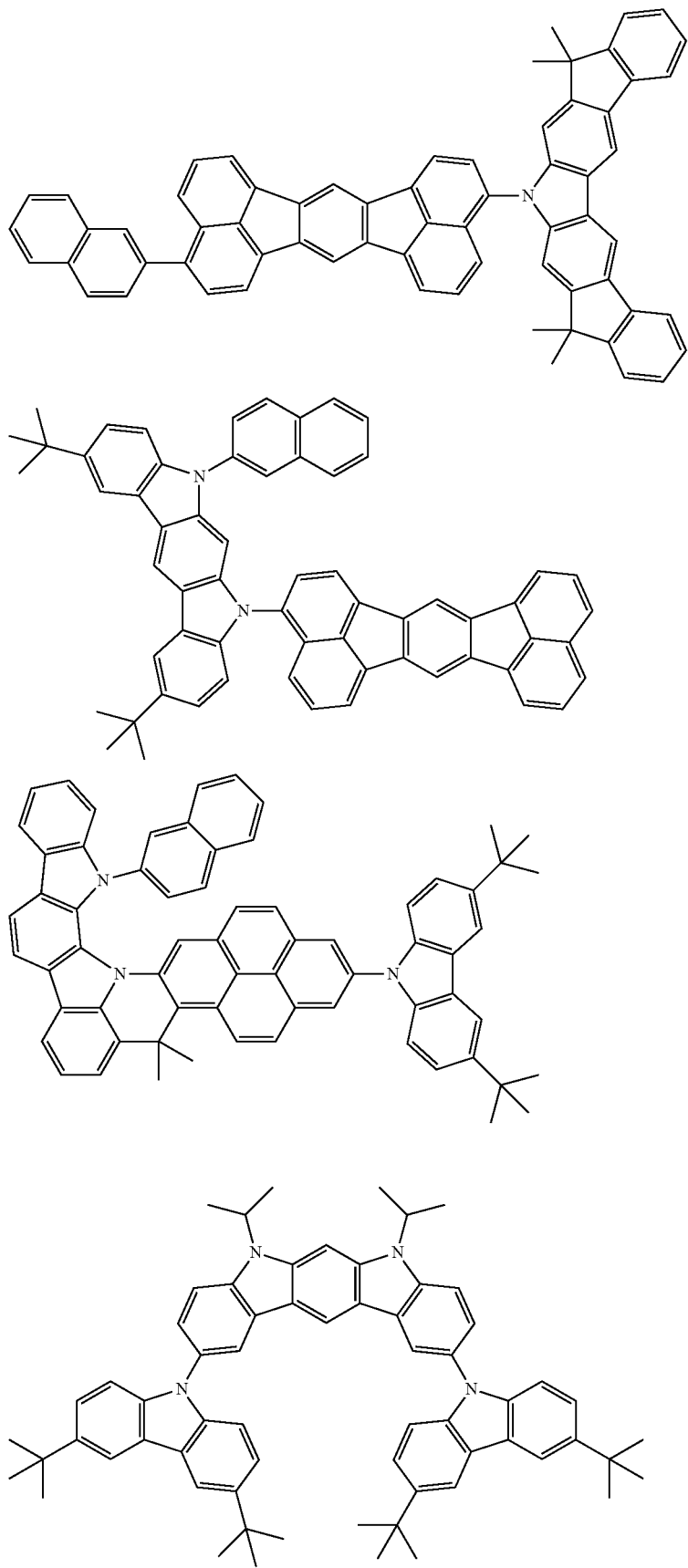

-continued
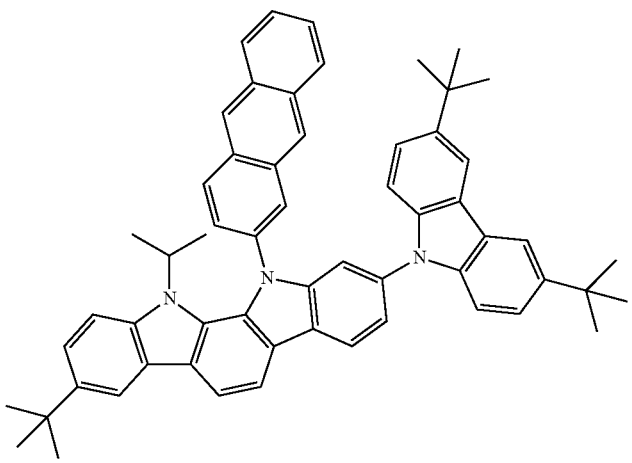
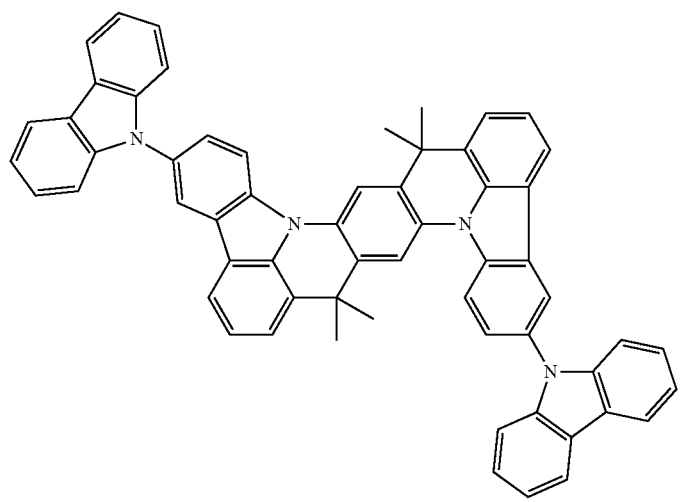
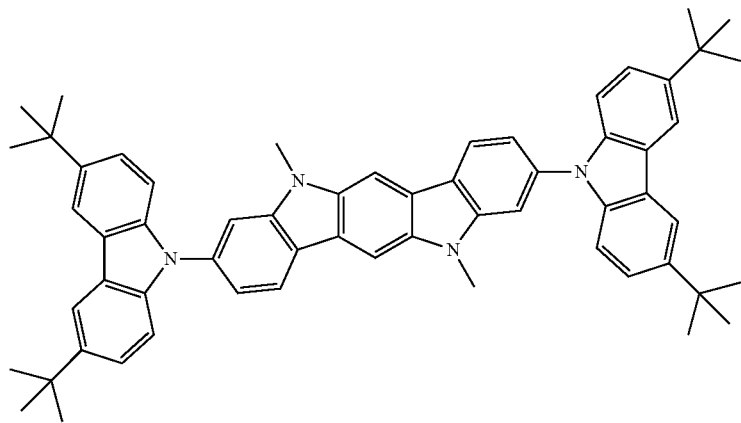

-continued
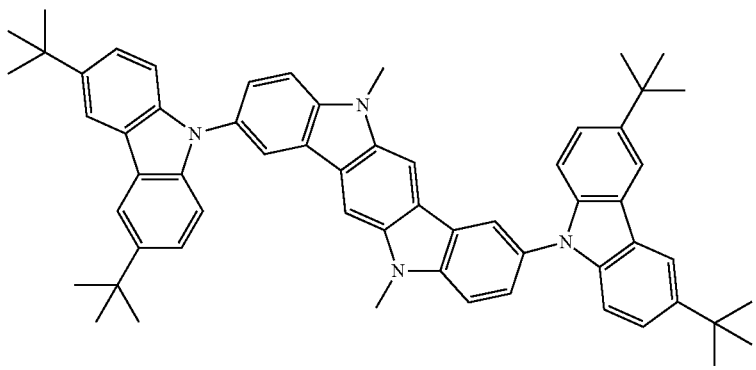
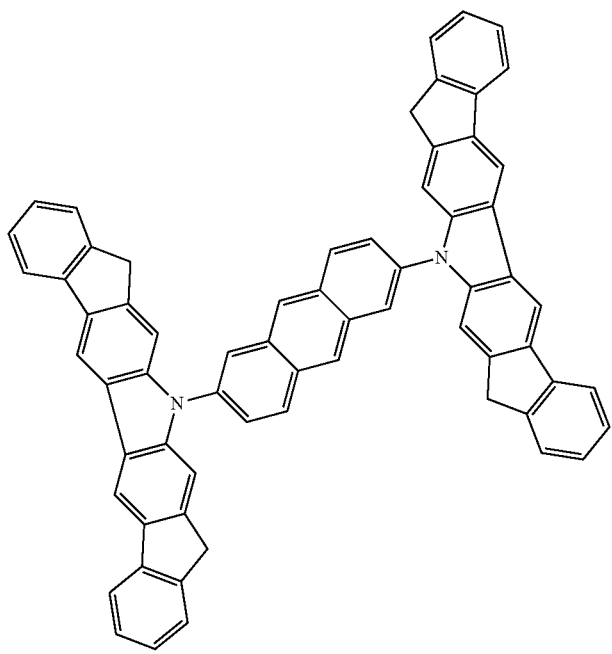
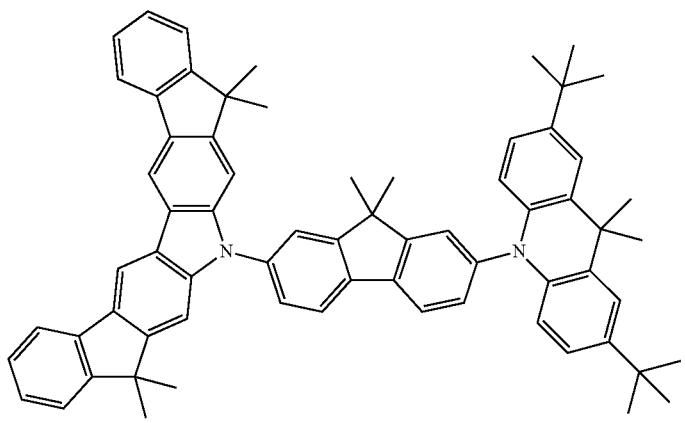

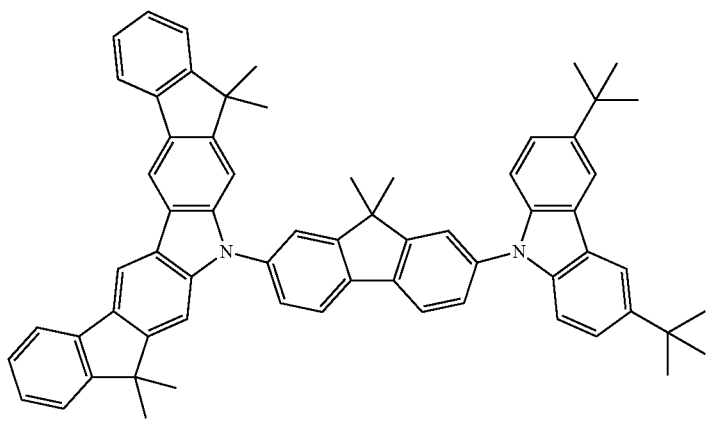
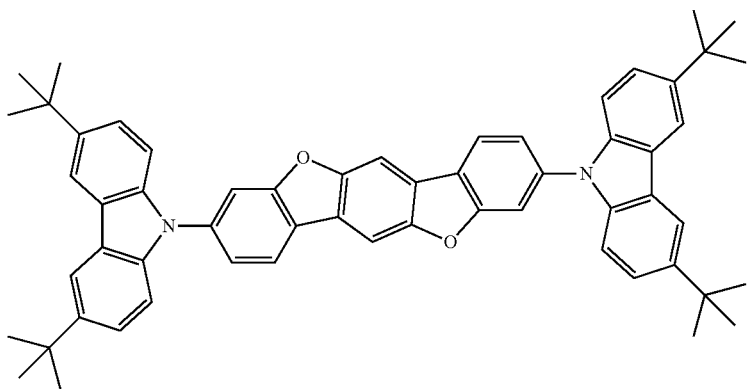
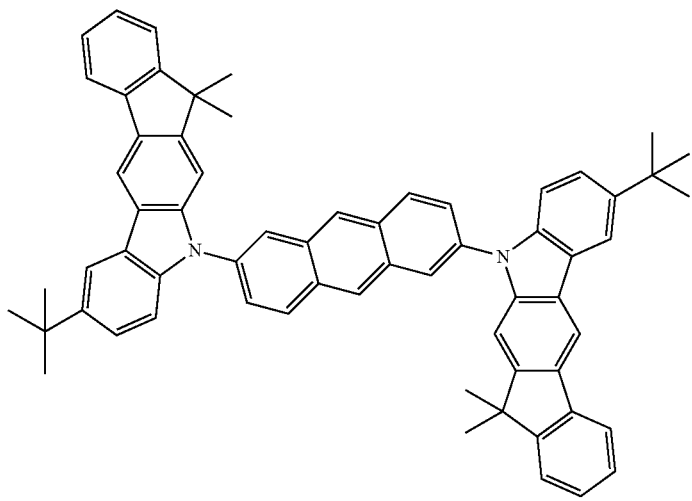

-continued
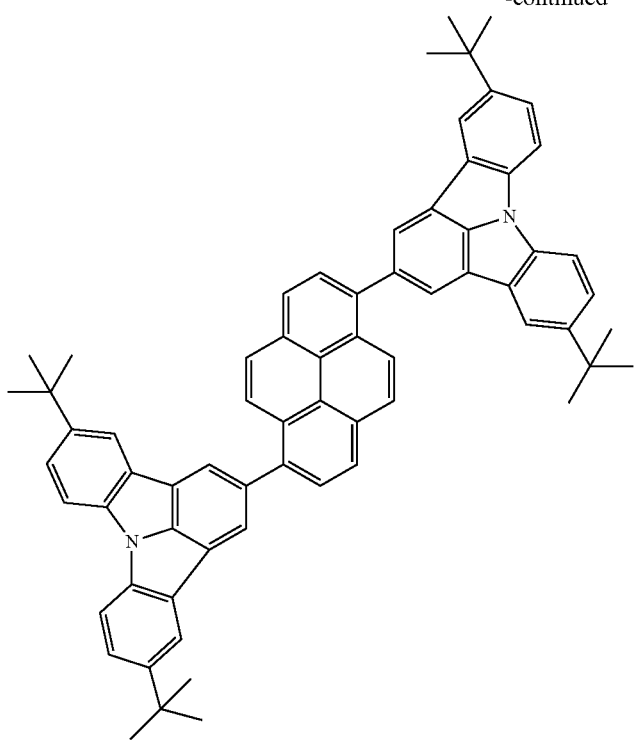
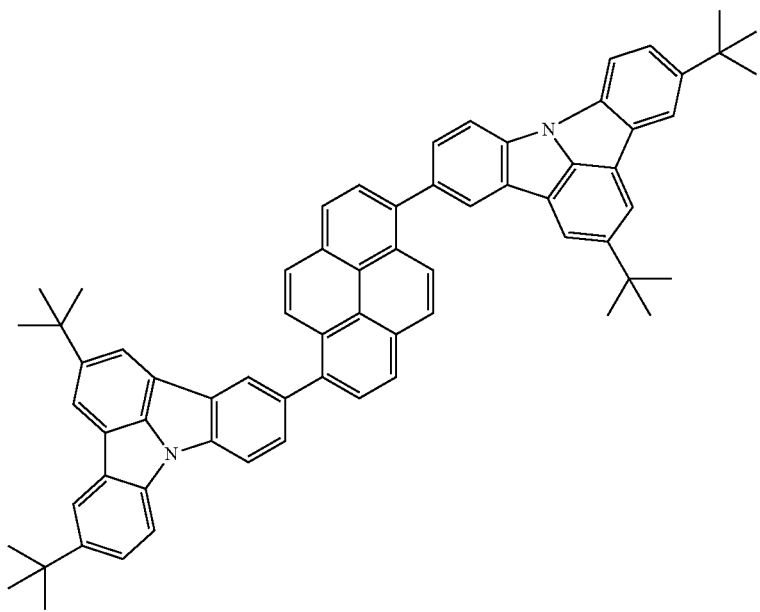

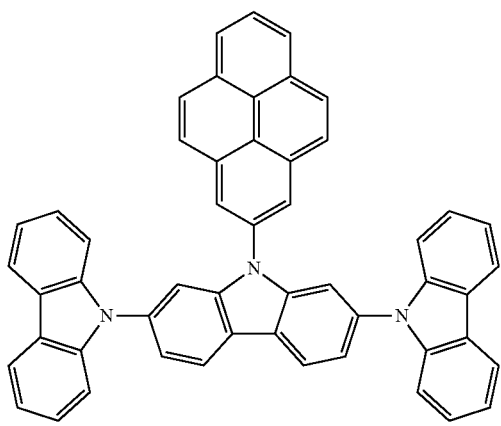
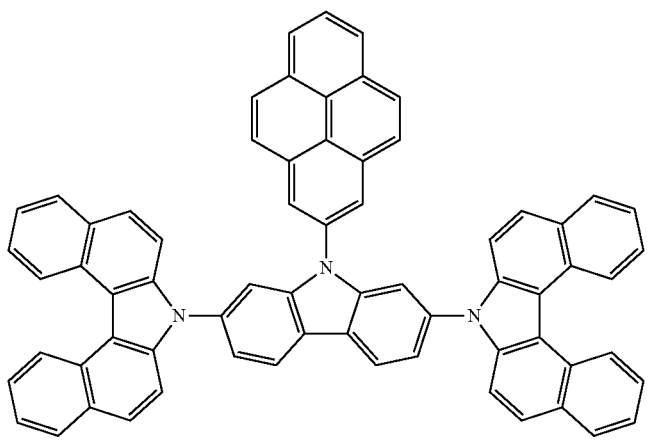
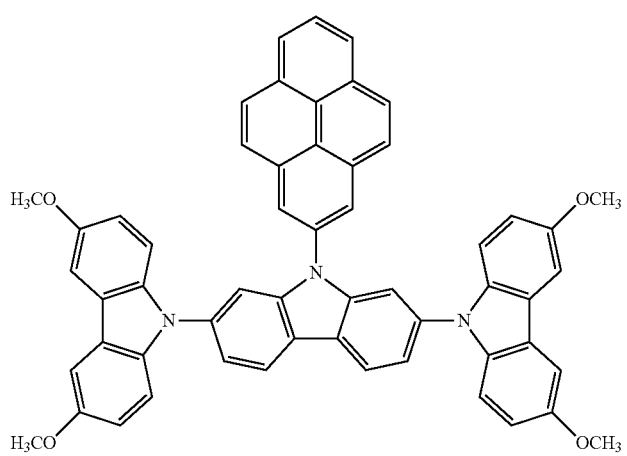

-continued
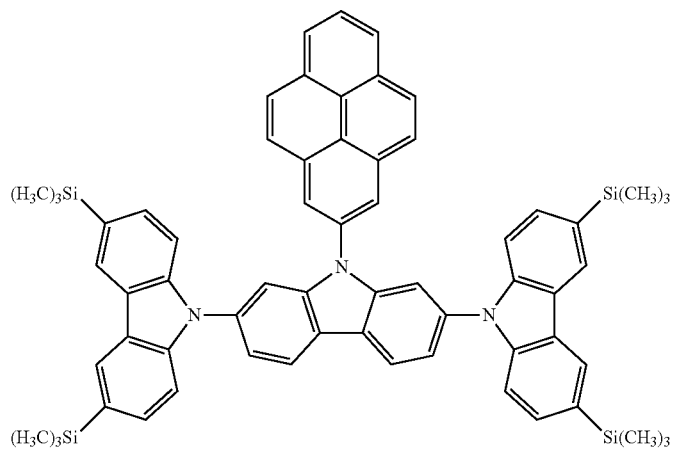
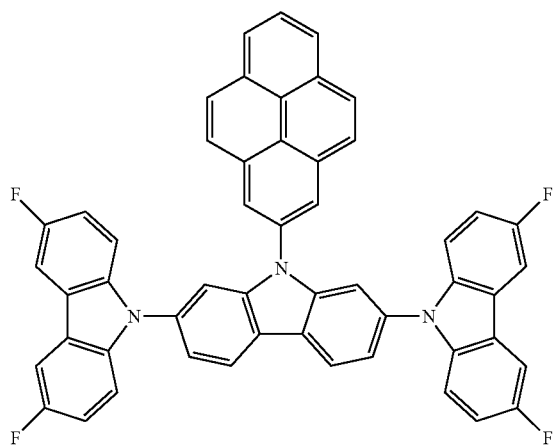
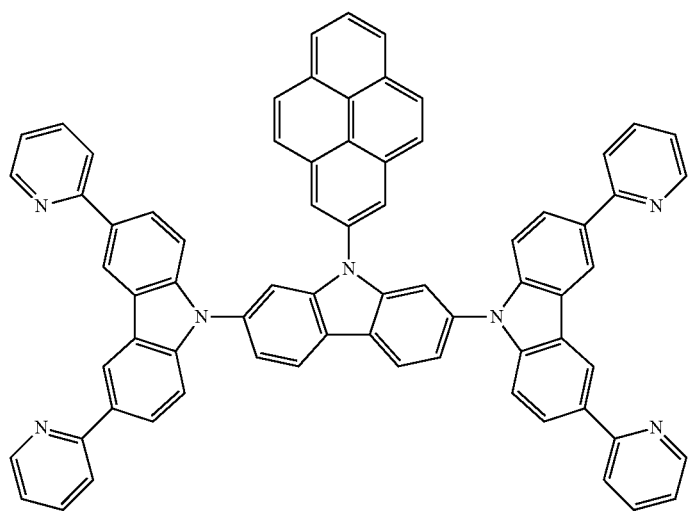

-continued
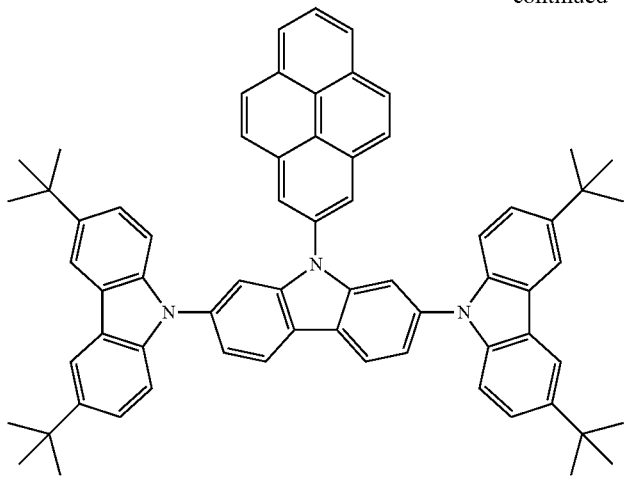
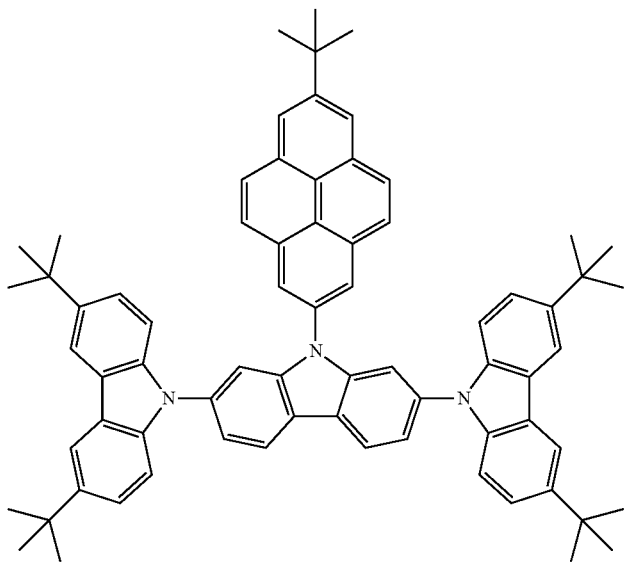
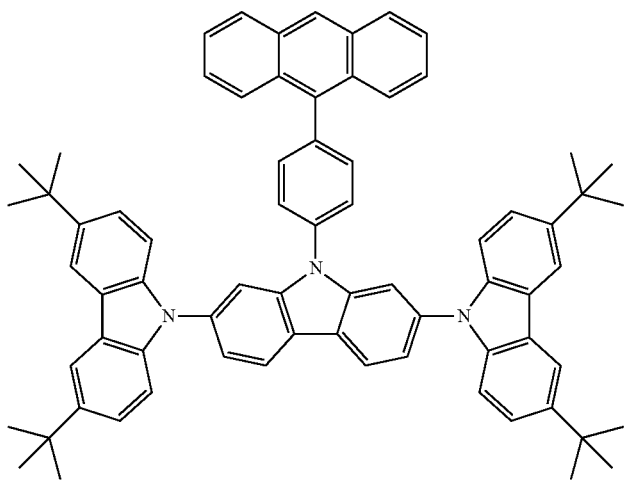

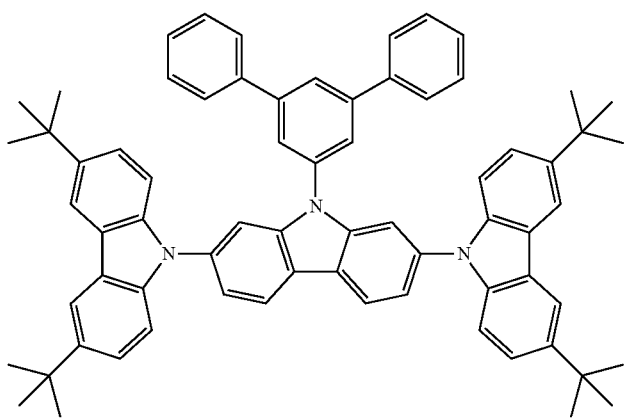
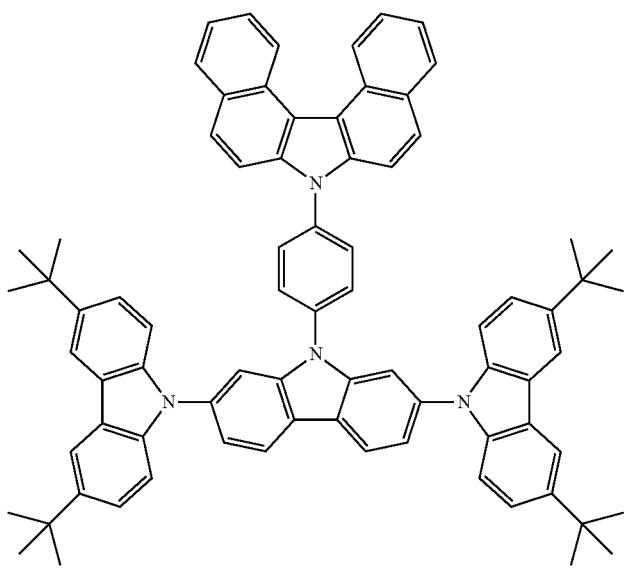
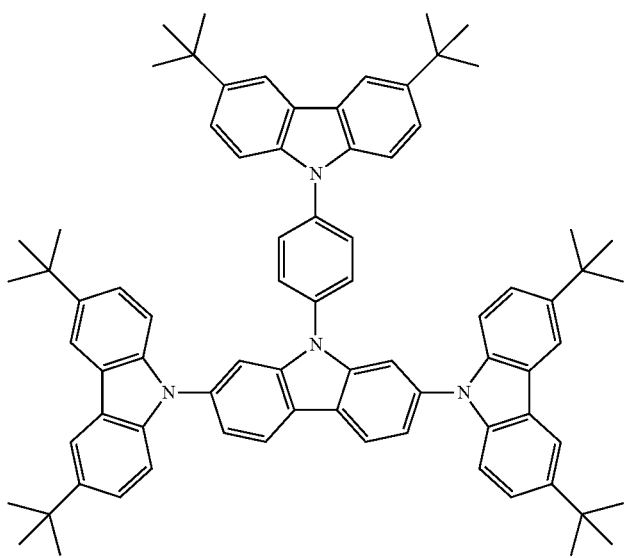

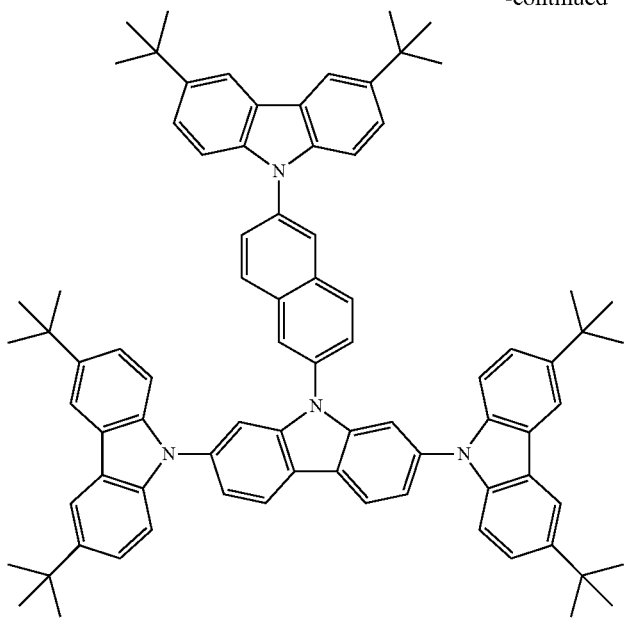
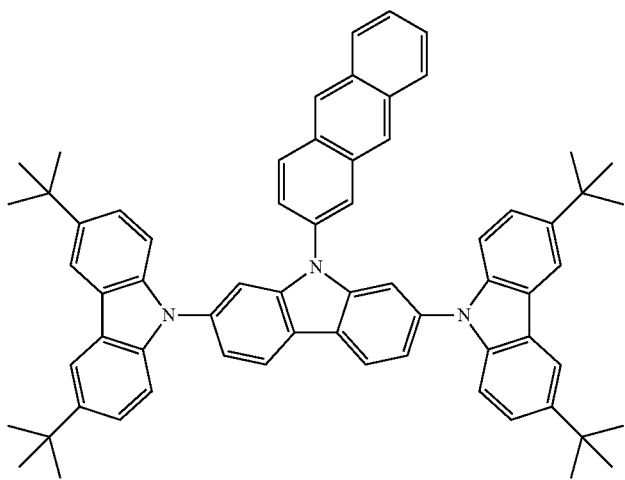
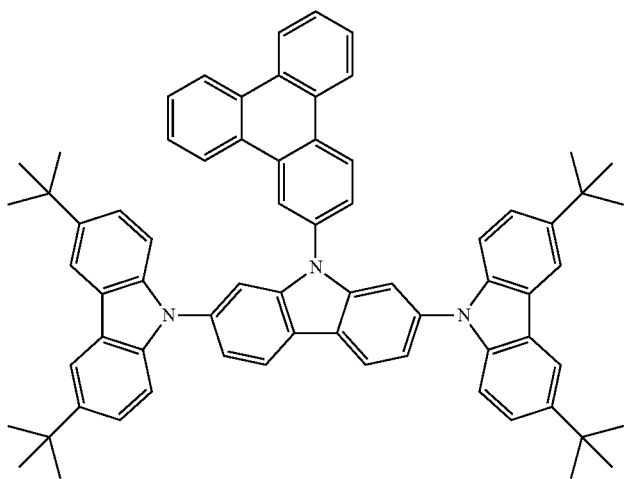

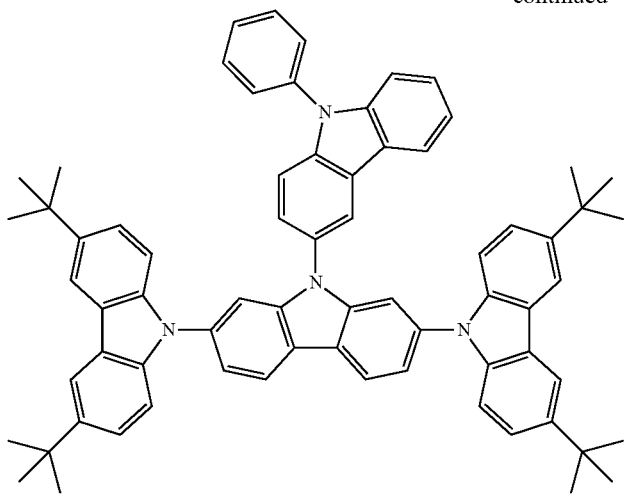
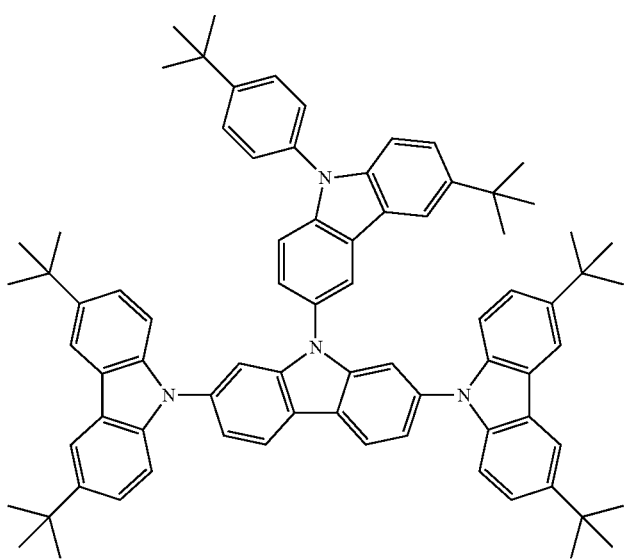
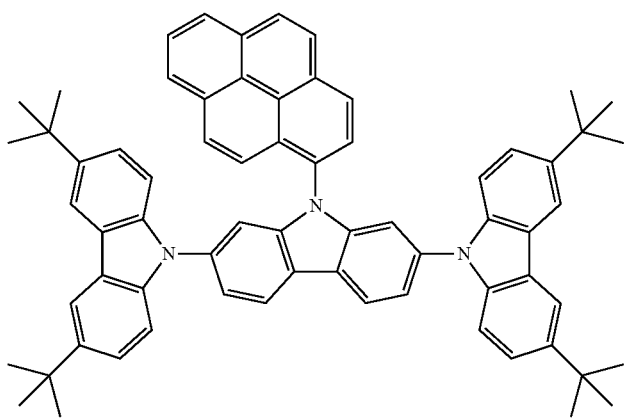

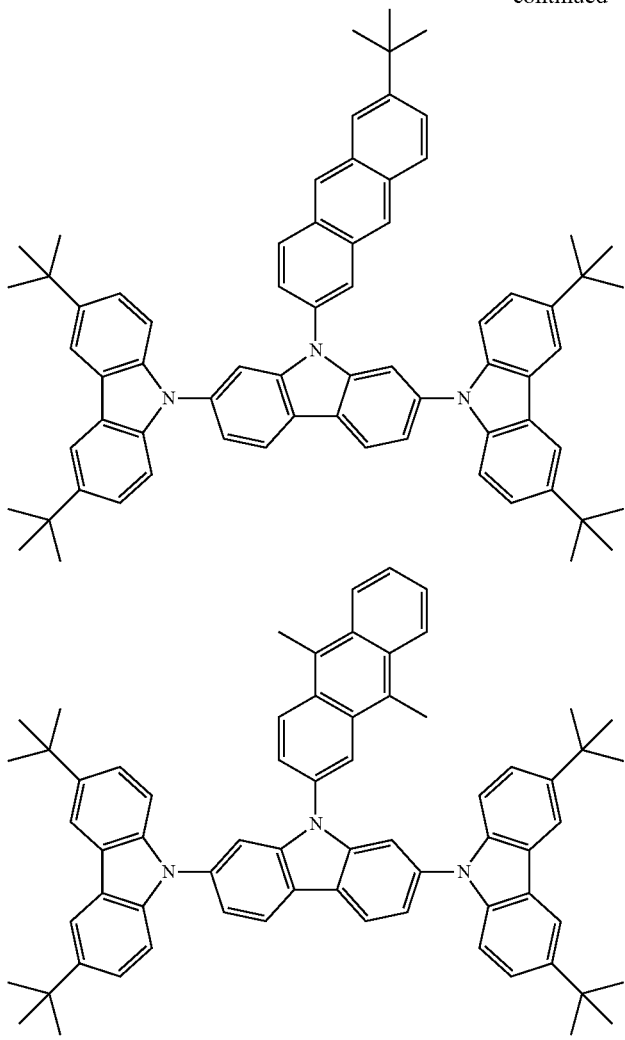

The electron blocking layer may be formed of a plurality of layers.

An inorganic material can also be used as the electron blocking layer. In general, an inorganic material has a higher dielectric constant than an organic material. Accordingly, when the electron blocking layer is used, a large voltage is applied to the photoelectric conversion film, and thus the photoelectric conversion efficiency can be increased. Examples of the material which may become the electron blocking layer include a calcium oxide, a chromium oxide, a chromium copper oxide, a manganese oxide, a cobalt oxide, a nickel oxide, a copper oxide, a gallium copper oxide, a strontium copper oxide, a niobium oxide, a molybdenum oxide, an indium copper oxide, an indium silver oxide, an iridium oxide, and the like. When the electron blocking layer is a single layer, the layer may be a layer formed of an inorganic material. When the electron blocking layer is formed of a plurality of layers, one or two or more layers may be layers formed of an inorganic material.

(Hole Blocking Layer)

An electron-accepting organic material can be used in the hole blocking layer.

As the electron-accepting material, an oxadiazole derivative such as 1,3-bis(4-tert-butylphenyl-1,3,4-oxadiazolyl) phenylene (OXD-7), an anthraquinodimethane derivative, a diphenylquinone derivative, bathocuproine, bathophenanthroline, and derivatives thereof, a triazole compound, a tris(8-hydroxyquinolinate)aluminum complex, a bis(4-methyl-8-quinolinate)aluminum complex, a distyrylarylene derivative, a silole compound, and the like can be used. In addition, any material having sufficient electron transporting properties can be used even though the material is not an electron-accepting organic material. A porphyrin-based compound, a styryl-based compound such as 4-dicyanomethylene-2-methyl-6-(4-(dimethylaminostyryl))-4Hpyran (DCM), and a 4Hpyran-based compound can be used. Specifically, compounds described in [0073] to of JP2008-72090A are preferred.

The method of manufacturing the charge blocking layer is not particularly limited, and film formation can be performed through a dry film forming or a wet film forming method. As the dry film forming method, a deposition method, a sputtering method, or the like can be used. The deposition may be either physical deposition (PVD) or chemical deposition (CVD), but physical deposition such as vacuum deposition is preferred. As the wet film forming method, an ink jet method, a spray method, a nozzle printing method, a spin coating method, a dip coating method, a casting method, a die coating method, a roll coating method, a bar coating method, a gravure coating method, and the like can be used, but an ink jet method is preferred from the viewpoint of high-accuracy patterning.

Each of the thicknesses of the charge blocking layers (electron blocking layer and hole blocking layer) is preferably 10 nm to 200 nm, more preferably 20 nm to 150 nm, and particularly preferably 30 nm to 50 nm. The reason for this is because when this thickness is too small, the dark current suppression effect is reduced, and when the thickness is too large, the photoelectric conversion efficiency is reduced.

<Substrate>

The photoelectric conversion element of the invention may further include a substrate. The type of the substrate to be used is not particularly limited, but a semiconductor substrate, a glass substrate, or a plastic substrate can be used.

The position of the substrate is not particularly limited. However, in general, the conductive film, the photoelectric conversion film, and the transparent conductive film are laminated in this order on the substrate.

<Sealing Layer>

The photoelectric conversion element of the invention may further include a sealing layer. The performance of the photoelectric conversion material may significantly deteriorate under the presence of a deterioration factor such as water molecules. The deterioration can be prevented by covering and sealing the whole photoelectric conversion film with a sealing layer such as diamond-like carbon (DLC) or ceramics such as a metal oxide, a metal nitride, or a metal nitride oxide, which is dense such that penetration of water molecules is prevented.

Regarding the sealing layer, the selection of a material and the manufacturing may be performed according to the descriptions in paragraphs "0210" to "0215" of JP2011-082508A.

[Optical Sensor]

Examples of the use of the photoelectric conversion element include an optical cell and an optical sensor. The photoelectric conversion element of the invention is preferably used as an optical sensor. As the optical sensor, the photoelectric conversion element may be used singly, or the optical sensor may preferably have a line sensor form in which the photoelectric conversion elements are linearly arranged, or a two-dimensional sensor form in which the photoelectric conversion elements are arranged on a plane. The photoelectric conversion element of the invention functions as an imaging element in such a manner that in a line sensor, it converts optical image information into an electric signal using an optical system and a drive portion like a scanner, and in a two-dimensional sensor, it images optical image information on the sensor by an optical system to convert the information into an electric signal like an imaging module.

Since the optical sensor is a power generation device, the efficiency of converting optical energy into electric energy is an important performance, but the dark current which is a current in a dark place does not cause a functional problem. Moreover, a subsequent heating process such as installation of a color filter is not needed. Since an important performance of the optical sensor is to convert a light and dark signal into an electric signal with high accuracy, efficiency of converting a light quantity into a current is also an important performance. However, when a signal is output in a dark place, it becomes noise, and thus a low dark current is required. Resistance to a subsequent process is also important.

[Imaging Element]

Next, an example of a configuration of an imaging element provided with the photoelectric conversion element will be described.

In an example of a configuration to be described hereinbelow, members and the like having the same configurations and actions as the members and the like already described will be denoted by the same or equivalent references in the drawings to simplify or omit the description thereof.

The imaging element is an element which converts optical information of an image into an electric signal, and in which a plurality of photoelectric conversion elements are arranged on a matrix on the same plane, an optical signal is converted into an electric signal in each photoelectric conversion element (pixel), and the electric signal can be sequentially output to the outside of the imaging element for each pixel. Therefore, one pixel is formed of one photoelectric conversion element and one or more transistors.

Figure 2:
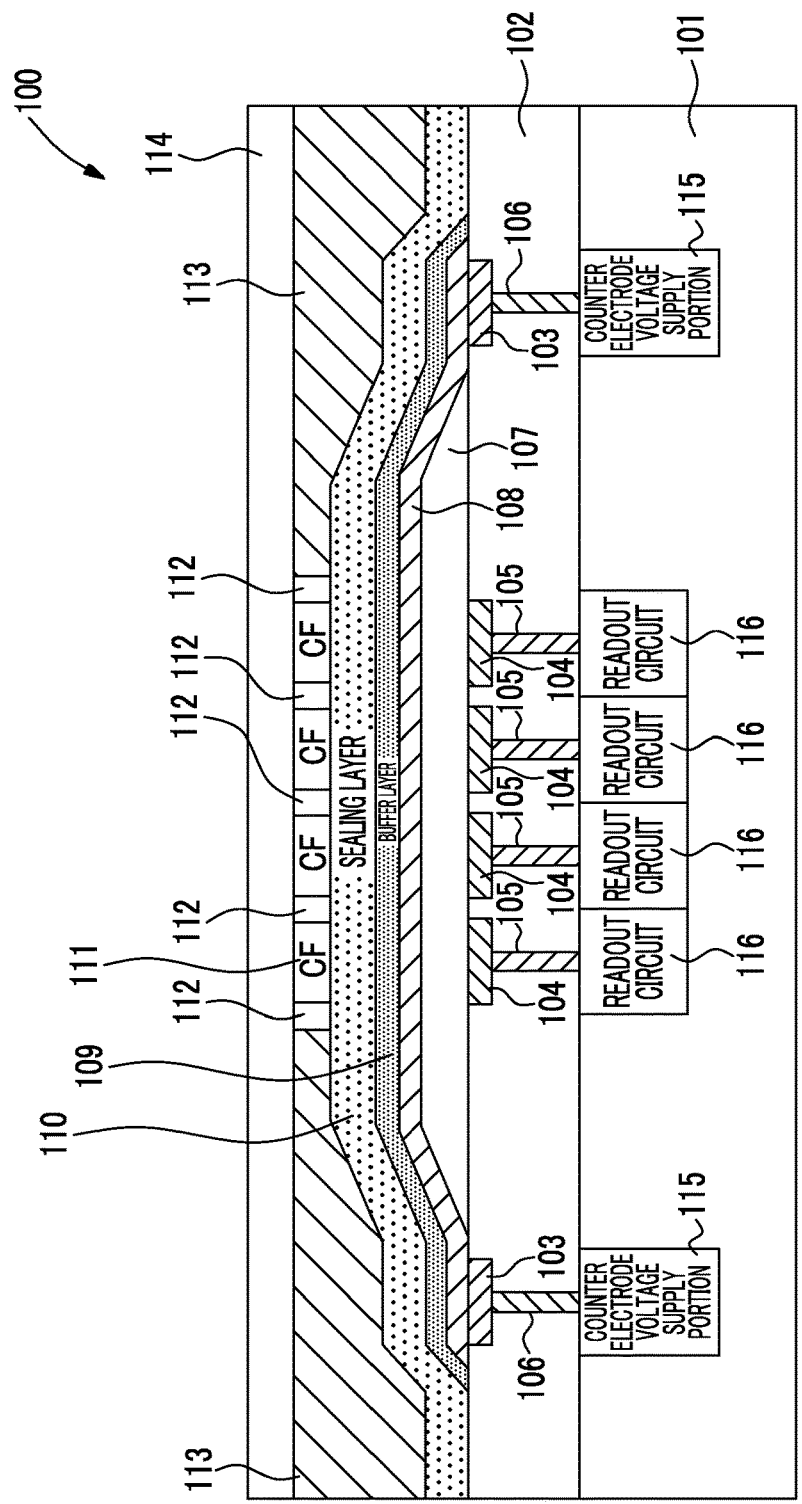
FIG. 2 is a schematic cross-sectional view of one pixel of an imaging element.

FIG. 2 is a schematic cross-sectional view showing a schematic configuration of an imaging element for describing an embodiment of the invention. This imaging element is used by being installed on an imaging device such as a digital camera or a digital video camera, an imaging module such as an electronic endoscope or a mobile phone, or the like.

This imaging element has a plurality of photoelectric conversion elements having a configuration shown in FIG. 1 and a circuit board having readout circuits formed therein to read out a signal according to charges generated in the photoelectric conversion film of each photoelectric conversion element, and has a configuration in which the plurality of photoelectric conversion elements are one- or two-dimensionally arranged on the same plane over the circuit board.

An imaging element 100 shown in FIG. 2 is provided with a substrate 101, an insulating layer 102, connecting electrodes 103, pixel electrodes (lower electrodes) 104, connecting portions 105, connecting portions 106, a photoelectric conversion film 107, a counter electrode (upper electrode) 108, a buffer layer 109, a sealing layer 110, color filters (CFs) 111, a partition wall 112, a light shielding layer 113, a protective layer 114, counter electrode voltage supply portions 115, and readout circuits 116.

The pixel electrode 104 has the same function as the electrode 11 of the photoelectric conversion element 10*a* shown in FIG. 1. The counter electrode 108 has the same function as the electrode 15 of the photoelectric conversion element 10*a* shown in FIG. 1. The photoelectric conversion film 107 has the same configuration as the layer provided between the electrode 11 and the electrode 15 of the photoelectric conversion element 10*a* shown in FIG. 1.

The substrate 101 is a glass substrate or a semiconductor substrate such as Si. The insulating layer 102 is formed on the substrate 101. The plurality of pixel electrodes 104 and the plurality of connecting electrodes 103 are formed in a surface of the insulating layer 102.

The photoelectric conversion film 107 is a layer which is provided to cover the plurality of pixel electrodes 104 and is common to all of the photoelectric conversion elements.

The counter electrode 108 is one electrode which is provided on the photoelectric conversion film 107 and is common to all of the photoelectric conversion elements. The counter electrode 108 is also formed on the connecting electrodes 103 arranged on the outside of the photoelectric conversion film 107, and is connected to the connecting electrodes 103.

The connection portion 106 is a plug or the like embedded in the insulating layer 102 to electrically connect the connection electrode 103 and the counter electrode voltage supply portion 115. The counter electrode voltage supply portion 115 is formed in the substrate 101 to apply a predetermined voltage to the counter electrode 108 via the connection portion 106 and the connection electrode 103. When the voltage to be applied to the counter electrode 108 is higher than a power-supply voltage of the imaging element, the predetermined voltage is supplied by boosting the power-supply voltage by a booster circuit such as a charge pump.

The readout circuit 116 is provided corresponding to each of the plurality of pixel electrodes 104 in the substrate 101, and reads out a signal according to charges collected by the corresponding pixel electrode 104. The readout circuit 116 is composed of, for example, a CCD, a CMOS circuit, a TFT circuit, or the like, and is light-shielded by a light shielding layer (not shown) disposed in the insulating layer 102. The readout circuit 116 is electrically connected to the corresponding pixel electrode 104 via the connection portion 105.

The buffer layer 109 is formed to cover the counter electrode 108 on the counter electrode 108. The sealing layer 110 is formed to cover the buffer layer 109 on the buffer layer 109. The color filter 111 is formed at a position opposed to each pixel electrode 104 on the sealing layer 110. The partition wall 112 is provided between the color filters 111 to improve the light transmission efficiency of the color filter 111.

The light shielding layer 113 is formed in a region excluding the region where the color filters 111 and the partition walls 112 are provided on the sealing layer 110, and prevents light from entering the photoelectric conversion film 107 formed in a region excluding the effective pixel region. The protective layer 114 is formed on the color filters 111, the partition walls 112, and the light shielding layer 113, and protects the entire imaging element 100.

In the imaging element 100 configured as described above, when light enters, this light enters the photoelectric conversion film 107 and charges are generated herein. Among the generated charges, holes are collected by the pixel electrodes 104, and a voltage signal according to the amount of the holes is output to the outside of the imaging element 100 by the readout circuit 116.

The method of manufacturing the imaging element 100 is as follows.

The connection portions 105 and 106, the plurality of connection electrodes 103, the plurality of pixel electrodes 104, and the insulating layer 102 are formed on a circuit board having the counter electrode voltage supply portions 115 and the readout circuits 116 formed therein. The plurality of pixel electrodes 104 are arranged, for example, in a square lattice form in the surface of the insulating layer 102.

Next, the photoelectric conversion film 107 is formed on the plurality of pixel electrodes 104 through, for example, a vacuum heating deposition method. Next, the counter electrode 108 is formed under vacuum on the photoelectric conversion film 107 through, for example, a sputtering method. Next, the buffer layer 109 and the sealing layer 110 are sequentially formed on the counter electrode 108 through, for example, a vacuum heating deposition method. Next, the color filters 111, the partition walls 112, and the light shielding layer 113 are formed, and then the protective layer 114 is formed to complete the imaging element 100.

It is possible to prevent a deterioration in the performance of the plurality of photoelectric conversion elements when adding a process of placing the imaging element 100 during the production under no vacuum between the process of forming the photoelectric conversion film 107 and the process of forming the sealing layer 110 in the method of manufacturing the imaging element 100. When this process is added, it is possible to suppress the manufacturing cost while preventing the deterioration in the performance of the imaging element 100.

EXAMPLES

Examples will be shown hereinbelow, but the invention is not limited thereto.

Example 1-1

Figure 3:
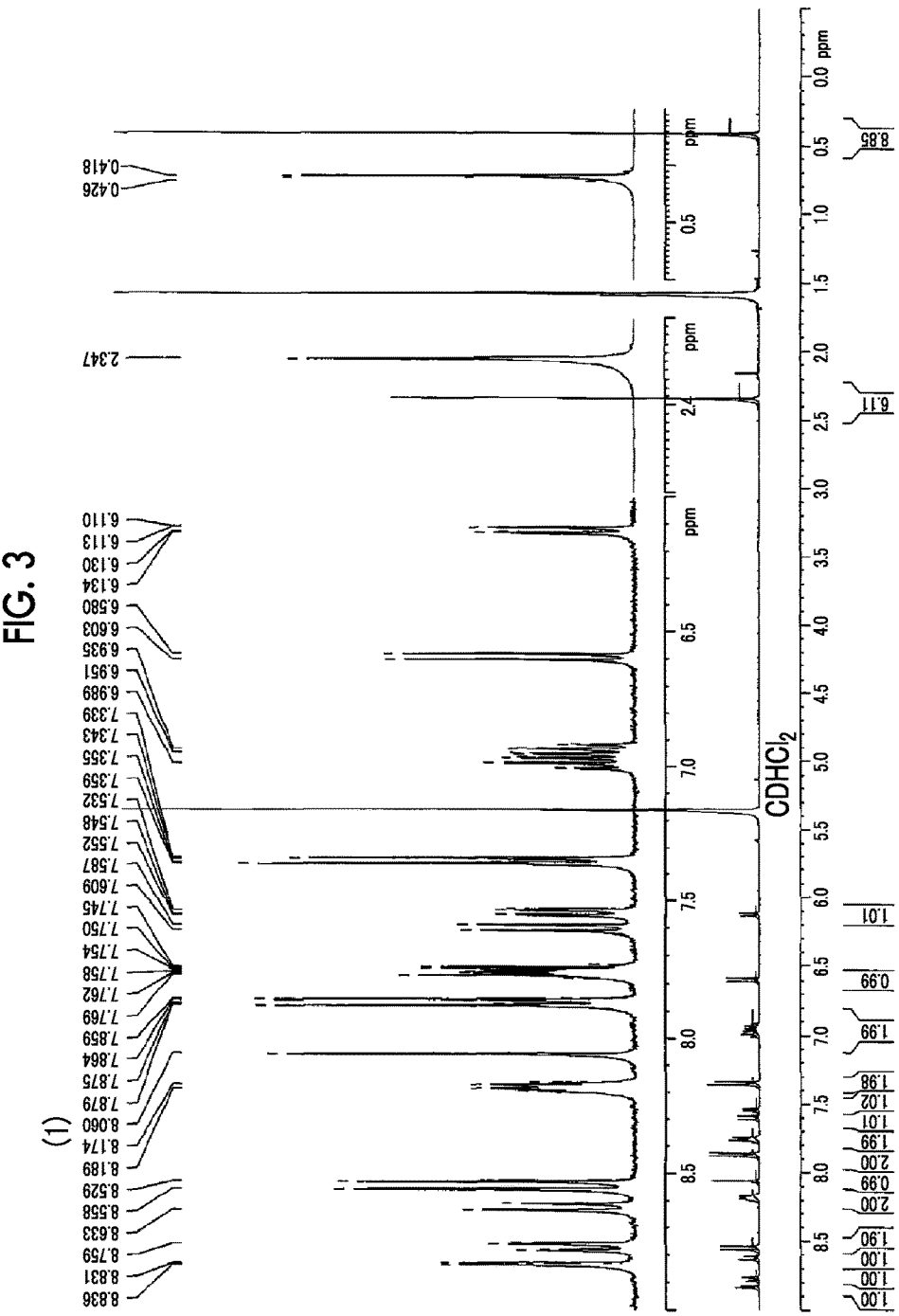
FIG. 3 is a $^1$H-NMR spectrum of a compound (1).

The following compound (photoelectric conversion material) (1) was synthesized through the following synthesis scheme. Identification of the compound was performed by MS measurement and $^1$H-NMR measurement. FIG. 3 shows a $^1$H-NMR spectrum of the synthesized compound (1). The following compound b as a starting material was synthesized according to the method described in JP2012-77064A. The synthesized compound (1) was subjected to purification by sublimation before production of a photoelectric conversion element to be described later.

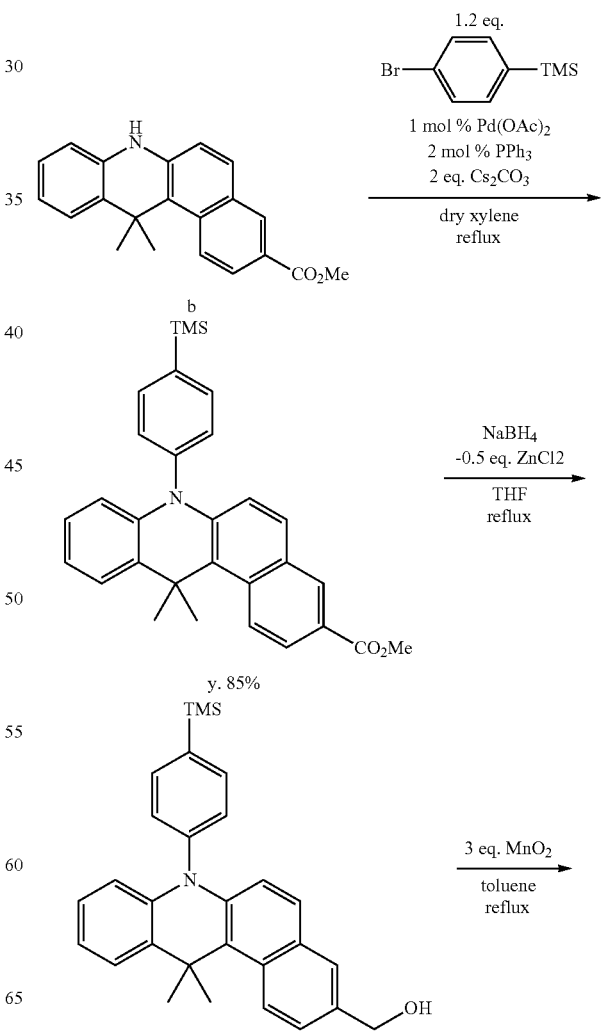

-continued

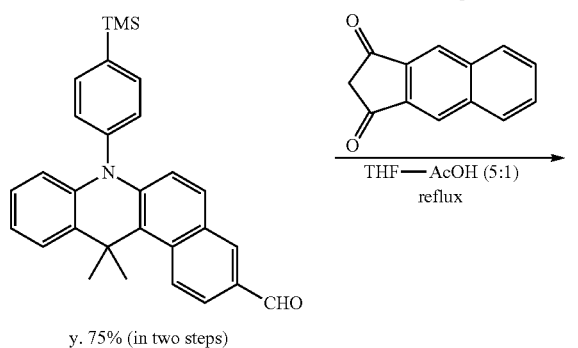

y. 75% (in two steps)

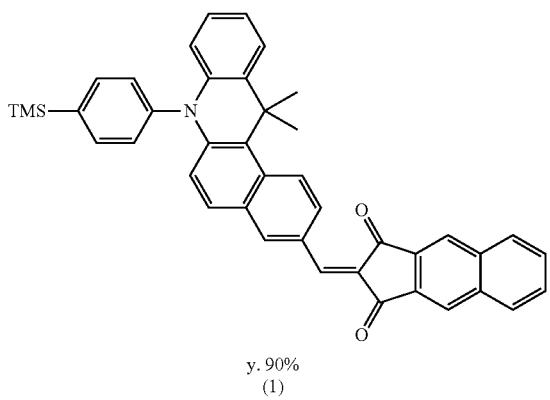

y. 90%
(1)

(Production of Photoelectric Conversion Element)

A photoelectric conversion element having the form of FIG. 1(a) was produced using the obtained compound (1). Here, the photoelectric conversion element is formed of a lower electrode 11, an electron blocking layer 16A, a photoelectric conversion film 12, and an upper electrode 15.

Specifically, a film of amorphous ITO was formed by a sputtering method on a glass substrate to form the lower electrode 11 (thickness: 30 nm), and a film of the following compound (EB-2a) was formed by a vacuum heating deposition method on the lower electrode 11 to form the electron blocking layer 16A (thickness: 100 nm).

In a state in which the temperature of the substrate was controlled to 25° C., on the electron blocking layer 16A, the compound (1) and fullerene ($C_{60}$) were co-deposited to form films by vacuum heating deposition with deposition amounts of 125 nm and 275 nm in terms of a single layer, respectively, and thus the photoelectric conversion film 12 was formed. Here, the deposition was performed by putting the compound (1) in a crucible and by then heating the compound (1) under vacuum (degree of vacuum of $4 \times 10^{-4}$ Pa or lower). In addition, the deposition was performed such that the deposition speed of the compound (1) was 3.0 Å (angstrom)/sec ($3.0 \times 10^{-10}$ m/sec).

On the photoelectric conversion film 12, a film of amorphous ITO was formed by a sputtering method to form the upper electrode 15 (transparent conductive film) (thickness: 10 nm). A SiO film was formed as a sealing layer on the upper electrode 15 by heating deposition, and then an aluminum oxide ($Al_2O_3$) was formed thereon by an ALCVD method to produce a photoelectric conversion element (first element).

(EB-2a)

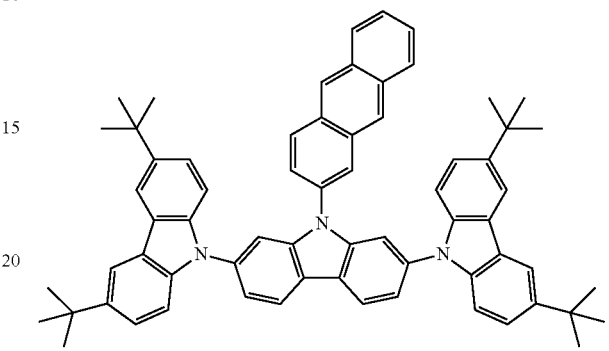

Next, the crucible (crucible in which the residual photoelectric conversion material was put) used in the production of the first element was used as it is, and deposition was performed for 5 hours while keeping the deposition speed to 3.0 Å/sec ($3.0 \times 10^{-10}$ m/sec). A photoelectric conversion element (second element) was produced according to the same procedures as in the case of the first element, except that after replacement with a new glass substrate, the deposition was performed using the photoelectric conversion material remaining in the crucible.

Examples 1-2 to 1-6 and Comparative Examples 1-1 to 1-5

Figure 4:
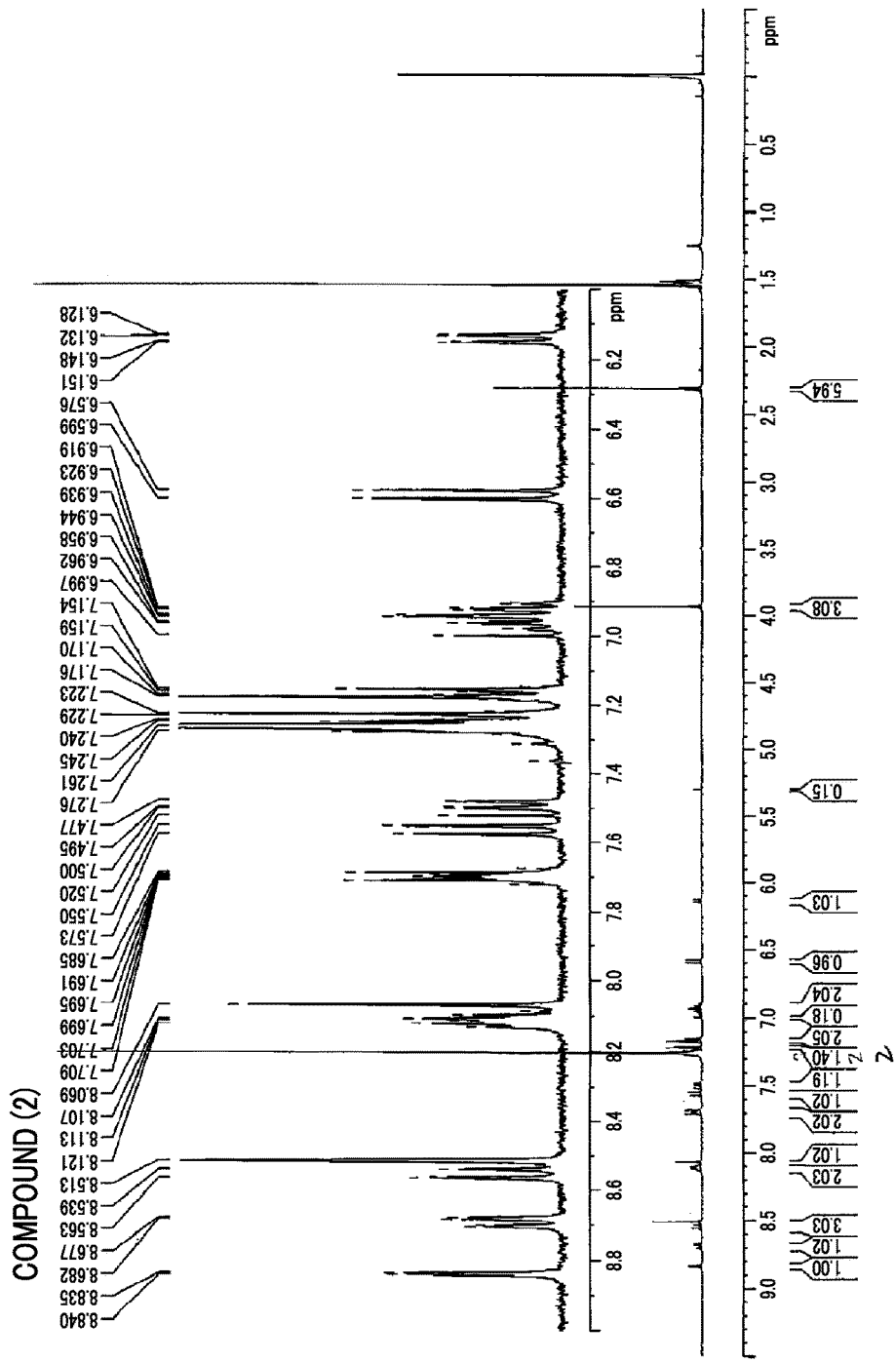
FIG. 4 is a $^1$H-NMR spectrum of a compound (2).
Figure 5:
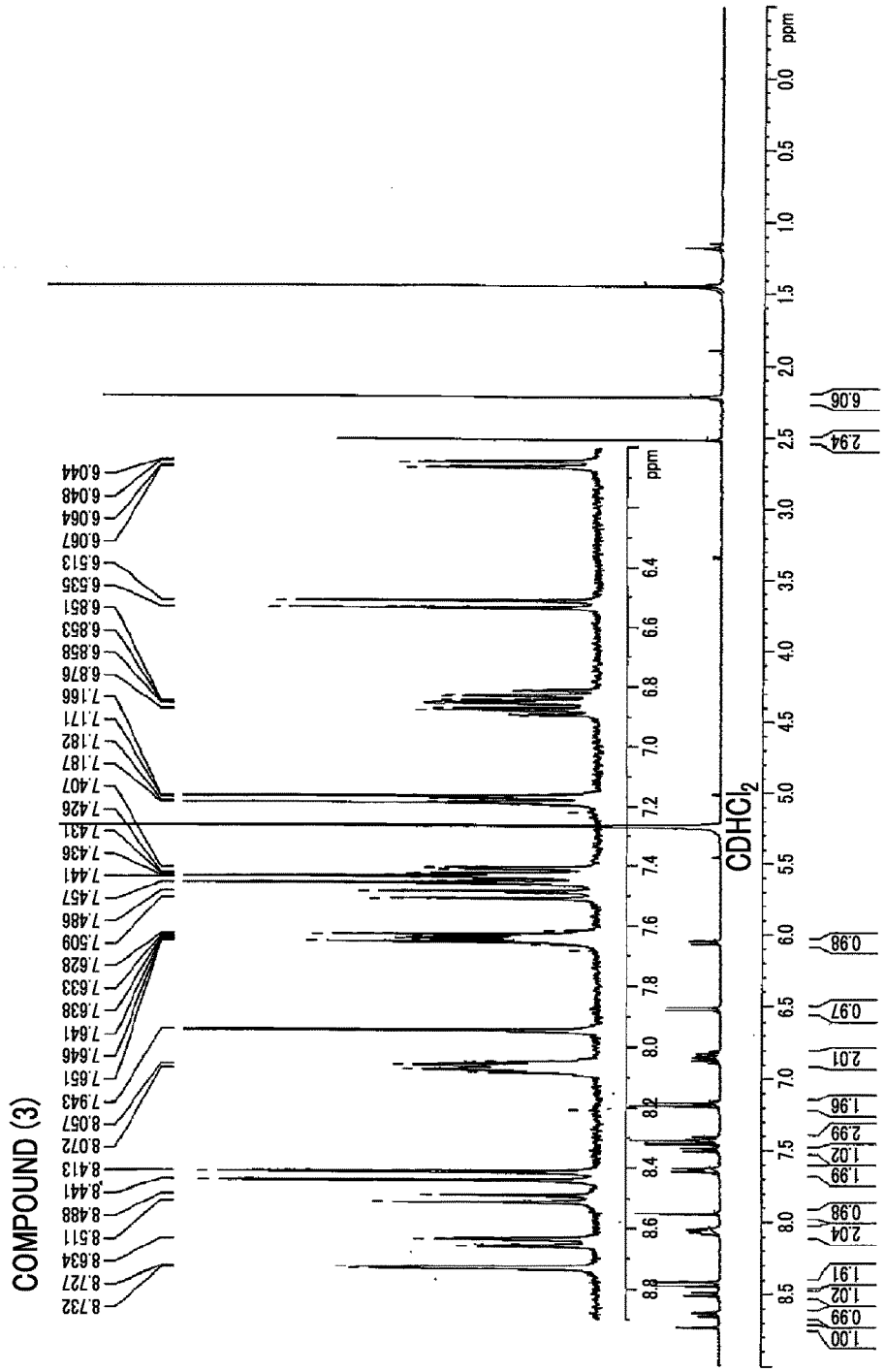
FIG. 5 is a $^1$H-NMR spectrum of a compound (3).
Figure 6:
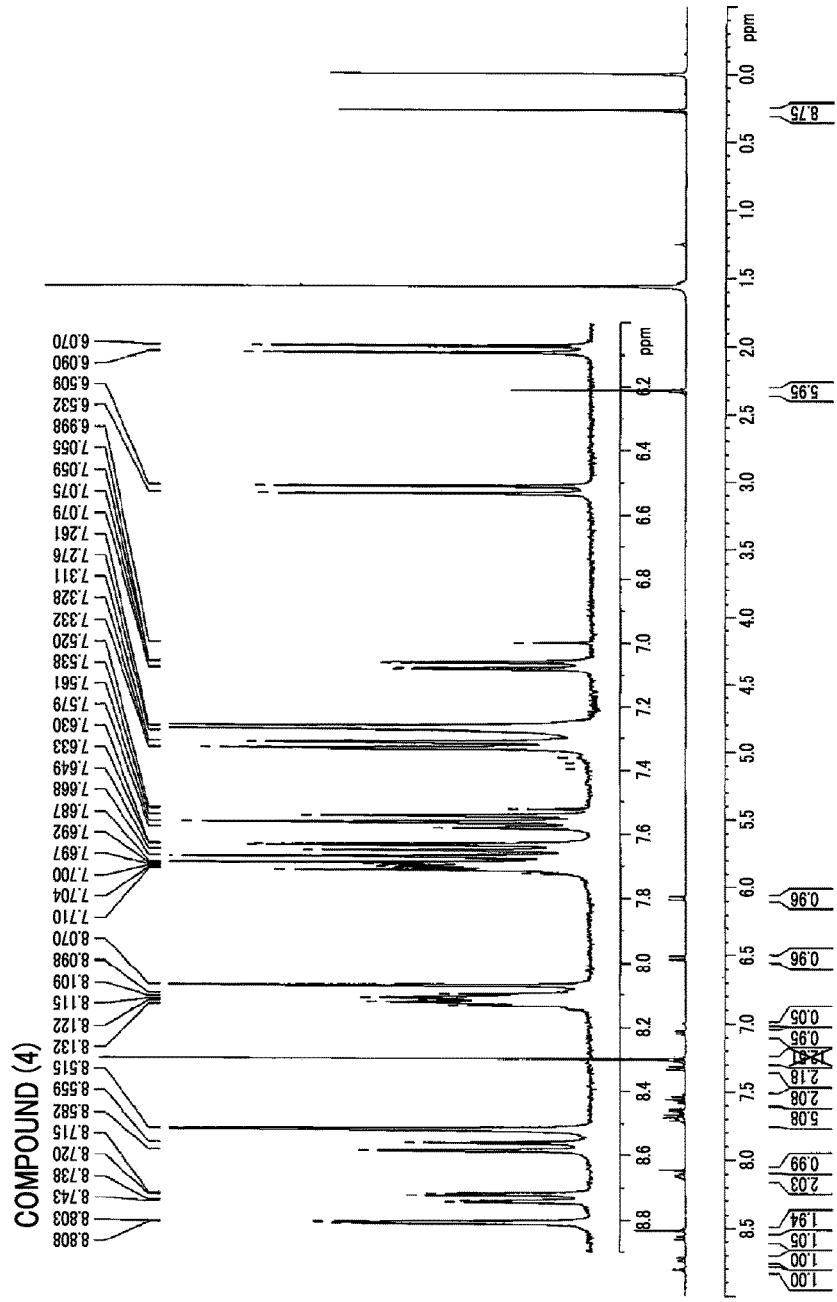
FIG. 6 is a $^1$H-NMR spectrum of a compound (4).

Using a known method, the following compounds (2) to (6) (photoelectric conversion materials of Examples 1-2 to 1-6) and comparative compounds (1) to (5) (photoelectric conversion materials of Comparative Examples 1-1 to 1-5) were synthesized. Identification of the compound was performed by MS measurement and $^1$H-NMR measurement. The comparative compounds (2) and (3) are compounds described in JP2012-77064A, and the comparative compound (4) is a compound described in JP2011-213706A. FIG. 4 shows a $^1$H-NMR spectrum of the synthesized compound (2), FIG. 5 shows a $^1$H-NMR spectrum of the synthesized compound (3), and FIG. 6 shows a $^1$H-NMR spectrum of the synthesized compound (4). The following compounds (2) to (6) and comparative compounds (1) to (5) were also subjected to purification by sublimation before production of a photoelectric conversion element.

Photoelectric conversion elements (first element and second element) were produced according to the same procedures as in Example 1-1, except that the following compounds (2) to (6) and comparative compounds (1) to (5) were respectively used in place of the compound (1).

In the following structural formulae, "TMS" indicates a trimethylsilyl group, "MeO—" (—OMe) indicates a methoxy group, and "MeS—" (—SMe) indicates a methylthio group ($CH_3$—S—).

(1)
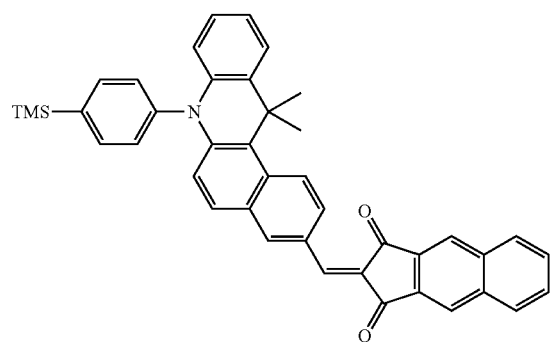
(2)
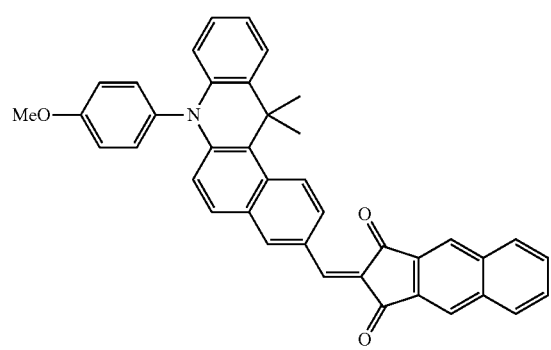
(3)
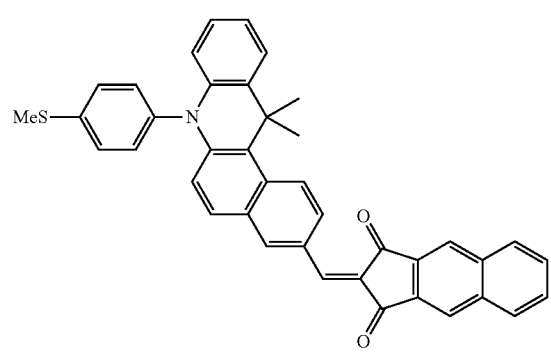
(4)
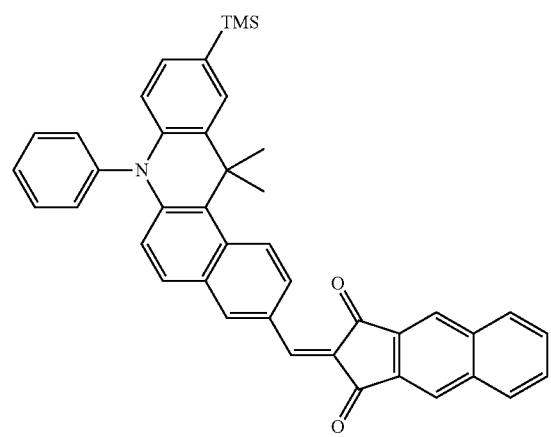
(5)
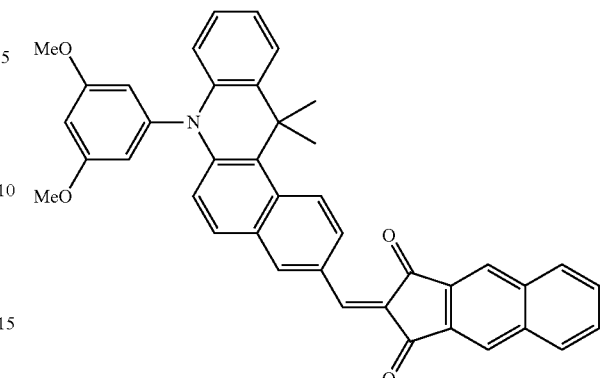
(6)
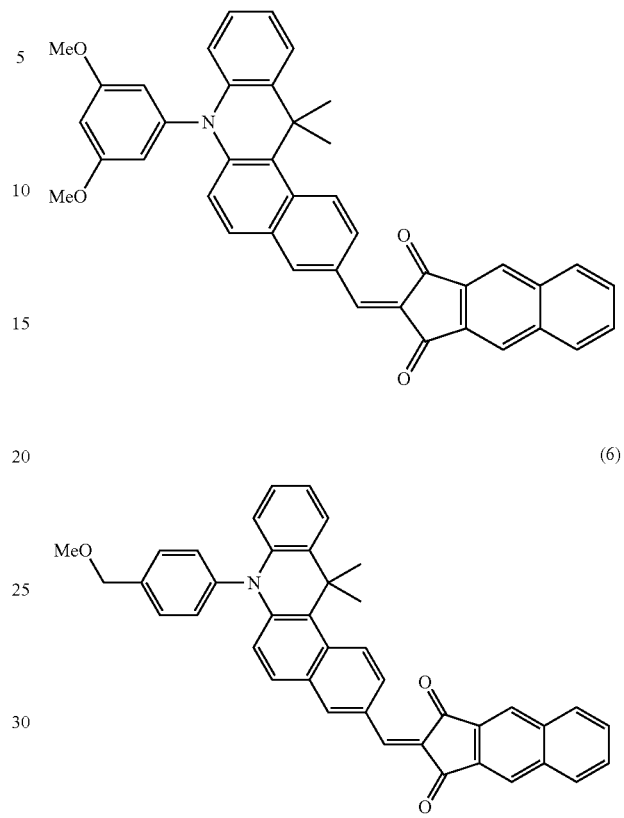

Comparative Compound (1) Comparative Compound (2)

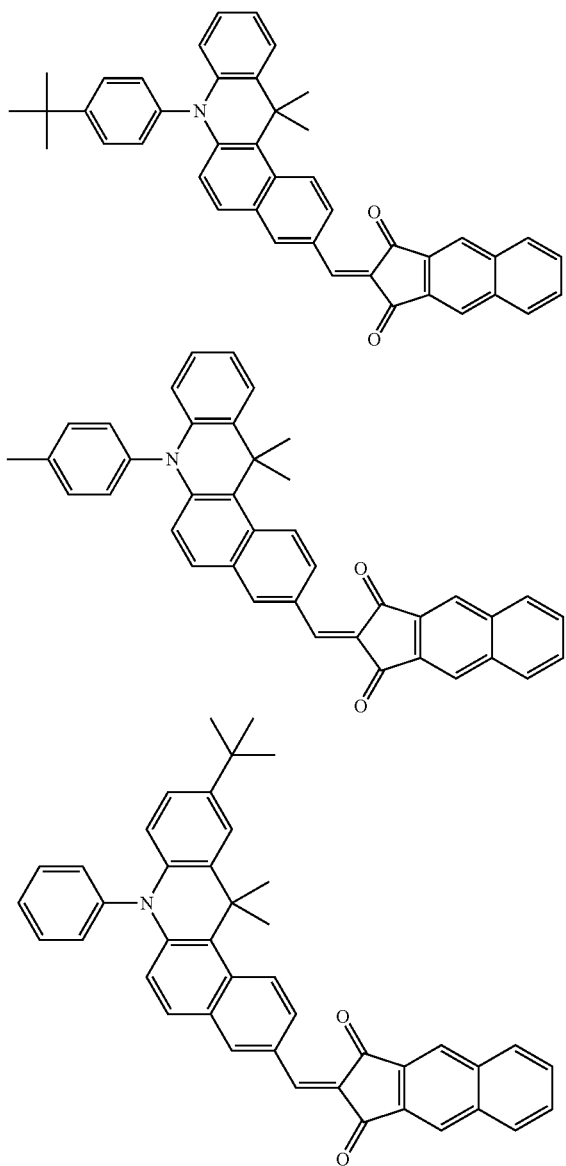

Comparative Compound (3) Comparative Compound (4) Comparative Compound (5)

<Confirmation of Driving of Element>

Whether the obtained photoelectric conversion elements (first element and second element) function as a photoelectric conversion element was confirmed. Specifically, current values in a dark place and in a bright place were measured by applying a voltage to the lower electrode and the upper electrode of the obtained photoelectric conversion element such that the field intensity was $2.0 \times 10^5$ V/cm. As a result, all of the photoelectric conversion elements showed a dark current of 100 nA/cm² or less in the dark place, but showed a current of 10 µA/cm² or greater in the bright place, and these were confirmed to function as a photoelectric conversion element.

<Crucible Residual Purity Retention Rate>

In the production of each photoelectric conversion element, the material remaining in the crucible after the production of the first element was subjected to HPLC measurement to obtain purities of the photoelectric conversion materials (compounds (1) to (6) and comparative compounds (1) to (5)) after the production of the first element. Similarly, the material remaining in the crucible after the production of the second element was subjected to HPLC measurement to obtain purities of the photoelectric conversion materials (compounds (1) to (6) and comparative compounds (1) to (5)) after the production of the second element. "Crucible residual purity retention rates" were obtained through the following expression.

Crucible Residual Purity Retention Rate=(purity after production of second element)/(purity after production of first element)

The results are shown in Table 1. The higher the "crucible residual purity retention rate", the more excellent the deposition stability of the photoelectric conversion material. The "crucible residual purity retention rate" is preferably 0.90 or higher for practical use.

TABLE 1

| Compound | | Crucible Residual Purity Retention Rate (Purity After Production of Second Element/Purity After Production of First Element) |
|---|---|---|
| Example 1-1 | (1) | 0.99 |
| Example 1-2 | (2) | 0.97 |
| Example 1-3 | (3) | 0.95 |
| Example 1-4 | (4) | 0.99 |
| Example 1-5 | (5) | 0.94 |
| Example 1-6 | (6) | 0.92 |
| Comparative Example 1-1 | Comparative Compound (1) | 0.78 |
| Comparative Example 1-2 | Comparative Compound (2) | 0.75 |
| Comparative Example 1-3 | Comparative Compound (3) | 0.83 |
| Comparative Example 1-4 | Comparative Compound (4) | 0.88 |
| Comparative Example 1-5 | Comparative Compound (5) | 0.85 |

As seen from Table 1, all of the examples of this application, each of which was the compound (A) expressed by Formula (1), exhibited excellent deposition stability. Among these, Examples 1-1 to 1-5 in which the position of the specific atom in the specific substituent was disposed at a bonding position exhibited more excellent deposition stability. Among these, Examples 1-1 to 1-4 in which the compound (A) was a compound expressed by Formula (3) and at least one of $R_{33}$ and $R_{38}$ in Formula (3) was the specific substituent exhibited even more excellent deposition stability. Among these, Examples 1-1 and 1-4 in which the compound (A) was a compound expressed by Formula (3) and the specific substituent included a silicon atom exhibited particularly excellent deposition stability.

In contrast, Comparative Examples 1-1 and 1-2 in which the triarylamine or the ring indicated by $Z_1$ in Formula (1) had the specific substituent, but the triarylamine in Formula (1) did not form a ring, and Comparative Examples 1-3 to 1-5 in which the triarylamine in Formula (1) formed a ring, but the triarylamine or the ring indicated by $Z_1$ in Formula (1) did not have the specific substituent were insufficient in deposition stability.

Examples 2-1 to 2-6 and Comparative Examples 2-1 to 2-5

Photoelectric conversion elements using the compounds (1) to (6) and the comparative compounds (1) to (5) as a photoelectric conversion material in a photoelectric conversion film were respectively produced. In order to check the change in the performance of the element when there were variations in the concentration of the photoelectric conversion material in the photoelectric conversion film, three types of photoelectric conversion elements (the total deposition amount of the photoelectric conversion material and fullerene ($C_{60}$) was fixed to 400 nm) in which the deposition amount ratio between the photoelectric conversion material and the fullerene ($C_{60}$) was changed were produced as follows in each case.

(a) A photoelectric conversion element (photoelectric conversion element indicated by a in Table 2) having an optimum deposition amount ratio.

(b) A photoelectric conversion element (photoelectric conversion element indicated by b in Table 2) in which a ratio of fullerene was reduced from the optimum deposition amount ratio (a ratio of the photoelectric conversion material was increased).

(c) A photoelectric conversion element (photoelectric conversion element indicated by c in Table 2) in which a ratio of fullerene was increased from the optimum deposition amount ratio (a ratio of the photoelectric conversion material was reduced).

The photoelectric conversion elements of Examples 2-1 to 2-6 and Comparative Examples 2-1 to 2-5 were produced according to the same procedures as in the case of the first element of Example 1-1, except that compounds (the compounds (1) to (6) and the comparative compounds (1) to (5)) shown in Table 2 were used as the photoelectric conversion material, and the co-deposition was performed such that the deposition amounts of the photoelectric conversion material and the fullerene ($C_{60}$) were as shown in "Photoelectric Conversion Material (nm): $C_{60}$ (nm)" of Table 2.

In "Photoelectric Conversion Material (nm): $C_{60}$ (nm)" of Table 2, "Photoelectric Conversion Material (nm)" indicates a deposition amount (nm) of the photoelectric conversion material in terms of a single layer, and "$C_{60}$ (nm)" indicates a deposition amount (nm) of the fullerene in terms of a single layer. In parentheses in the column of "Photoelectric Conversion Material (nm): $C_{60}$ (nm)" of Table 2, a ratio when the deposition amount of the photoelectric conversion material in terms of a single layer is 1 is shown.

<Change in Performance of Element Due to Change in Concentration (Variations in Concentration) of Photoelectric Conversion Material>

The photoelectric conversion elements (a, b, and c) of Examples 2-1 to 2-6 and Comparative Examples 2-1 to 2-5 were evaluated as follows concerning responsiveness and photoelectric conversion efficiency (external quantum efficiency). As a result, in all of a, b, and c, elements of which the responsiveness was "A" or "B" and the photoelectric conversion efficiency (external quantum efficiency) was "A" or "B" were evaluated as "A" as elements in which the change in the performance of the element due to variations in the concentration of the photoelectric conversion material was small (the performance of the element was maintained at a high level), and elements excluding the above elements were evaluated as "B" as elements in which the change in the performance of the element due to variations in the concentration of the photoelectric conversion material was large, or the level of the performance of the element was insufficient even when the change in the performance of the element was small. Elements evaluated as "A" are preferred for practical use.

(Responsiveness)

An electric field of $2.0 \times 10^5$ V/cm was applied to the photoelectric conversion element, and a photocurrent when light was applied from the side of the upper electrode (transparent conductive film) was measured to obtain a time of rise to a signal intensity of 98% from 0. As a result, when a time of rise of the photoelectric conversion element a of Example 2-1 (hereinafter, also referred to as Example 2-1-a) was set to 1, elements having a relative value of 1.1 or less were evaluated as "A", elements having a relative value which was greater than 1.1 and was not greater than 1.3 were evaluated as "B", and elements having a relative value which was greater than 1.3 were evaluated as "C". The results are shown in Table 2. Elements evaluated as "A" or "B" are preferred, and elements evaluated as "A" are more preferred for practical use.

The relative value is calculated through the following expression.

(Relative Value)=(Time of Rise to Signal Intensity of 98% from 0 in Each Photoelectric Conversion Element/Time of Rise to Signal Intensity of 98% from 0 in Photoelectric Conversion Element a of Example 2-1)

(Photoelectric Conversion Efficiency (External Quantum Efficiency)

A voltage was applied to the lower electrode and the upper electrode of the photoelectric conversion element such that the field intensity was $2.0 \times 10^5$ V/cm, and external quantum efficiency at a wavelength of 580 nm at this voltage was measured. As a result, when external quantum efficiency of the photoelectric conversion element a of Example 2-1 (Example 2-1-a) was set to 1, elements having a relative value of 0.8 or greater were evaluated as "A", elements having a relative value of 0.75 to less than 0.8 were evaluated as "B", and elements having a relative value which was less than 0.75 were evaluated as "C". The results are shown in Table 2. Elements evaluated as "A" or "B" are preferred, and elements evaluated as "A" are more preferred for practical use.

TABLE 2

| | Photoelectric Conversion Material | Photoelectric Conversion Element | Photoelectric Conversion Material (nm):$C_{60}$ (nm) | Responsiveness | Photoelectric Conversion Efficiency | Change in Performance of Element Due to Change in Concentration of Photoelectric Conversion Material |
|---|---|---|---|---|---|---|
| Example 2-1 | (1) | a | 133:267 (1:2.0) | A | A | A |
| | | b | 143:257 (1:1.8) | A | A | |
| | | c | 125:275 (1:2.2) | A | A | |

TABLE 2-continued

| Photoelectric Conversion Material | | Photoelectric Conversion Element | Photoelectric Conversion Material (nm):$C_{60}$ (nm) | Responsiveness | Photoelectric Conversion Efficiency | Change in Performance of Element Due to Change in Concentration of Photoelectric Conversion Material |
|---|---|---|---|---|---|---|
| Example 2-2 | (2) | a | 125:275 (1:2.2) | A | A | A |
|  |  | b | 133:267 (1:2.0) | B | A |  |
|  |  | c | 118:282 (1:2.4) | A | A |  |
| Example 2-3 | (3) | a | 133:267 (1:2.0) | A | A | A |
|  |  | b | 143:257 (1:1.8) | B | A |  |
|  |  | c | 125:275 (1:2.2) | A | A |  |
| Example 2-4 | (4) | a | 133:267 (1:2.0) | A | A | A |
|  |  | b | 143:257 (1:1.8) | A | A |  |
|  |  | c | 125:275 (1:2.2) | A | B |  |
| Example 2-5 | (5) | a | 133:267 (1:2.0) | B | A | A |
|  |  | b | 143:257 (1:1.8) | B | A |  |
|  |  | c | 125:275 (1:2.2) | B | A |  |
| Example 2-6 | (6) | a | 133:267 (1:2.0) | B | A | A |
|  |  | b | 143:257 (1:1.8) | B | A |  |
|  |  | c | 125:275 (1:2.2) | B | B |  |
| Comparative Example 2-1 | Comparative Compound (1) | a | 133:267 (1:2.0) | B | B | B |
|  |  | b | 143:257 (1:1.8) | C | B |  |
|  |  | c | 125:275 (1:2.2) | B | C |  |
| Comparative Example 2-2 | Comparative Compound (2) | a | 125:275 (1:2.2) | B | B | B |
|  |  | b | 133:267 (1:2.0) | C | B |  |
|  |  | c | 118:282 (1:2.4) | B | C |  |
| Comparative Example 2-3 | Comparative Compound (3) | a | 133:267 (1:2.0) | B | B | B |
|  |  | b | 143:257 (1:1.8) | C | A |  |
|  |  | c | 125:275 (1:2.2) | B | C |  |
| Comparative Example 2-4 | Comparative Compound (4) | a | 125:275 (1:2.2) | B | B | B |
|  |  | b | 133:267 (1:2.0) | C | A |  |
|  |  | c | 118:282 (1:2.4) | B | C |  |
| Comparative Example 2-5 | Comparative Compound (5) | a | 133:267 (1:2.0) | B | B | B |
|  |  | b | 143:257 (1:1.8) | C | A |  |
|  |  | c | 125:275 (1:2.2) | B | C |  |

As seen from Table 2, in all of the photoelectric conversion elements of the examples of this application using the photoelectric conversion material which was the compound (A) expressed by Formula (1) on the photoelectric conversion film, the change in the performance of the element was small even when there were variations in the concentration of the photoelectric conversion material in the photoelectric conversion film. Among these, Example 2-1 in which the compound (A) was a compound expressed by Formula (3), $R_{33}$ in Formula (3) was the specific substituent, and the specific substituent included a silicon atom had even less change in the performance of the element when there were variations in the concentration of the photoelectric conversion material in the photoelectric conversion film.

In contrast, in the photoelectric conversion elements of Comparative Examples 2-1 and 2-2 in which the triarylamine or the ring indicated by $Z_1$ in Formula (1) had the specific substituent, but the triarylamine in Formula (1) did not form a ring, and in the photoelectric conversion elements of Comparative Examples 2-3 to 2-5 in which the triarylamine in Formula (1) formed a ring, but the triarylamine or the ring indicated by $Z_1$ in Formula (1) did not have the specific substituent, the change in the performance of the element due to variations in the concentration of the photoelectric conversion material in the photoelectric conversion film was large, or the level of the performance of the element was insufficient even when the change in the performance of the element was small.

Examples 3-1 to 3-3

Photoelectric conversion elements (Examples 3-1 to 3-3) were produced according to the same procedures as in the case of the photoelectric conversion element a of Example 2-1 (Example 2-1-a), except that electron blocking materials (the following (EB-2b), (EB-1a), and (TPT1)) shown in the following Table 3 were used in place of the compound (EB-2a) as a material of the electron blocking layer.

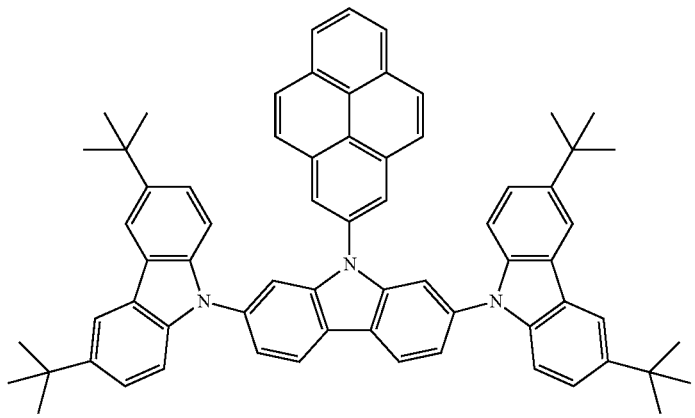

(EB-2b)

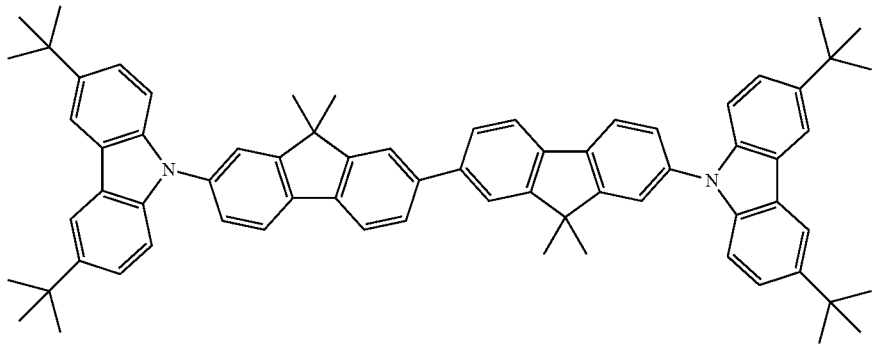

(EB-1a)

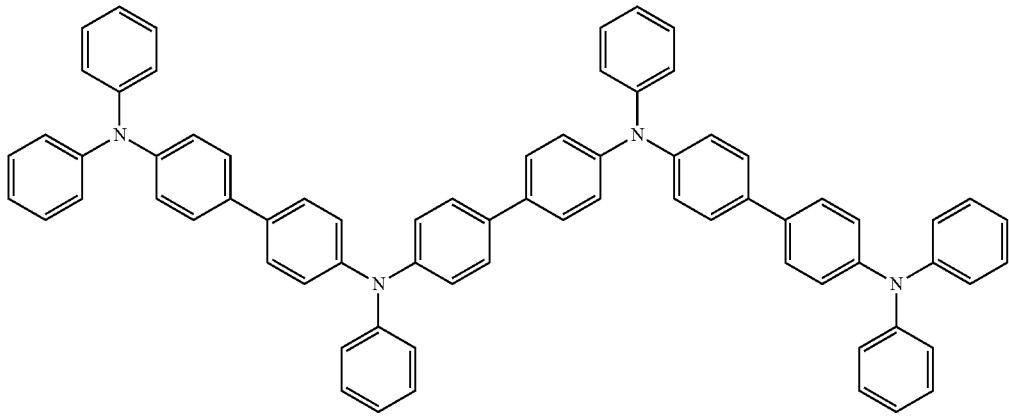

(TPT1)

The photoelectric conversion elements of Examples 3-1 to 3-3 and Example 2-1-a were evaluated as follows concerning responsiveness and dark current. Examples 3-1 to 3-3 were evaluated concerning the above-described "Change in Performance of Element due to Variations in Concentration of Photoelectric Conversion Material", and the results were the same as in Example 2-1. That is, the performance of the element did not change due to variations in the concentration of the photoelectric conversion material even when the electron blocking material was changed to (EB-2b), (EB-1a), or (TPT1) in Example 2-1.

(Dark Current)

The photoelectric conversion elements of Examples 3-1 to 3-3 and Example 2-1-a were subjected to an annealing treatment (leaving for 30 minutes on hot plate at 200° C.), and were cooled to room temperature. Then, a dark current value was measured. As a result, when a dark current value of the photoelectric conversion element of Example 2-1-a was set to 1, elements having a relative value of 5 or less were evaluated as "A", elements having a relative value which was greater than 5 and was not greater than 20 were evaluated as "B", and elements having a relative value which was greater than 20 were evaluated as "C". The results are shown in Table 3 (after heating at 200° C.). Elements evaluated as "A" or "B" are preferred, and elements evaluated as "A" are more preferred for practical use.

The relative value is calculated through the following expression.

(Relative Value)=(Dark Current Value of Each Photoelectric Conversion Element/Dark Current Value of Photoelectric Conversion Element of Example 2-1-*a*)

Furthermore, the photoelectric conversion elements of Examples 3-1 to 3-3 and Example 2-1-a were further subjected to an annealing treatment (leaving for 10 minutes on hot plate at 220° C.) at high temperature, and were cooled to room temperature. Then, a dark current value was measured. As a result, elements in which a relative value of the dark current value after the heating at 220° C. to the above-described dark current value after the heating at 200° C. was 3 or less were evaluated as "A", elements having a relative value which was greater than 3 and was not greater than 5 were evaluated as "B", and elements having a relative value which was greater than 5 were evaluated as "C". The results are shown in Table 3 (After Heating at 220° C.). Elements evaluated as "A" or "B" are preferred, and elements evaluated as "A" are more preferred for practical use.

From the viewpoint of heat resistance, elements evaluated as "A" or "B" after the heating at 200° C. and after the heating at 220° C. are preferred, elements evaluated as "A" after at least one of the heating at 200° C. and the heating at 220° C. are more preferred, and elements evaluated as "A" after the heating at 200° C. and after the heating at 220° C. are even more preferred.

(Responsiveness)

The photoelectric conversion elements of Examples 3-1 to 3-3 and Example 2-1-a were subjected to an annealing treatment (leaving for 30 minutes on hot plate at 200° C.), and were cooled to room temperature. Then, responsiveness was evaluated. Specifically, an electric field of $1.0 \times 10^5$ V/cm was applied to the photoelectric conversion element after the annealing treatment, and a photocurrent when light was applied from the side of the upper electrode (transparent conductive film) was measured to obtain a time of rise to a signal intensity of 98% from 0. As a result, when a time of rise of the photoelectric conversion element a of Example 2-1-a was set to 1, elements having a relative value of 1.2 or less were evaluated as "A", elements having a relative value which was greater than 1.2 and was not greater than 1.5 were evaluated as "B", and elements having a relative value which was greater than 1.5 were evaluated as "C". The results are shown in Table 3 (after heating at 200° C.). Elements evaluated as "A" or "B" are preferred, and elements evaluated as "A" are more preferred for practical use.

The relative value is calculated through the following expression.

(Relative Value)=(Time of Rise to Signal Intensity of 98% from 0 in Each Photoelectric Conversion Element/Time of Rise to Signal Intensity of 98% from 0 in Photoelectric Conversion Element of Example 2-1-a)

Furthermore, the photoelectric conversion elements of Examples 3-1 to 3-3 and Example 2-1-a were further subjected to an annealing treatment (leaving for 10 minutes on hot plate at 220° C.) at high temperature, and were cooled to room temperature. Then, responsiveness was measured. As a result, elements in which a relative value of the time of rise after the heating at 220° C. to the above-described time of rise after the heating at 200° C. was 2 or less were evaluated as "A", elements having a relative value which was greater than 2 and was not greater than 5 were evaluated as "B", and elements having a relative value which was greater than 5 were evaluated as "C". Elements evaluated as "A" or "B" are preferred, and elements evaluated as "A" are more preferred for practical use.

From the viewpoint of heat resistance, elements evaluated as "A" or "B" after the heating at 200° C. and after the heating at 220° C. are preferred, elements evaluated as "A" after at least one of the heating at 200° C. and the heating at 220° C. are more preferred, and elements evaluated as "A" after the heating at 200° C. and after the heating at 220° C. are even more preferred.

TABLE 3

| | | Dark Current | | Responsiveness | |
|---|---|---|---|---|---|
| | Electron Blocking Material | After Heating at 200° C. | After Heating at 220° C. | After Heating at 200° C. | After Heating at 220° C. |
| Example 2-1-a | EB-2a | A | B | A | B |
| Example 3-1 | EB-2b | A | A | A | A |
| Example 3-2 | EB-1a | A | B | B | B |
| Example 3-3 | TPT1 | B | C | B | C |

From the comparison between Example 2-1-a and Examples 3-1 to 3-3, Example 2-1-a and Examples 3-1 and 3-2 in which the electron blocking layer contained the compound expressed by Formula (EB-1) exhibited excellent heat resistance. Among these, Example 2-1-a and Example 3-1 in which the electron blocking layer contained the compound expressed by Formula (EB-2) exhibited more excellent heat resistance. Furthermore, among these, Example 3-1 in which the electron blocking layer contained the compound expressed by Formula (EB-2) and the total number of carbon atoms was 15 or greater exhibited even more excellent heat resistance.

<Production of Imaging Element>

An imaging element having the same form as that shown in FIG. 2 was produced. That is, a film of amorphous TiN having a thickness of 30 nm was formed by a sputtering method on a CMOS substrate, and then a lower electrode was formed by patterning by photolithography such that one pixel existed on each photodiode (PD) on the CMOS substrate, and subsequent processes after the formation of a film of an electron blocking material were performed according to the same procedures as in Examples 1-1 to 1-4 and Comparative Examples 1-1 to 1-5 to produce imaging elements. The evaluation thereof was also performed in the same manner. The same results as in Table 1 were obtained, and it was found that the compounds (1) to (6) exhibit excellent deposition stability as a photoelectric conversion material for an imaging element.

In addition, subsequent processes after the formation of a film of an electron blocking material were performed according to the same procedures as in Examples 2-1 to 2-4 and Comparative Examples 2-1 to 2-5 to produce imaging elements. The evaluation thereof was also performed in the same manner. The same results as in Table 2 were obtained, and it was found that in the imaging elements using the compounds (1) to (6) as a photoelectric conversion material in the photoelectric conversion film, the change in the performance of the element due to variations in the concentration of the photoelectric conversion material was small.

In addition, subsequent processes after the formation of a film of an electron blocking material were performed according to the same procedures as in Examples 3-1 to 3-3 to produce imaging elements. The evaluation thereof was also performed in the same manner, and the same results as in Table 3 were obtained.

EXPLANATION OF REFERENCES 10a, 10b: photoelectric conversion element
11: lower electrode (conductive film)
12: photoelectric conversion film 15: upper electrode (transparent conductive film)
16A: electron blocking layer
16B: hole blocking layer
100: imaging element
101: substrate
102: insulating layer
103: connection electrode
104: pixel electrode (lower electrode)
105: connection portion
106: connection portion
107: photoelectric conversion film
108: counter electrode (upper electrode)
109: buffer layer
110: sealing layer
111: color filter (CF)
112: partition wall
113: light shielding layer
114: protective layer
115: counter electrode voltage supply portion
116: readout circuit

What is claimed is:

1. A photoelectric conversion material that is a compound (a2) expressed by the following Formula (3):

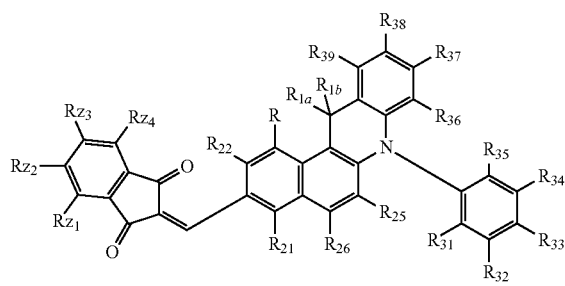

Formula (3)

in Formula (3), each of $Rz_1$ to $Rz_4$ independently indicates a hydrogen atom or a substituent, and $Rz_1$ and $Rz_2$; $Rz_2$ and $Rz_3$; and $Rz_3$ and $Rz_4$ may be respectively bonded to each other to form a ring, each of $R_{21}$, $R_{22}$, $R_{23}$, $R_{25}$, and $R_{26}$ independently indicates a hydrogen atom or a substituent, each of $R_{1a}$ and $R_{1b}$ independently indicates a hydrogen atom or a substituent, each of $R_{31}$ to $R_{35}$ independently indicates a hydrogen atom or a substituent, each of $R_{36}$ to $R_{39}$ independently indicates a hydrogen atom or a substituent, and at least one of the following (i) and (ii) is satisfied:

(i) at least one of $R_{31}$ to $R_{39}$ is a specific substituent, and (ii) at least one of $R_{21}$, $R_{22}$, $R_{23}$, $R_{25}$, and $R_{26}$ is a specific substituent, wherein the specific substituent is expressed by one of the following Formulae (X2) to (X5):

$$*-L-S-R, \quad \text{Formula (X2)}$$

$$*-L-Se-R, \quad \text{Formula (X3)}$$

$$*-L-\underset{\underset{R}{|}}{\overset{\overset{R}{|}}{Si}}-R, \text{ and} \quad \text{Formula (X4)}$$

$$*-L-\underset{\underset{R}{|}}{\overset{\overset{R}{|}}{Ge}}-R \quad \text{Formula (X5)}$$

in Formulae (X2) to (X5), R indicates a hydrocarbon group, L indicates a single bond, and * indicates a bonding position.

2. The photoelectric conversion material according to claim 1, wherein at least one of $R_{33}$ and $R_{38}$ is the specific substituent, and at least one type of atom selected from the group consisting of oxygen atom, sulfur atom, selenium atom, silicon atom, and germanium atom included in the specific substituent is directly bonded to a carbon atom to which $R_{33}$ or $R_{38}$ is bonded.

3. The photoelectric conversion material according to claim 1, wherein the specific substituent includes a silicon atom.

* * * * *